(12) United States Patent
Sjolund et al.

(10) Patent No.: US 11,957,884 B2
(45) Date of Patent: Apr. 16, 2024

(54) INSULIN INJECTION ASSISTANCE SYSTEMS, METHODS, AND DEVICES

(71) Applicant: Bigfoot Biomedical, Inc., Milpitas, CA (US)

(72) Inventors: John Sjolund, Los Altos, CA (US); Ambika Srinath, San Francisco, CA (US); Andrew Bochenko, Redwood City, CA (US); George Crothall, Oceanside, CA (US); Bryan Mazlish, Palo Alto, CA (US); Jennifer Martin Block, Menlo Park, CA (US); Sarah Matarese, San Jose, CA (US); Linda Mackowiak, Cazenovia, NY (US); Lane Desborough, Thousand Oaks, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 114 days.

(21) Appl. No.: 17/444,007

(22) Filed: Jul. 29, 2021

(65) Prior Publication Data
US 2021/0386936 A1 Dec. 16, 2021

Related U.S. Application Data

(63) Continuation of application No. 16/218,212, filed on Dec. 12, 2018, now Pat. No. 11,083,852.
(Continued)

(51) Int. Cl.
| *A61M 5/315* | (2006.01) |
| *A61B 5/145* | (2006.01) |
(Continued)

(52) U.S. Cl.
CPC ..... *A61M 5/31546* (2013.01); *A61B 5/14532* (2013.01); *A61K 38/28* (2013.01);
(Continued)

(58) Field of Classification Search
CPC . A61B 5/0022; A61B 5/14532; A61B 5/4839; A61B 5/746; A61M 2205/3553;
(Continued)

(56) References Cited

U.S. PATENT DOCUMENTS

| 4,498,904 A | 2/1985 | Turner et al. |
| 4,515,584 A | 5/1985 | Abe et al. |
(Continued)

FOREIGN PATENT DOCUMENTS

| CA | 2925458 A1 | 4/2015 |
| CN | 201248860 Y | 6/2009 |
(Continued)

OTHER PUBLICATIONS

"Calculating Insulin Dose." Diabetes Education Online, University of California, San Francisco, dtc.ucsf.edu/types-of-diabetes/type2/treatment-of-type-2-diabetes/medications-and-therapies/type-2-insulin-rx/calculating-insulin-dose/. Retrieved Nov. 2020.
(Continued)

*Primary Examiner* — Deanna K Hall
(74) *Attorney, Agent, or Firm* — TraskBritt

(57) ABSTRACT

One or more embodiments of the disclosure relate, generally, to a system to assist with manual dosing of insulin. Such a system may include a glucose sensor system, a reusable insulin dosing detector, and a recommendation system. The reusable insulin dosing detector may be configured to be reversibly connectable to a disposable component that may form part of an insulin manual delivery assembly. The reusable insulin dosing detector may be configured to detect insulin delivery associated with the
(Continued)

insulin manual delivery assembly. The recommendation system may be configured to analyze blood glucose data and determine adjustments to insulin therapy settings.

20 Claims, 39 Drawing Sheets

Related U.S. Application Data

(60) Provisional application No. 62/682,878, filed on Jun. 9, 2018, provisional application No. 62/628,808, filed on Feb. 9, 2018, provisional application No. 62/597,809, filed on Dec. 12, 2017, provisional application No. 62/597,868, filed on Dec. 12, 2017.

(51) Int. Cl.

| | | |
|---|---|---|
| *A61K 38/28* | (2006.01) | |
| *A61M 5/20* | (2006.01) | |
| *A61M 5/32* | (2006.01) | |
| *G16H 20/13* | (2018.01) | |
| A61B 5/00 | (2006.01) | |
| A61M 5/31 | (2006.01) | |
| G16H 50/20 | (2018.01) | |

(52) U.S. Cl.
CPC ............ *A61M 5/20* (2013.01); *A61M 5/3202* (2013.01); *G16H 20/13* (2018.01); A61B 5/4839 (2013.01); A61B 5/681 (2013.01); A61M 2005/3125 (2013.01); A61M 2205/18 (2013.01); A61M 2205/3561 (2013.01); A61M 2205/3584 (2013.01); A61M 2205/505 (2013.01); A61M 2205/581 (2013.01); A61M 2205/582 (2013.01); A61M 2205/583 (2013.01); A61M 2209/06 (2013.01); A61M 2230/201 (2013.01); G16H 50/20 (2018.01)

(58) Field of Classification Search
CPC ...... A61M 2205/3569; A61M 2205/52; A61M 2230/201; A61M 5/3202
See application file for complete search history.

(56) References Cited

U.S. PATENT DOCUMENTS

| | | |
|---|---|---|
| 4,950,216 A | 8/1990 | Weder |
| 4,973,318 A | 11/1990 | Holm et al. |
| 4,988,660 A | 1/1991 | Campbell |
| 5,233,571 A | 8/1993 | Wirtschafter |
| 5,279,586 A | 1/1994 | Balkwill |
| 5,523,560 A | 6/1996 | Manique et al. |
| 5,536,249 A | 7/1996 | Castellano et al. |
| 5,564,414 A | 10/1996 | Walker et al. |
| 5,626,566 A | 5/1997 | Petersen et al. |
| 5,640,954 A | 6/1997 | Pfeiffer et al. |
| 5,645,534 A | 7/1997 | Chanoch |
| 5,665,065 A | 9/1997 | Colman et al. |
| 5,678,571 A | 10/1997 | Brown |
| 5,681,285 A | 10/1997 | Ford et al. |
| 5,822,715 A | 10/1998 | Worthington et al. |
| 5,918,603 A | 7/1999 | Brown |
| 5,925,021 A | 7/1999 | Castellano et al. |
| 5,984,900 A | 11/1999 | Mikkelsen |
| 6,004,297 A | 12/1999 | Steenfeldt-Jensen et al. |
| 6,032,119 A | 2/2000 | Brown et al. |
| 6,042,571 A | 3/2000 | Hjertman et al. |
| 6,235,004 B1 | 5/2001 | Steenfeldt-Jensen et al. |
| 6,287,283 B1 | 9/2001 | Ljunggreen et al. |
| 6,302,855 B1 | 10/2001 | Lav et al. |
| 6,354,996 B1 | 3/2002 | Drinan et al. |
| 6,482,185 B1 | 11/2002 | Hartmann |
| 6,650,951 B1 | 11/2003 | Jones et al. |
| 6,685,678 B2 | 2/2004 | Evans et al. |
| 6,810,290 B2 | 10/2004 | Lebel et al. |
| 6,817,986 B2 | 11/2004 | Slate et al. |
| 6,827,702 B2 | 12/2004 | Lebel et al. |
| 6,956,572 B2 | 10/2005 | Zaleski |
| 7,025,743 B2 | 4/2006 | Mann et al. |
| 7,109,878 B2 | 9/2006 | Mann et al. |
| 7,133,329 B2 | 11/2006 | Skyggebjerg et al. |
| 7,241,265 B2 | 7/2007 | Cummings et al. |
| 7,291,107 B2 | 11/2007 | Hellwig et al. |
| 7,343,197 B2 | 3/2008 | Shusterman |
| 7,397,730 B2 | 7/2008 | Skyggebjerg et al. |
| 7,404,796 B2 | 7/2008 | Ginsberg |
| 7,454,359 B2 | 11/2008 | Rosenfeld et al. |
| 7,553,281 B2 | 6/2009 | Hellwig et al. |
| 7,570,980 B2 | 8/2009 | Ginsberg |
| 7,591,801 B2 | 9/2009 | Brauker et al. |
| 7,647,237 B2 | 1/2010 | Malave et al. |
| 7,713,229 B2 | 5/2010 | Veit et al. |
| 7,751,907 B2 | 7/2010 | Blomquist |
| 7,837,647 B2 | 11/2010 | Estes et al. |
| 7,850,641 B2 | 12/2010 | Lebel et al. |
| 7,871,376 B2 | 1/2011 | Brown |
| 7,878,975 B2 | 2/2011 | Liljeryd et al. |
| 7,905,833 B2 | 3/2011 | Brister et al. |
| 7,931,613 B2 | 4/2011 | Haueter et al. |
| 7,955,303 B2 | 6/2011 | Burren et al. |
| 7,976,492 B2 | 7/2011 | Brauker et al. |
| 8,012,119 B2 | 9/2011 | Estes et al. |
| 8,052,655 B2 | 11/2011 | Moeller et al. |
| 8,108,299 B1 | 1/2012 | Waelbroeck et al. |
| 8,127,946 B2 | 3/2012 | Winig et al. |
| 8,132,101 B2 | 3/2012 | Buck et al. |
| 8,156,070 B2 | 4/2012 | Buck et al. |
| 8,206,340 B2 | 6/2012 | Arefieg |
| 8,217,946 B2 | 7/2012 | Halpern et al. |
| 8,219,222 B2 | 7/2012 | Blomquist |
| 8,221,345 B2 | 7/2012 | Blomquist |
| 8,221,356 B2 | 7/2012 | Enggaard et al. |
| 8,229,535 B2 | 7/2012 | Mensinger et al. |
| 8,231,531 B2 | 7/2012 | Brister et al. |
| 8,231,562 B2 | 7/2012 | Buck et al. |
| 8,237,715 B2 | 8/2012 | Buck et al. |
| 8,250,483 B2 | 8/2012 | Blomquist |
| D667,948 S | 9/2012 | Moldenhauer |
| 8,257,652 B2 | 9/2012 | Drucker et al. |
| 8,257,653 B2 | 9/2012 | Drucker et al. |
| 8,266,906 B2 | 9/2012 | Wu et al. |
| 8,273,296 B2 | 9/2012 | Drucker et al. |
| 8,279,226 B2 | 10/2012 | Krieftewirth |
| RE43,834 E | 11/2012 | Steenfeldt-Jensen et al. |
| 8,310,415 B2 | 11/2012 | Mclaughlin et al. |
| 8,333,752 B2 | 12/2012 | Veit et al. |
| 8,337,469 B2 | 12/2012 | Eberhart et al. |
| 8,357,091 B2 | 1/2013 | Say et al. |
| 8,365,065 B2 | 1/2013 | Gejdos et al. |
| 8,372,005 B2 | 2/2013 | Say et al. |
| 8,439,834 B2 | 5/2013 | Schmelzeisen-Redeker et al. |
| 8,444,595 B2 | 5/2013 | Brukalo et al. |
| 8,460,231 B2 | 6/2013 | Brauker et al. |
| 8,514,086 B2 | 8/2013 | Harper et al. |
| 8,529,838 B2 | 9/2013 | Drucker et al. |
| 8,529,839 B2 | 9/2013 | Drucker et al. |
| 8,529,841 B2 | 9/2013 | Drucker et al. |
| 8,551,039 B2 | 10/2013 | Veit et al. |
| 8,556,865 B2 | 10/2013 | Krulevitch et al. |
| 8,556,867 B2 | 10/2013 | Krulevitch et al. |
| 8,562,558 B2 | 10/2013 | Kamath et al. |
| 8,565,848 B2 | 10/2013 | Brister et al. |
| D694,252 S | 11/2013 | Scott |
| 8,579,815 B2 | 11/2013 | Galley et al. |
| 8,591,455 B2 | 11/2013 | Mensinger et al. |
| 8,601,005 B2 | 12/2013 | Bousamra et al. |
| 8,615,366 B2 | 12/2013 | Galley et al. |
| 8,622,906 B2 | 1/2014 | Say et al. |
| 8,657,779 B2 | 2/2014 | Blomquist |
| 8,663,109 B2 | 3/2014 | Brister et al. |
| 8,719,945 B2 | 5/2014 | Birtwhistle et al. |
| 8,721,585 B2 | 5/2014 | Brauker et al. |

(56) References Cited

U.S. PATENT DOCUMENTS

| | | |
|---|---|---|
| 8,738,925 B1 | 5/2014 | Park et al. |
| 8,743,662 B2 | 6/2014 | Sjolund et al. |
| 8,750,955 B2 | 6/2014 | Brister et al. |
| 8,756,074 B2 | 6/2014 | Brzustowicz |
| 8,761,940 B2 | 6/2014 | Long et al. |
| 8,774,887 B2 | 7/2014 | Say et al. |
| 8,808,228 B2 | 8/2014 | Brister et al. |
| 8,816,862 B2 | 8/2014 | Harper et al. |
| 8,817,258 B2 | 8/2014 | Whalley et al. |
| 8,821,452 B2 | 9/2014 | Dasbach et al. |
| 8,882,722 B2 | 11/2014 | Bode et al. |
| 8,882,741 B2 | 11/2014 | Brauker et al. |
| 8,895,315 B2 | 11/2014 | Batman et al. |
| 8,920,401 B2 | 12/2014 | Brauker et al. |
| 8,926,585 B2 | 1/2015 | Brauker et al. |
| 8,932,250 B2 | 1/2015 | Montgomery et al. |
| 8,961,465 B2 | 2/2015 | Blomquist |
| 8,992,464 B2 | 3/2015 | Bashan et al. |
| D727,928 S | 4/2015 | Allison et al. |
| 9,008,803 B2 | 4/2015 | Blomquist |
| 9,020,572 B2 | 4/2015 | Mensinger et al. |
| 9,022,996 B2 | 5/2015 | Eberhart et al. |
| 9,033,877 B2 | 5/2015 | Werner et al. |
| 9,041,730 B2 | 5/2015 | Johnson et al. |
| 9,050,409 B2 | 6/2015 | Haueter et al. |
| 9,050,413 B2 | 6/2015 | Brauker et al. |
| 9,072,477 B2 | 7/2015 | Say et al. |
| 9,089,650 B2 | 7/2015 | Nielsen et al. |
| 9,101,723 B2 | 8/2015 | Andre |
| 9,108,006 B2 | 8/2015 | Jensen et al. |
| D738,385 S | 9/2015 | Lim et al. |
| 9,125,991 B2 | 9/2015 | Schabbach et al. |
| 9,134,823 B2 | 9/2015 | Grant et al. |
| 9,136,939 B2 | 9/2015 | Galley et al. |
| 9,143,569 B2 | 9/2015 | Mensinger et al. |
| 9,155,843 B2 | 10/2015 | Brauker et al. |
| 9,159,148 B2 | 10/2015 | Boyer et al. |
| 9,186,113 B2 | 11/2015 | Harper et al. |
| 9,198,623 B2 | 12/2015 | Fern et al. |
| D747,333 S | 1/2016 | Supino et al. |
| D748,101 S | 1/2016 | Bang et al. |
| D748,126 S | 1/2016 | Sarukkai et al. |
| 9,233,210 B2 | 1/2016 | Bock et al. |
| D749,103 S | 2/2016 | Song |
| 9,250,111 B2 | 2/2016 | Whalley et al. |
| 9,255,830 B2 | 2/2016 | Whalley et al. |
| D753,685 S | 4/2016 | Zimmerman et al. |
| D754,689 S | 4/2016 | Lee |
| D759,684 S | 6/2016 | Bijlani et al. |
| 9,358,334 B2 | 6/2016 | Arefieg |
| D761,280 S | 7/2016 | Chung et al. |
| D763,308 S | 8/2016 | Wang et al. |
| D766,958 S | 9/2016 | Salazar et al. |
| 9,435,666 B2 | 9/2016 | Richter |
| 9,446,194 B2 | 9/2016 | Kamath et al. |
| 9,483,620 B2 | 11/2016 | Reimer |
| 9,498,155 B2 | 11/2016 | Brauker et al. |
| 9,501,219 B2 | 11/2016 | Yoshimoto et al. |
| 9,526,838 B2 | 12/2016 | Baran et al. |
| D777,760 S | 1/2017 | Zhao et al. |
| 9,545,482 B2 | 1/2017 | Binier |
| 9,561,324 B2 | 2/2017 | Estes |
| D781,890 S | 3/2017 | Gathman et al. |
| 9,604,004 B2 | 3/2017 | Jakobsen |
| D783,037 S | 4/2017 | Hariharan et al. |
| D783,648 S | 4/2017 | Vazquez et al. |
| D784,391 S | 4/2017 | Yuguchi et al. |
| D785,025 S | 4/2017 | Zimmerman et al. |
| 9,619,625 B2 | 4/2017 | Bengtsson |
| 9,623,188 B2 | 4/2017 | Nielsen et al. |
| 9,629,901 B2 | 4/2017 | Estes |
| D786,273 S | 5/2017 | Herman et al. |
| 9,636,461 B2 | 5/2017 | Bengtsson et al. |
| 9,636,464 B1 | 5/2017 | Binier |
| 9,638,564 B2 | 5/2017 | Whalley et al. |
| 9,642,968 B2 | 5/2017 | Whalley et al. |
| 9,649,448 B2 | 5/2017 | Madsen |
| 9,651,482 B2 | 5/2017 | Blei et al. |
| 9,672,328 B2 | 6/2017 | Saint et al. |
| 9,675,761 B2 | 6/2017 | Hoeholt et al. |
| D791,806 S | 7/2017 | Brewington et al. |
| D794,047 S | 8/2017 | Gandhi et al. |
| D795,900 S | 8/2017 | Bischoff et al. |
| D795,919 S | 8/2017 | Bischoff et al. |
| D795,927 S | 8/2017 | Bischoff et al. |
| 9,721,176 B2 | 8/2017 | Prager |
| 9,730,621 B2 | 8/2017 | Cohen et al. |
| 9,734,302 B2 | 8/2017 | Nielsen et al. |
| 9,737,665 B2 | 8/2017 | Heumann et al. |
| D797,760 S | 9/2017 | Tsujimura et al. |
| D798,312 S | 9/2017 | Tsujimura et al. |
| 9,750,882 B2 | 9/2017 | Blei et al. |
| 9,750,886 B2 | 9/2017 | Plambech et al. |
| 9,775,543 B2 | 10/2017 | Brister et al. |
| 9,782,543 B2 | 10/2017 | Groeschke et al. |
| 9,782,544 B2 | 10/2017 | Heumann et al. |
| 9,788,172 B1 | 10/2017 | Ewe et al. |
| 9,789,260 B1 | 10/2017 | Binier |
| 9,790,977 B2 | 10/2017 | Baran et al. |
| D802,760 S | 11/2017 | Neby |
| 9,833,576 B2 | 12/2017 | Windum et al. |
| 9,848,774 B2 | 12/2017 | Bergstrom et al. |
| D808,986 S | 1/2018 | Dudey |
| D809,544 S | 2/2018 | Ambielli |
| D809,545 S | 2/2018 | Ban et al. |
| D811,425 S | 2/2018 | Olsen et al. |
| D815,127 S | 4/2018 | Phillips et al. |
| D815,667 S | 4/2018 | Yeung |
| D819,043 S | 5/2018 | Yamaura et al. |
| 9,980,140 B1 | 5/2018 | Spencer et al. |
| D820,297 S | 6/2018 | Gardner et al. |
| 9,996,668 B2 | 6/2018 | Reihman et al. |
| 10,016,565 B2 | 7/2018 | Nielsen et al. |
| 10,043,093 B2 | 8/2018 | Allerdings et al. |
| 10,071,205 B2 | 9/2018 | Blei et al. |
| D831,049 S | 10/2018 | Agarwal et al. |
| D831,684 S | 10/2018 | Ghosh |
| D832,292 S | 10/2018 | Hu et al. |
| 10,086,141 B2 | 10/2018 | Steel et al. |
| 10,105,094 B2 | 10/2018 | Baran et al. |
| 10,105,497 B2 | 10/2018 | Dreier et al. |
| D832,870 S | 11/2018 | Hu |
| D833,469 S | 11/2018 | Coleman et al. |
| D834,710 S | 11/2018 | Michael |
| 10,117,996 B2 | 11/2018 | Stefansen |
| 10,117,999 B2 | 11/2018 | Andersen |
| 10,133,948 B2 | 11/2018 | Hammen |
| D835,118 S | 12/2018 | Lee et al. |
| 10,155,090 B2 | 12/2018 | Arsen et al. |
| 10,159,797 B2 | 12/2018 | Andersen et al. |
| 10,159,798 B2 | 12/2018 | Blei et al. |
| D837,807 S | 1/2019 | Baber et al. |
| D838,734 S | 1/2019 | Kruse et al. |
| 10,166,338 B2 | 1/2019 | Nielsen et al. |
| 10,166,340 B2 | 1/2019 | Blei et al. |
| 10,169,539 B2 | 1/2019 | Reihman et al. |
| 10,173,015 B2 | 1/2019 | Fiedler et al. |
| 10,179,207 B2 | 1/2019 | Haupt |
| 10,183,119 B2 | 1/2019 | Andersen et al. |
| 10,183,120 B2 | 1/2019 | Sihlanick et al. |
| 10,190,901 B2 | 1/2019 | Whalley et al. |
| 10,195,351 B2 | 2/2019 | Allerdings et al. |
| 10,195,352 B2 | 2/2019 | Baran et al. |
| 10,195,355 B2 | 2/2019 | Allerdings et al. |
| D842,888 S | 3/2019 | Krainer et al. |
| D843,402 S | 3/2019 | Casse et al. |
| D846,590 S | 4/2019 | Cabrera et al. |
| D847,165 S | 4/2019 | Kolbenheyer |
| D849,757 S | 5/2019 | Jing et al. |
| 10,296,128 B1 | 5/2019 | Nold et al. |
| 10,341,866 B1 | 7/2019 | Spencer et al. |
| 10,524,110 B1 | 12/2019 | Klem et al. |
| 10,667,759 B2 | 6/2020 | Duke et al. |
| 10,686,898 B1 | 6/2020 | Phillips et al. |

(56) References Cited

U.S. PATENT DOCUMENTS

| | | |
|---|---|---|
| 10,702,658 B2 | 7/2020 | Shekalim |
| 10,896,245 B2 | 1/2021 | Crothall et al. |
| 11,464,459 B2 | 10/2022 | Sjolund et al. |
| 2003/0028089 A1 | 2/2003 | Galley et al. |
| 2003/0032868 A1 | 2/2003 | Graskov et al. |
| 2003/0065536 A1 | 4/2003 | Hansen et al. |
| 2004/0039255 A1 | 2/2004 | Simonsen et al. |
| 2004/0062148 A1 | 4/2004 | Skyggebjerg et al. |
| 2004/0093331 A1 | 5/2004 | Garner et al. |
| 2004/0153257 A1 | 8/2004 | Munk |
| 2005/0005121 A1 | 1/2005 | Chen et al. |
| 2005/0038674 A1 | 2/2005 | Braig et al. |
| 2005/0049179 A1 | 3/2005 | Davidson et al. |
| 2005/0192557 A1 | 9/2005 | Brauker et al. |
| 2006/0036144 A1 | 2/2006 | Brister et al. |
| 2006/0173417 A1 | 8/2006 | Rosen et al. |
| 2007/0021715 A1 | 1/2007 | Kohlbrenner et al. |
| 2007/0173708 A9 | 7/2007 | Dobbles et al. |
| 2007/0186923 A1 | 8/2007 | Poutiatine et al. |
| 2007/0239486 A1 | 10/2007 | Gordon |
| 2008/0119705 A1 | 5/2008 | Patel et al. |
| 2008/0162192 A1 | 7/2008 | Vonk et al. |
| 2008/0188813 A1 | 8/2008 | Miller et al. |
| 2008/0201169 A1 | 8/2008 | Galasso et al. |
| 2008/0228057 A1 | 9/2008 | Graskov et al. |
| 2008/0234663 A1 | 9/2008 | Yodfat et al. |
| 2008/0235053 A1 | 9/2008 | Ray et al. |
| 2008/0262469 A1 | 10/2008 | Brister et al. |
| 2008/0287755 A1 | 11/2008 | Sass et al. |
| 2008/0300572 A1 | 12/2008 | Rankers et al. |
| 2008/0310676 A1 | 12/2008 | Silver |
| 2008/0312512 A1 | 12/2008 | Brukalo et al. |
| 2008/0312584 A1 | 12/2008 | Montgomery et al. |
| 2009/0036771 A1 | 2/2009 | Fago et al. |
| 2009/0048561 A1 | 2/2009 | Burren et al. |
| 2009/0103124 A1 | 4/2009 | Kimura et al. |
| 2009/0120716 A1 | 5/2009 | Yamamoto et al. |
| 2009/0131875 A1 | 5/2009 | Green |
| 2009/0144089 A1 | 6/2009 | Heywood et al. |
| 2009/0163793 A1 | 6/2009 | Koehler et al. |
| 2009/0171589 A1 | 7/2009 | Kovatchev |
| 2009/0209938 A1 | 8/2009 | Aalto-Setaelae |
| 2009/0240440 A1 | 9/2009 | Shurabura et al. |
| 2009/0299276 A1 | 12/2009 | Brauker et al. |
| 2009/0299279 A1 | 12/2009 | Richter |
| 2009/0318865 A1 | 12/2009 | Moeller et al. |
| 2010/0017141 A1 | 1/2010 | Campbell et al. |
| 2010/0049126 A1 | 2/2010 | Bronfeld et al. |
| 2010/0058060 A1 | 3/2010 | Schneider |
| 2010/0063438 A1 | 3/2010 | Bengtsson |
| 2010/0081993 A1 | 4/2010 | O'Connor |
| 2010/0095229 A1 | 4/2010 | Dixon et al. |
| 2010/0198520 A1 | 8/2010 | Breton et al. |
| 2010/0292634 A1 | 11/2010 | Kircher et al. |
| 2010/0305965 A1 | 12/2010 | Benjamin et al. |
| 2010/0331656 A1 | 12/2010 | Mensinger et al. |
| 2011/0009727 A1 | 1/2011 | Mensinger et al. |
| 2011/0124996 A1 | 5/2011 | Reinke et al. |
| 2011/0178462 A1 | 7/2011 | Moberg et al. |
| 2011/0184343 A1 | 7/2011 | Veit et al. |
| 2011/0191343 A1 | 8/2011 | Heaton et al. |
| 2011/0193704 A1 | 8/2011 | Harper et al. |
| 2011/0201911 A1 | 8/2011 | Johnson et al. |
| 2011/0270158 A1 | 11/2011 | Brauker et al. |
| 2011/0275986 A1 | 11/2011 | Bashan et al. |
| 2011/0281791 A1 | 11/2011 | Zion et al. |
| 2011/0282409 A1 | 11/2011 | Ternes et al. |
| 2011/0295215 A1 | 12/2011 | Nielsen et al. |
| 2011/0313350 A1 | 12/2011 | Krulevitch et al. |
| 2011/0313395 A1 | 12/2011 | Krulevitch et al. |
| 2012/0046606 A1 | 2/2012 | Arefieg |
| 2012/0072236 A1 | 3/2012 | Atkin |
| 2012/0078665 A1 | 3/2012 | Johnson et al. |
| 2012/0165746 A1 | 6/2012 | Harms et al. |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0238852 A1 | 9/2012 | Brauker et al. |
| 2012/0238853 A1 | 9/2012 | Arefieg |
| 2012/0271557 A1 | 10/2012 | Sekimoto et al. |
| 2012/0296311 A1 | 11/2012 | Brauker et al. |
| 2013/0004844 A1 | 1/2013 | Hosoe et al. |
| 2013/0030841 A1 | 1/2013 | Bergstrom et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0047084 A1 | 2/2013 | Sanders et al. |
| 2013/0171938 A1 | 7/2013 | Mears et al. |
| 2013/0184547 A1 | 7/2013 | Taub et al. |
| 2013/0184996 A1 | 7/2013 | Zivitz et al. |
| 2013/0197479 A1 | 8/2013 | Butler et al. |
| 2013/0211248 A1 | 8/2013 | Cowan et al. |
| 2013/0291116 A1 | 10/2013 | Homer |
| 2013/0298063 A1 | 11/2013 | Joy et al. |
| 2013/0310756 A1 | 11/2013 | Whalley et al. |
| 2013/0331659 A1 | 12/2013 | Koski et al. |
| 2013/0338453 A1 | 12/2013 | Duke et al. |
| 2014/0012117 A1 | 1/2014 | Mensinger et al. |
| 2014/0012118 A1 | 1/2014 | Mensinger et al. |
| 2014/0012510 A1 | 1/2014 | Mensinger et al. |
| 2014/0012511 A1 | 1/2014 | Mensinger et al. |
| 2014/0018733 A1 | 1/2014 | Sjoelund et al. |
| 2014/0019396 A1 | 1/2014 | Carlsgaard et al. |
| 2014/0025400 A1 | 1/2014 | Galley et al. |
| 2014/0058749 A1 | 2/2014 | Galley et al. |
| 2014/0068487 A1 | 3/2014 | Steiger et al. |
| 2014/0074041 A1 | 3/2014 | Pedersen et al. |
| 2014/0081662 A1 | 3/2014 | Bradrick et al. |
| 2014/0091941 A1 | 4/2014 | Johnson et al. |
| 2014/0094743 A1 | 4/2014 | Bengtsson |
| 2014/0113856 A1 | 4/2014 | Pohl et al. |
| 2014/0114161 A1 | 4/2014 | Kamath et al. |
| 2014/0128705 A1 | 5/2014 | Mazlish |
| 2014/0148659 A1 | 5/2014 | Sloan et al. |
| 2014/0187889 A1 | 7/2014 | Cohen et al. |
| 2014/0200426 A1 | 7/2014 | Taub et al. |
| 2014/0207080 A1 | 7/2014 | Allerdings |
| 2014/0257065 A1 | 9/2014 | Brister et al. |
| 2014/0276531 A1 | 9/2014 | Walsh |
| 2014/0288494 A1 | 9/2014 | Brister et al. |
| 2014/0297299 A1 | 10/2014 | Lester, IV |
| 2014/0309615 A1 | 10/2014 | Mazlish |
| 2014/0324020 A1 | 10/2014 | Stefansen |
| 2014/0371682 A1 | 12/2014 | Bengtsson et al. |
| 2015/0018770 A1 | 1/2015 | Baran et al. |
| 2015/0043410 A1 | 2/2015 | Chaturvedi et al. |
| 2015/0073337 A1 | 3/2015 | Saint et al. |
| 2015/0151050 A1 | 6/2015 | Estes |
| 2015/0164415 A1 | 6/2015 | Bashan et al. |
| 2015/0193595 A1 | 7/2015 | Mcnamara et al. |
| 2015/0202375 A1 | 7/2015 | Schabbach et al. |
| 2015/0202377 A1 | 7/2015 | Haupt |
| 2015/0205947 A1 | 7/2015 | Berman et al. |
| 2015/0246179 A1 | 9/2015 | Zur et al. |
| 2015/0260726 A1 | 9/2015 | Refvik |
| 2015/0289823 A1 | 10/2015 | Rack-Gomer et al. |
| 2015/0290396 A1 | 10/2015 | Nagar et al. |
| 2015/0306304 A1 | 10/2015 | Schabbach et al. |
| 2015/0350147 A1 | 12/2015 | Shepherd et al. |
| 2015/0351683 A1 | 12/2015 | Brauker et al. |
| 2015/0356273 A1 | 12/2015 | Cave |
| 2015/0359490 A1 | 12/2015 | Massey et al. |
| 2015/0359965 A1 | 12/2015 | O'Connor et al. |
| 2015/0365826 A1 | 12/2015 | Mancini et al. |
| 2016/0030673 A1 | 2/2016 | White et al. |
| 2016/0030679 A1 | 2/2016 | Nielsen et al. |
| 2016/0030680 A1 | 2/2016 | Veasey et al. |
| 2016/0030683 A1 | 2/2016 | Taylor et al. |
| 2016/0038675 A1 | 2/2016 | Estes et al. |
| 2016/0047685 A1 | 2/2016 | Blei et al. |
| 2016/0047743 A1 | 2/2016 | Blei et al. |
| 2016/0051760 A1 | 2/2016 | Krusell et al. |

(56) References Cited

U.S. PATENT DOCUMENTS

| | | |
|---|---|---|
| 2016/0065799 A1 | 3/2016 | Haupt et al. |
| 2016/0066843 A1 | 3/2016 | Mensinger et al. |
| 2016/0081632 A1 | 3/2016 | Kamath et al. |
| 2016/0082192 A1 | 3/2016 | Veasey et al. |
| 2016/0101232 A1 | 4/2016 | Kamath et al. |
| 2016/0101234 A1 | 4/2016 | Bock et al. |
| 2016/0106927 A1 | 4/2016 | Moeller et al. |
| 2016/0113558 A1 | 4/2016 | Bhavaraju et al. |
| 2016/0117481 A1 | 4/2016 | Booth et al. |
| 2016/0155081 A1 | 6/2016 | Legisa et al. |
| 2016/0213848 A1 | 7/2016 | Whalley et al. |
| 2016/0223380 A1 | 8/2016 | Whalley et al. |
| 2016/0235925 A1 | 8/2016 | Kuhn et al. |
| 2016/0263327 A1 | 9/2016 | Radmer et al. |
| 2016/0266752 A1 | 9/2016 | Wu et al. |
| 2016/0287804 A1 | 10/2016 | Madsen et al. |
| 2016/0287807 A1 | 10/2016 | Madsen et al. |
| 2016/0324463 A1 | 11/2016 | Simpson et al. |
| 2017/0053101 A1 | 2/2017 | Booth et al. |
| 2017/0053552 A1 | 2/2017 | Zhong et al. |
| 2017/0068799 A1 | 3/2017 | Mensinger et al. |
| 2017/0103175 A1 | 4/2017 | Chopra et al. |
| 2017/0106052 A1 | 4/2017 | Spat et al. |
| 2017/0124275 A1 | 5/2017 | Reihman et al. |
| 2017/0131993 A1 | 5/2017 | Salameh et al. |
| 2017/0132120 A1 | 5/2017 | Salameh et al. |
| 2017/0132392 A1 | 5/2017 | Gerken |
| 2017/0138769 A1 | 5/2017 | Jones et al. |
| 2017/0139974 A1 | 5/2017 | Javed et al. |
| 2017/0151390 A1 | 6/2017 | Muller-Pathle |
| 2017/0173261 A1 | 6/2017 | O'Connor et al. |
| 2017/0181645 A1 | 6/2017 | Mahalingam et al. |
| 2017/0181678 A1 | 6/2017 | Newberry |
| 2017/0182258 A1 | 6/2017 | Michael |
| 2017/0185283 A1 | 6/2017 | Bhavaraju et al. |
| 2017/0185284 A1 | 6/2017 | Bhavaraju et al. |
| 2017/0189615 A1 | 7/2017 | Estes |
| 2017/0189616 A1 | 7/2017 | Bengtsson et al. |
| 2017/0189625 A1 | 7/2017 | Cirillo et al. |
| 2017/0199985 A1 | 7/2017 | Mazlish et al. |
| 2017/0215811 A1 | 8/2017 | Newberry |
| 2017/0216518 A1 | 8/2017 | Davis et al. |
| 2017/0216524 A1 | 8/2017 | Haider et al. |
| 2017/0219486 A1 | 8/2017 | Blei et al. |
| 2017/0220751 A1 | 8/2017 | Davis et al. |
| 2017/0224922 A1 | 8/2017 | Lepple-Wienhues |
| 2017/0224927 A1 | 8/2017 | Windum et al. |
| 2017/0228518 A1 | 8/2017 | Booth et al. |
| 2017/0232203 A1 | 8/2017 | Krusell |
| 2017/0235919 A1 | 8/2017 | Bauss et al. |
| 2017/0235920 A1 | 8/2017 | Bauss et al. |
| 2017/0251982 A1 | 9/2017 | Koehler et al. |
| 2017/0266389 A1 | 9/2017 | Mcloughlin et al. |
| 2017/0270276 A1 | 9/2017 | Saint et al. |
| 2017/0270829 A1 | 9/2017 | Bauss |
| 2017/0286194 A1 | 10/2017 | Morris et al. |
| 2017/0286614 A1 | 10/2017 | Morris et al. |
| 2017/0286638 A1 | 10/2017 | Searle et al. |
| 2017/0304538 A1 | 10/2017 | Renstad et al. |
| 2017/0304541 A1 | 10/2017 | Bauss et al. |
| 2017/0304552 A1 | 10/2017 | Prager |
| 2017/0312446 A1 | 11/2017 | Kunz et al. |
| 2017/0316178 A1 | 11/2017 | Riedel et al. |
| 2017/0338864 A1 | 11/2017 | Rolsted et al. |
| 2017/0340808 A1 | 11/2017 | Andersen et al. |
| 2017/0340826 A1 | 11/2017 | Draper |
| 2017/0351842 A1 | 12/2017 | Booth et al. |
| 2017/0366617 A1 | 12/2017 | Mensinger et al. |
| 2017/0367627 A1 | 12/2017 | Brister et al. |
| 2017/0368263 A1 | 12/2017 | Ploch |
| 2017/0368265 A1 | 12/2017 | Groeschke et al. |
| 2018/0001027 A1 | 1/2018 | Klemm et al. |
| 2018/0008773 A1 | 1/2018 | Hautaviita et al. |
| 2018/0008778 A1 | 1/2018 | Erbstein |
| 2018/0008779 A1 | 1/2018 | Hautaviita et al. |
| 2018/0028759 A1 | 2/2018 | Riedel et al. |
| 2018/0028760 A1 | 2/2018 | Gugl et al. |
| 2018/0036484 A1 | 2/2018 | Andersen |
| 2018/0036495 A1 | 2/2018 | Searle et al. |
| 2018/0042559 A1 | 2/2018 | Cabrera et al. |
| 2018/0043104 A1 | 2/2018 | Mueller-Pathle |
| 2018/0050157 A1 | 2/2018 | Whalley et al. |
| 2018/0060008 A1 | 3/2018 | Bender et al. |
| 2018/0060529 A1 | 3/2018 | Crothall et al. |
| 2018/0064879 A1 | 3/2018 | Sall et al. |
| 2018/0085532 A1 | 3/2018 | Desborough et al. |
| 2018/0099084 A1 | 4/2018 | Schabbach et al. |
| 2018/0103879 A1 | 4/2018 | Masciotti et al. |
| 2018/0121630 A1 | 5/2018 | Portnoy |
| 2018/0147362 A1 | 5/2018 | Arenas et al. |
| 2018/0154086 A1 | 6/2018 | Toporek et al. |
| 2018/0161505 A1 | 6/2018 | Prager |
| 2018/0185587 A1 | 7/2018 | Brauker et al. |
| 2018/0217917 A1 | 8/2018 | Hayter et al. |
| 2018/0221582 A1 | 8/2018 | Klemm et al. |
| 2018/0224315 A1 | 8/2018 | Schabbacha et al. |
| 2018/0226150 A1 | 8/2018 | Hayter et al. |
| 2018/0228977 A1 | 8/2018 | Schabbach et al. |
| 2018/0236172 A1 | 8/2018 | Schabbach et al. |
| 2018/0236185 A1 | 8/2018 | Sall et al. |
| 2018/0243504 A1 | 8/2018 | Scott et al. |
| 2018/0262578 A1 | 9/2018 | Shaw et al. |
| 2018/0268236 A1 | 9/2018 | Klemm |
| 2018/0272072 A1 | 9/2018 | Radmer et al. |
| 2018/0277246 A1 | 9/2018 | Zhong et al. |
| 2018/0289901 A1 | 10/2018 | Bggild-Damkvist et al. |
| 2018/0296767 A1 | 10/2018 | Sall |
| 2018/0303417 A1 | 10/2018 | Mensinger et al. |
| 2018/0304028 A1 | 10/2018 | Riedel |
| 2018/0326164 A1 | 11/2018 | Bauss et al. |
| 2018/0339113 A1 | 11/2018 | Wendland et al. |
| 2018/0341826 A1 | 11/2018 | Allerdings et al. |
| 2018/0353694 A1 | 12/2018 | Riedel et al. |
| 2018/0353698 A1 | 12/2018 | Saint et al. |
| 2018/0353699 A1 | 12/2018 | Helmer et al. |
| 2018/0353700 A1 | 12/2018 | Sall et al. |
| 2018/0361067 A1 | 12/2018 | Sall et al. |
| 2018/0361076 A1 | 12/2018 | Klemm et al. |
| 2018/0361082 A1 | 12/2018 | Sall et al. |
| 2018/0368683 A1 | 12/2018 | Hu et al. |
| 2018/0369479 A1 | 12/2018 | Hayter et al. |
| 2018/0369488 A1 | 12/2018 | Carlsson et al. |
| 2018/0369490 A1 | 12/2018 | Rehbein et al. |
| 2019/0001060 A1 | 1/2019 | Gylleby et al. |
| 2019/0001069 A1 | 1/2019 | Carlsson et al. |
| 2019/0009032 A1 | 1/2019 | Hautaviita et al. |
| 2019/0015020 A1 | 1/2019 | Brister et al. |
| 2019/0015596 A1 | 1/2019 | Saint et al. |
| 2019/0022320 A1 | 1/2019 | Carlsson et al. |
| 2019/0029590 A1 | 1/2019 | Baran et al. |
| 2019/0030250 A1 | 1/2019 | Steel et al. |
| 2019/0035500 A1 | 1/2019 | Saint et al. |
| 2019/0036688 A1 | 1/2019 | Wasily et al. |
| 2019/0076070 A1 | 3/2019 | Nogueira et al. |
| 2019/0125224 A1 | 5/2019 | Kamath et al. |
| 2019/0125969 A1 | 5/2019 | Montgomery et al. |
| 2019/0132801 A1 | 5/2019 | Kamath et al. |
| 2019/0149887 A1 | 5/2019 | Williams et al. |
| 2019/0173885 A1 | 6/2019 | Kamath et al. |
| 2019/0175833 A1 | 6/2019 | Sjolund et al. |
| 2019/0175841 A1 | 6/2019 | Sjolund et al. |
| 2019/0183434 A1 | 6/2019 | Sjolund et al. |
| 2019/0184091 A1 | 6/2019 | Sjolund et al. |
| 2019/0184092 A1 | 6/2019 | Sjolund et al. |
| 2019/0184093 A1 | 6/2019 | Sjolund et al. |
| 2019/0184094 A1 | 6/2019 | Sjolund et al. |
| 2019/0184107 A1 | 6/2019 | Sjolund et al. |
| 2019/0184108 A1 | 6/2019 | Sjolund et al. |
| 2019/0184109 A1 | 6/2019 | Sjolund et al. |
| 2019/0184111 A1 | 6/2019 | Sjolund et al. |
| 2019/0192071 A1 | 6/2019 | Taub et al. |
| 2019/0237181 A1 | 8/2019 | Steinberg |
| 2019/0239825 A1 | 8/2019 | Kumar et al. |
| 2019/0274598 A1 | 9/2019 | Scott et al. |

(56) References Cited

U.S. PATENT DOCUMENTS

| | | |
|---|---|---|
| 2019/0282141 A1 | 9/2019 | Causey et al. |
| 2020/0016336 A1 | 1/2020 | Patek et al. |
| 2020/0205724 A1 | 7/2020 | Lee et al. |
| 2020/0350052 A1 | 11/2020 | Saint et al. |
| 2020/0360794 A1 | 11/2020 | Intonato et al. |

FOREIGN PATENT DOCUMENTS

| | | |
|---|---|---|
| CN | 103443798 A | 12/2013 |
| CN | 103957961 A | 7/2014 |
| CN | 104411349 A | 3/2015 |
| CN | 104797282 A | 7/2015 |
| CN | 105377118 A | 3/2016 |
| CN | 107073207 A | 8/2017 |
| EP | 0298067 A1 | 1/1989 |
| EP | 0513128 A1 | 11/1992 |
| EP | 0927057 A1 | 7/1999 |
| EP | 1571582 A2 | 9/2005 |
| EP | 1680175 | 7/2006 |
| EP | 2401011 | 1/2012 |
| EP | 2572740 A1 | 3/2013 |
| EP | 2767297 A2 | 8/2014 |
| EP | 2911717 | 9/2015 |
| EP | 2926846 A1 | 10/2015 |
| EP | 3049132 A1 | 8/2016 |
| EP | 2879740 B1 | 3/2017 |
| EP | 3167393 A2 | 5/2017 |
| EP | 2797660 B1 | 10/2019 |
| JP | 2014-514046 A | 6/2014 |
| JP | 2014-531283 A | 11/2014 |
| JP | 2015-178044 A | 10/2015 |
| JP | 2016-515452 A | 5/2016 |
| JP | 2016-517601 A | 6/2016 |
| JP | 6058673 B2 | 1/2017 |
| WO | 85/02544 A1 | 6/1985 |
| WO | 91/10460 A1 | 7/1991 |
| WO | 96/38190 A1 | 12/1996 |
| WO | 98/10813 A1 | 3/1998 |
| WO | 2005/046559 A2 | 5/2005 |
| WO | 2010/037828 A1 | 4/2010 |
| WO | 2010/052275 A2 | 5/2010 |
| WO | 2010/056718 A2 | 5/2010 |
| WO | 2010/098927 A1 | 9/2010 |
| WO | 2011/041007 A1 | 4/2011 |
| WO | 2011/091238 A1 | 7/2011 |
| WO | 2012/046199 A1 | 4/2012 |
| WO | 2013/004844 A1 | 1/2013 |
| WO | 2013/037754 A2 | 3/2013 |
| WO | 2013/053695 A1 | 4/2013 |
| WO | 2013/177135 A1 | 11/2013 |
| WO | 2014/029621 A1 | 2/2014 |
| WO | 2014/064691 A2 | 5/2014 |
| WO | 2014/020010 A2 | 6/2014 |
| WO | 2014/128157 A1 | 8/2014 |
| WO | 2014/145049 A2 | 9/2014 |
| WO | 2015/047870 A1 | 4/2015 |
| WO | 2015/169814 A1 | 11/2015 |
| WO | 2015/185686 A1 | 12/2015 |
| WO | 2016/004210 A1 | 1/2016 |
| WO | 2016/019192 A1 | 2/2016 |
| WO | 2016/007935 A3 | 4/2016 |
| WO | 2016/071912 A1 | 5/2016 |
| WO | 2016/116853 A1 | 7/2016 |
| WO | 2016/151973 A1 | 9/2016 |
| WO | 2017/123525 A1 | 7/2017 |
| WO | 2017/123523 A1 | 8/2017 |
| WO | 2017/132557 A1 | 8/2017 |
| WO | 2017/132577 A1 | 8/2017 |
| WO | 2018/064222 A1 | 4/2018 |

OTHER PUBLICATIONS

Baker, New Technologies for Diabetes, Mar. 25, 2017, XP055568829, 76, https://diabetes-education.com/wp-content/uploads/2017/03/Baker-HCP3.pdf.

Hu et al., An Improved PID Algorithm Based on Insulin-on-Board Estimate for Blood Glucose Control with Type 1 Diabetes, Jan. 1, 2015, Computational and Mathematical Methods in Medicine, 1-8, 2015.

Near Field Communication versus Bluetooth, Jan. 3, 2016, NearFieldCommunication.org via web.archive.org (Year: 2016).

Sara Krugman, Bionic Pancreas User Interface (3/4): Interface Details, Tidepool.org, Jul. 20, 2015.

T:slimx2 Insulin Pump User Guide, Tandem Diabetes Care, Jul. 22, 2016.

White, Common Sensing, May 2, 2017, XP055568837, 15, Mar. 13, 2019.

Cision PR News Wire, "Companion Medical Announces Insights by InPen, the Future of MDI Reports", Jun. 20, 2018.

Chinese First Office Action and Search Report for Chinese Application No. 201880080537.X, dated Apr. 27, 2023, 53 pages with translation.

Chinese First Office Action and Search Report for Chinese Application No. 201880080699.3, dated May 11, 2023, 47 pages with translation.

Communication pursuant to Article 94(3) EPC for European Patent Application No. 18 852 783.2, dated Jun. 22, 2023, 9 pages.

European Communication pursuant to Article 94(3) EPC for European Application No. 18839959, dated Apr. 4, 2023, 6 pages.

European Communication pursuant to Article 94(3) EPC for European Application No. 18839960.4, dated May 26, 2023, 6 pages.

European Examination Report for EP Application No. 18840106.1, dated Mar. 24, 2023, 14 pages.

European Search Report and Search Opinion Received for EP Application No. 21212980.3, dated Jul. 7, 2022, 10 pages.

Hu et al., An Improved PID Algorithm Based on Insulin-on-Board Estimate for Blood Glucose Control with Type 1 Diabetes, Jan. 1, 2015, Computational and Mathematical Methods in Medicine, pp. 1-8, 2015.

Indian Patent Examination Report for Indian Application No. 202027023258 dated May 19, 2022, 6 pages with English translation.

Japanese Notice of Reasons for Refusal for Japanese Patent Application No. 2020-551774, dated Dec. 4, 2023, 14 pages with English translation.

Australian Patent Examination Report No. 1 for Australian Application No. 2018383743, dated Oct. 23, 2023, 5 pages.

Chinese Second Office Action for Chinese Application No. 201880080537.X, dated Nov. 10, 2023, 44 pages with translation.

Japanese Notice of Reasons for Rejection for Japanese Application No. 2020-551774, dated Sep. 25, 2023, 6 pages with translation.

Australian Patent Examination report No. 1 for Australian Patent Application No. 2018383731, dated Oct. 17, 2023, 6 pages.

Chinese Second Office Action for Chinese Application No. 201880080699.3, dated Dec. 25, 2023, 33 pages with English machine translation.

| Sliding Scale Inputs | |
|---|---|
| Target Range Lower Limit Or Glucose Goal Start | 93 |
| Sensitivity Increment | 36 |

| Generated Sliding Scale Correction Chart | |
|---|---|
| Glucose Between mg/dl | Dose Adjustment (Units Of Insulin) |
| 21 – 56 | -2 |
| 57 – 92 | -1 |
| 93 – 128 | 0 |
| 129 – 164 | 1 |
| 165 – 200 | 2 |
| 201 – 236 | 3 |
| 237 – 272 | 4 |
| 273 – 308 | 5 |
| 309 – 344 | 6 |

*FIG. 26*

| Example Of Glucose Pattern Alone | Example Of Glucose Pattern + Guidance Note |
|---|---|
| "Bigfoot Notices That Your Glucose After Lunch Has Been High Three Times This Week." | "Bigfoot Notices That Your Glucose After Lunch Has Been High Three Times This Week." Consider If A Change In Insulin Is Needed. |
| "Factors That May Lead To High Glucose After A Meal Include Timing Or Injections, What Insulin Is Already Working, And Estimating Insulin Doses." | "Factors That May Lead To High Glucose After A Meal Include Timing Or Injections, What Insulin Is Already Working, And Estimating Insulin Doses." |

*FIG. 31*

INSULIN INJECTION ASSISTANCE SYSTEMS, METHODS, AND DEVICES

CROSS-REFERENCE TO RELATED APPLICATIONS

This application is a continuation of U.S. patent application Ser. No. 16/218,212, filed Dec. 12, 2018, now U.S. Pat. No. 11,083,852, issued Aug. 10, 2021, which claims the benefit of the filing date of U.S. Provisional Patent Application Ser. No. 62/682,878, filed Jun. 9, 2018, for "Insulin Injection Assistance Systems, Methods, and Devices"; of U.S. Provisional Patent Application Ser. No. 62/597,809 filed Dec. 12, 2017, for "Medicine Injection and Disease Management Systems, Devices, and Methods"; of U.S. Provisional Patent Application Ser. No. 62/597,868, filed Dec. 12, 2017, for "Therapy Assist Information and/or Tracking Device and Related Methods and Systems"; and of U.S. Provisional Patent Application Ser. No. 62/628,808, filed Feb. 9, 2018, for "Diabetes Therapy Management Systems, Methods and Devices," the disclosure of each of which is hereby incorporated herein in its entirety by this reference.

TECHNICAL FIELD

This disclosure relates to therapy management systems, methods, and devices adapted to collect and/or transmit data relating to therapy (e.g., the timing of therapy) and/or other therapy related data and to provide a user with therapy recommendations. In particular embodiments, diabetes therapy management systems, devices, and methods are disclosed, which may be utilized with insulin injection devices, including components adapted to provide a user with insulin therapy recommendations based on stored therapy parameters, blood glucose data, meal size estimations, and/or other parameters.

BACKGROUND

Diabetes mellitus is a chronic metabolic disorder caused by the inability of a person's pancreas to produce sufficient amounts of the hormone insulin such that the person's metabolism is unable to provide for the proper absorption of sugar and starch. This failure leads to hyperglycemia, i.e., the presence of an excessive amount of glucose within the blood plasma. Persistent hyperglycemia has been associated with a variety of serious symptoms and life-threatening long-term complications such as dehydration, ketoacidosis, diabetic coma, cardiovascular diseases, chronic renal failure, retinal damage and nerve damages with the risk of amputation of extremities. Because healing is not yet possible, a permanent therapy is necessary that provides constant glycemic control in order to constantly maintain the level of blood analyte within normal limits. Such glycemic control is achieved by regularly supplying external drugs to the body of the patient to thereby reduce the elevated levels of blood analyte.

An external biologically effective drug (e.g., insulin or its analog) is commonly administered by means of daily injections. In some cases, multiple, daily injections (MDI) of a mixture of rapid- and long-acting insulin via a reusable transdermal liquid dosing device (commonly referred to as an "insulin pen") or a hypodermic syringe. The injections are typically administered by a person with diabetes (PWD), and so require self-monitoring of blood glucose and the self-administration of insulin. The PWD that manages their care using MDI often plans insulin injections for each day, in advance, based on basal insulin requirement as well as external factors such as meals, exercise, sleep, etc. A typical dosing plan will include the time of day for an injection, the type of insulin (e.g., fast acting, long acting, a mixture of fast acting and long acting, etc.), and amount of insulin for each dose. In addition, PWDs will self-monitor their blood glucose and self-administer "bolus" dose(s) of rapid-acting insulin if their blood glucose is too high or consume carbohydrates (or sometimes administer glycogen) if their blood glucose is too low.

The "correct" insulin dose is a function of the level of glucose in the blood, physiological factors such as a person's insulin sensitivity, and lifestyle factors such as meals (e.g., recently consumed carbohydrates that have yet to be metabolized into glucose and absorbed into the blood). Moreover, even with careful planning and self-monitoring, a PWD may skip doses, double dose, and dose the wrong amount and/or type of insulin. Insufficient insulin can result in hyperglycemia, and too much insulin can result in hypoglycemia, which can result in clumsiness, trouble talking, confusion, loss of consciousness, seizures, or death. Accordingly, PWDs face a considerable cognitive burden in determining appropriate doses of insulin.

In order to assist with self-treatment, some diabetes treatment devices (e.g., blood glucose meters, insulin pumps, etc.) are equipped with insulin bolus calculators that have the user input an estimate (e.g., numerical estimate) of the quantity of carbohydrates consumed or about to be consumed (or additionally or alternatively protein, fat, or other meal data) and the bolus calculator outputs a recommended size for the insulin bolus dosage. Although bolus calculators remove some of the mental calculations that need to be made by the user in determining an appropriate insulin bolus dosage, bolus calculators still burden the user with the mental task of evaluating the constituents of their meal, may require the use of a secondary device, and often require manual entry of data. Accordingly, there is a need for methods, systems, and devices that assist the user to make appropriate therapy decisions while minimizing the burdens (e.g., data entry, mental calculations, procedures, etc.) on the user.

BRIEF DESCRIPTION OF THE DRAWINGS

The present disclosure may be understood more fully by reference to the following detailed description of example embodiments, which are illustrated in the accompanying figures.

FIG. 26 depicts an example sliding scale chart of a diabetes management system according to embodiments of the present disclosure.

FIGS. 27 through 33 illustrate example displays and/or user interfaces of a portion of the system (e.g., of the mobile device) according to embodiments of the present disclosure.

DETAILED DESCRIPTION

Figure 1A:
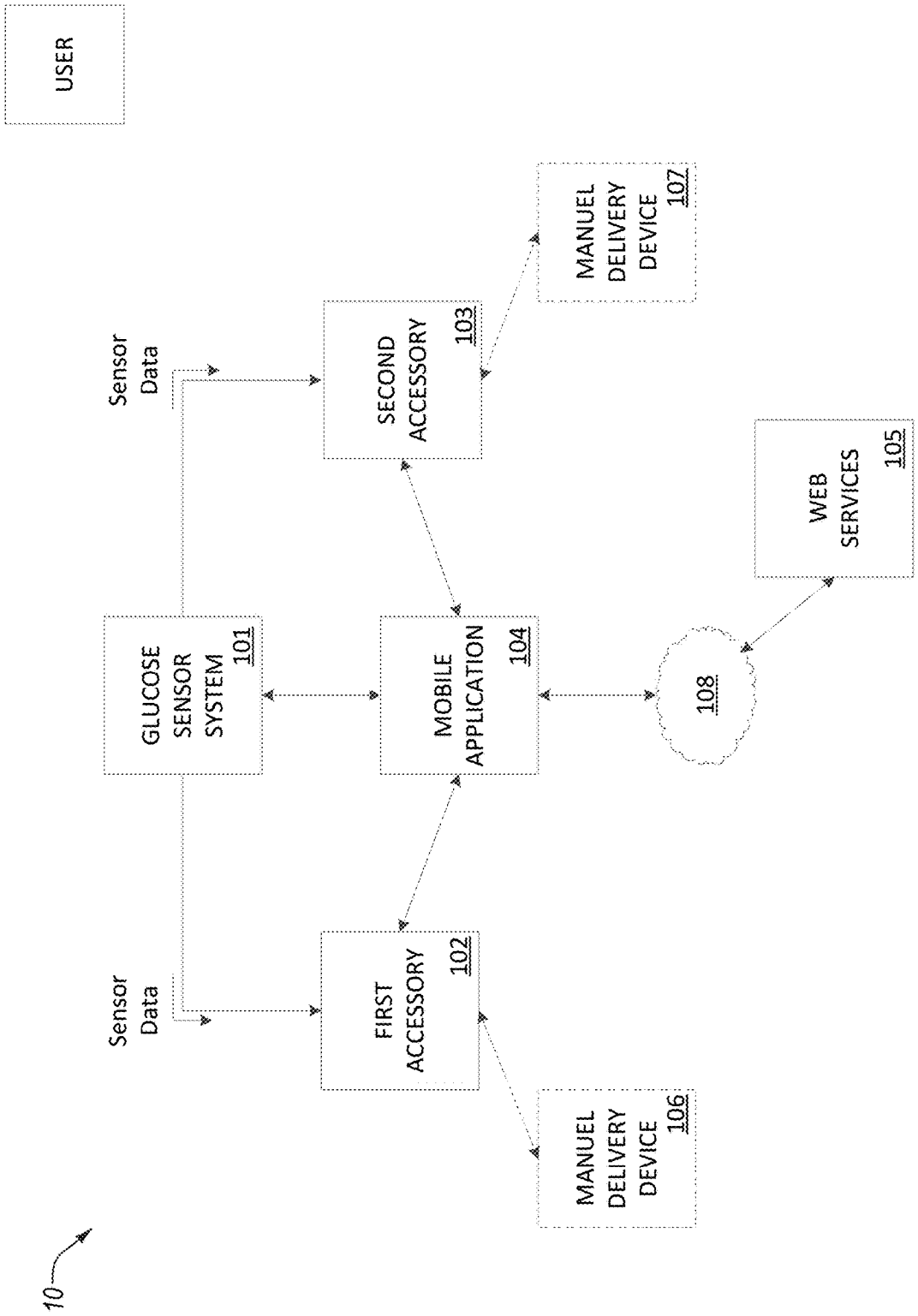
FIG. 1A illustrates a diabetes management system according to embodiments of the present disclosure.

Manual insulin delivery devices such as insulin pens, insulin inhalers, etc., (referred to herein, generally, as "manual insulin devices") provide a convenient, reusable means of delivering insulin. The improper dosing of insulin, however, due to human error, malfunction of an insulin pen, skipping doses, double dosing, and incorrect dosing, is always a concern. Although methods, devices, and systems provided herein are described for the delivery of insulin, collection of blood glucose data, and/or the treatment of diabetes, methods, devices, and systems provided herein may be adapted for the delivery of other medications, the collection of other analyte data, and/or the treatment of other diseases. Additionally, although methods, devices, and systems provided herein are described primarily by describing features and functionalities included in pen cap accessory for insulin delivery pens or methods the use pen cap accessories, or systems including pen cap accessories, the features discussed herein are also contemplated as being incorporated directly into smart medication delivery pens or smart medication delivery inhalers, other accessories adapted to be secured to or used with other manual medication delivery devices, or methods or systems including such smart medication delivery devices or smart accessories.

Systems, devices, and methods described herein may be operated or performed, respectively, by a user for example, a PWD, a patient, a test subject, a healthcare professional, clinician and a caregiver. Unless otherwise stated, the terms health care professional, clinician, and a caregiver are used interchangeably in this disclosure.

In general, the embodiments of therapy management systems (e.g., diabetes management systems such as insulin therapy management systems), methods, and devices described herein may include user interfaces configured to receive user-specific dosage parameters from a user or healthcare professional and use those user-specific dosage parameters to provide recommendations and reports to a user. In some embodiments, a user interface for receiving user-specific dosage parameters may be incorporated into a mobile application or another computing device and a user interface for displaying an immediate medication delivery recommendation may be incorporated into an accessory for a manual medication delivery device or a smart manual medication delivery device. In some cases, a user interface for entering user-specific dosage parameters can additionally be used for viewing reports, recommendations, alarms, alerts, notifications, recommended user-dosage parameter changes.

Systems, devices, and methods provided herein can include a user interface that is adapted to simplify the entry of therapy relevant data to ease the burden of self-treatment. In some embodiments, systems, devices, and methods provided herein are adapted to assist a person with diabetes (PWD) or their caregiver in determining an appropriate dosage of insulin. In some embodiments, methods, devices, and systems provided herein can reduce or eliminate the manual entry of numerical data after an initial setup. In some embodiments, methods, devices, and systems provided herein may be adapted to simplify the monitoring of blood glucose levels. In some embodiments, methods, devices, and systems provided herein can permit a user to discreetly manage their therapy. In some embodiments, methods, devices, and systems provided herein can reduce the cognitive burden associated with making daily therapy decisions.

Systems, devices and methods provided herein can simplify the process for obtaining insulin therapy suggestions and/or simplifying the collection of estimated glucose values (EGVs) and/or insulin delivery data from one or more insulin delivery devices. Systems, devices, and methods provided herein may be designed to minimize the changes that persons with diabetes (PWDs) that administer insulin therapy using injections may be required to make to their therapy/daily routines in order to receive therapy recommendations and/or to receive notifications, alerts, or alarms.

In some embodiments, systems, methods, and devices provided herein can give a user options of when, where, and whether to receive notifications, alerts or alarms, which may be, at least in part, based upon the devices of the system being carried by the user. In some embodiments, the alarms and/or alerts may be customized over time based on feedback from the user (e.g., likes and dislikes from the user). In some embodiments, systems, methods, and devices provided herein can include notifications, alerts, and/or alarms that use a combination of EGV data and insulin delivery data to determine whether to trigger the notification, alert, and/or alarm.

In some embodiments, systems, devices, and methods provided herein can automatically capture insulin delivery data, which may be captured using a connected and/or smart insulin injection pen or a connected and/or smart insulin pen accessory (e.g., a connected pen cap accessory).

In some embodiments, systems, devices, and methods provided herein can recommend insulin doses (e.g., dosages of long-acting and/or rapid-acting insulin) using any suitable technique. In some embodiments, recommended insulin dosages may be based upon blood glucose data (e.g., current EGV from continuous glucose monitor ("CGM"), flash glucose monitor, blood glucose meter, or any other sensor, blood glucose trend data, etc.), insulin administration data (bolus dosage amounts of rapid-acting insulin, dosages of long-acting insulin, dosage times, calculation of Insulin-on-Board ("IOB") and/or active insulin, etc.), meal data (mealtimes, user estimated carbohydrates, user estimated meal categorizations, user estimated glycemic impact of meal user meal history, user meal trends, etc.), and/or one or more insulin deliver parameters (e.g., total daily dose of basal insulin or long-acting insulin, carbohydrate-to-insulin ratio (CR), insulin sensitivity factor (ISF), etc.). Methods, devices and systems provided herein can, in some embodiments, adjust insulin delivery parameters over time based on glucose data and/or insulin administration data.

Systems, devices, and methods provided herein can include or use a mobile device (e.g., a mobile application running on a smartphone or tablet) to permit the user to setup the device or system, to check status of the device or system, adjust therapy settings, and/or learn about how to improve their therapy choices. In some embodiments, a mobile device can include information about maintenance tasks (e.g., reminders to conduct certain maintenance tasks). In some embodiments, methods, systems, and devices provided herein can detect patterns in therapy relevant data and use that data to provide a user with tips, suggestions, alerts, and/or alarms based on the patterns, which may be displayed on a mobile device. In some embodiments, a mobile device may provide a user with graphical displays regarding the user's therapy relevant data and/or therapy decisions (e.g., blood glucose data and/or insulin injection times). In some embodiments, a mobile device may provide a user with an indication that the user might want to adjust their therapy (e.g., an amount of insulin for meals, an amount of insulin for the user's basal requirements, a timing of their insulin injections, etc.) and provide the user with a mechanism (e.g., a link) to make adjustments to their therapy. In some embodiments, a mobile device may provide a user with an indication that the system has automatically adjusted their therapy (e.g., an amount of insulin for meals, an amount of insulin for the user's basal requirements, a timing of their insulin injections, etc.) and optionally provide the user with a mechanism (e.g., a link) to reject the automatic adjustment, confirm the automatic adjustment, or make a manual therapy adjustment.

In some embodiments, diabetes management systems, devices, and methods provided herein can include a plurality of meal size categories (e.g., three meal sizes (Small, Medium, Large), time-based meals (Breakfast, Lunch, Dinner, Snack)) that may be set by the user (e.g., on a mobile device). In some embodiments, a mobile device includes a setup user interface where a user is prompted to enter the user's typical insulin dosage for differently sized meals (e.g., a dose for a small meal, a dose for a medium meal, a dose for a large meal). In some embodiments, the setup user interface displays to the user example pictures of meals that would be considered to be within each meal category. In some embodiments, the device may analyze the approximate size of the meal for the user (e.g., by analyzing an input from the user, such as an input relating to characteristics of the meal, a picture of the meal, etc.). In some embodiments, the setup user interface may provide estimates of what the user is expected to enter for each meal size based on the user's entered amount of long-acting insulin (e.g., dosage of LANTUS®).

Systems, devices, and methods provided herein can include, use, or communicate with one or more accessories for a medication delivery device, such as an insulin pen (e.g., a pen cap for the insulin pen) that is (a) adapted to be secured to an injection pen and detect when the pen cap is secured to and/or released from the injection pen, (b) adapted to receive blood glucose data from a glucose sensor, and/or (c) adapted to provide therapy relevant information and/or recommendations to the user.

In some cases, the accessory may be a pen cap accessory adapted to detect pen capping information. Pen capping information (e.g., information about when the pen cap is secured to and/or released from the injection pen) can include information about a current capping period (e.g., the time since the last capping), information about a duration of one or more uncappings (which may also be referred to herein as "decapping(s)"), and the timing (e.g., time-of-day or time elapsed since) of each uncapping and each capping. In some embodiments, pen capping information may be displayed on the pen cap accessory to a user. In some embodiments, pen capping information may be announced by a speaker in the pen cap. For example, in some embodiments, a pen cap may provide a timer clock that counts up from the last time the pen cap was secured to the injection pen. In some embodiments, a pen cap accessory can wirelessly communicate pen capping information to a remote computing device (e.g., a smartphone, tablet, etc.). In some embodiments that do not include pen cap accessories, the accessories or smart delivery devices can detect other events associated with medication delivery actions and use that information in ways that pen capping information is described herein. For example, in some cases an injection pen accessory may be secured to an injection pen such that it can detect the mechanical movement of the dosing mechanism to determine a time of a dose of medication.

Pen capping information may be used to modify the user experience (e.g., the display or information presented to the user). In some embodiments, the pen cap adjusts the presentation of the therapy relevant information and/or recommendations provided to the user based on the pen capping information. For example, in some embodiments, a pen cap may provide bolus recommendations to correct for elevated blood glucose levels based on data from a glucose sensor, but may limit the presentation of such correction bolus recommendations to time periods when the current pen capping duration is greater than a threshold period of time (e.g., at least 2 hours, at least 3 hours, at least 4 hours, or at least 5 hours). In some embodiments, the pen cap may provide notifications, alerts, or alarms to the user based on the pen capping information. For example, if the pen cap is removed from the injection pen within a threshold period of time (e.g., within 30 minutes or 1 hour) from a previous capping, the pen cap may provide a visual, audible, or vibrational notification to indicate that the user may have recently used the pen to administer insulin. In some embodiments, the pen cap may be in wireless communication with a mobile computing device (e.g., a smartphone, tablet) and one or more notifications, alerts, or alarms based on pen capping information may be announced or displayed on the mobile computing device.

Pen capping information may be stored, displayed, and/or analyzed in combination with glucose data to determine user behaviors, such as, for example, whether the person is appropriately dosing insulin for meals and/or to correct elevated blood glucose levels. In some embodiments, pen capping information may be presented on a graphical representation of blood glucose data for the user and presented to a user and/or to a healthcare professional. In some embodiments, blood glucose data from a period of time after each capping event may be evaluated to determine whether the user appropriately dosed insulin for that capping event, e.g., appropriate dose, under dose, or overdose.

In some embodiments, a pen capping event may be disregarded where other information indicates that a dose was not provided. For example, where no change in the dosage selection of the insulin pen (e.g., a dial) was detected, the event may be disregarded. In some embodiments, a pen uncapping and recapping event may be disregarded if the total uncapping time is less than a first threshold (e.g., 4-6 seconds). For example, the threshold may be determined by setting it at an amount of time too short to permit for an injection, but long enough to allow a user to check the end of the pen to see if there is insulin remaining or if there is a needle attached to the pen. In some cases, the total decapping time (the time between an uncapping event and the subsequent recapping) for a decapping event may be analyzed in combination with blood glucose data to determine if there was an injection during that decapping event. In some cases, if the total decapping time exceeds a second threshold period of time (e.g., at least 15 minutes, at least 30 minutes, etc.), blood glucose data may be used to determine an approximate time of an injection.

Accessories provided herein (e.g., pen caps), and associated methods and systems provided herein, may be adapted to obtain blood glucose data for use in providing therapy relevant information and/or therapy recommendations via the accessory (e.g., via a pen cap). In some embodiments, the therapy relevant information displayed on a pen cap accessory can include a current estimated glucose value (EGV) for the user. In some embodiments, the therapy relevant information displayed on the pen cap can include a current blood glucose trend or rate of change indicator (e.g., a trend arrow). In some embodiments, the pen cap can include a recommended dose, which may be based on glucose data or may be based on stored parameters without consideration of the current EGV.

Accessories provided herein (e.g., pen caps) may be adapted to receive blood glucose data from any suitable glucose sensor. In some embodiments, the glucose sensor may be a continuous glucose monitor (CGM), a flash glucose monitor, a blood glucose meter (BGM), or any other suitable sensor. In the case of CGMs and flash glucose monitors, they may be configured to provide glucose data based on interstitial fluid glucose levels of a user, which may be correlated to blood glucose levels. A BGM may be configured to provide blood glucose data, typically based on a blood sample. Accordingly, while the term "blood glucose" may, at times, be used as a general term simply for convenience, the disclosure is not limited to using just blood glucose data, values, levels, etc., but also interstitial fluid glucose levels, as well as any intermediate measurement values.

In some embodiments, the pen cap may automatically receive glucose data from a CGM automatically without user action so long as the pen cap is in range. In some embodiments, the pen cap may be adapted to wirelessly receive current EGVs (and, optionally, prior EGVs) from a flash glucose monitor when the pen cap is positioned in proximity to (e.g., swiped adjacent to) the flash glucose monitor. In some embodiments, EGVs may be obtained via a BGM, which may be in wireless communication with the pen cap or a mobile computing device (which can then transmit the EGV to the pen cap) or may be entered by a user into a remote computing device.

Accessories provided herein (e.g., pen caps), in some embodiments, may be configured to␣␣␣that they only retrieve glucose data upon a user interacting with the pen cap. For example, if a pen cap is adapted to obtain glucose data from a CGM or flash glucose monitor, the pen cap may be designed so that it needs to be swiped near the CGM or flash glucose monitor or may be designed so that it can only retrieve glucose data when a demand is made by the user (e.g., when a button is pressed). In some embodiments, a CGM may be in wireless communication with a mobile computing device (e.g., a smartphone, tablet) and data from the CGM only transferred to the pen cap when a button is pressed on the pen cap.

Accessories (e.g., pen caps) or mobile applications provided herein can, in some embodiments, provide reminders to a user to obtain glucose data. For example, in the case of methods and systems that include a flash glucose monitor, a reminder may be sent to the user to obtain glucose data by swiping the pen cap near the flash glucose monitor. In some embodiments, reminders to obtain glucose data may be timed based on pen capping information. For example, a reminder to obtain blood glucose data may be determined based on a time since the most recent capping (e.g., the current capping duration exceeding a threshold). In some embodiments, the threshold may be set to reduce the likelihood that a dosage of insulin may cause a hypoglycemic event. In some embodiments, a pen cap can wirelessly receive blood glucose data and analyze patterns of the blood glucose data in comparison to pen capping information to determine a likelihood of a future hypoglycemic event or a predicted future blood glucose value. In some embodiments, blood glucose data and pen capping information may be wirelessly transmitted to a remote computing device (e.g., smartphone, tablet, etc.) and analyzed in that remote computing device or in the cloud or other network or device to determine a likelihood of a future hypoglycemic event or a predicted future blood glucose value, which may be used to issue a notification, alert, or alarm and/or to set a reminder to obtain blood glucose data.

Pen caps provided herein can use any suitable technique to obtain pen capping information (e.g., information relating to removal/application of the pen cap during an insulin injection). In some embodiments, pen caps provided herein can include a biasing element, such as, for example, a leaf-spring on the inside of the cap that completes a circuit when the pen cap is secured to the injection pen. In other embodiments, the cap may include a sensor (e.g., an optical sensor, a mechanical sensor, an electronic sensor, a magnetic sensor, etc.) that detects when the cap is applied to and/or removed from the pen.

Accessories (e.g., pen caps), methods, and systems provided herein can use any suitable method for making therapy recommendations. In some embodiments, a user or healthcare professional can set recommended dosage amounts for initiation of the product, set one or more initial carbohydrate-to-insulin ratios, set one or more initial insulin sensitivity factors, create a table of correction doses to be used for a particular range of glucose values, and/or set one or more meal characterizations. For example, in some embodiments a user or healthcare professional may set the initial recommended dose of long-acting insulin and a carbohydrate-to-insulin ratio and an insulin sensitivity factor to be used in determining doses of rapid-acting insulin. In some embodiments, a user or healthcare professional may set typical meal sizes in carbohydrates for breakfast, lunch, and/or dinner. In some embodiments, a user or healthcare professional may set typical meal-based rapid-acting insulin doses for the user for breakfast, lunch, and dinner. In some embodiments, a user or healthcare professional may set characterizations of differently sized meals (small (S), medium (M), large (L)) for different times of day (e.g., 10 g of carbohydrates for S, 25 g for M, and 50 g for L). In some embodiments, blood glucose data and/or pen capping information may be analyzed to make adjustments to a user's dosage parameters and/or the meal-based dosage recommendations. In some embodiments, blood glucose data and/or pen capping information may be analyzed to make suggested changes to a user's dosage parameters and/or the meal-based dosage recommendations to a healthcare professional or to a user.

In some embodiments, accessories provided herein (e.g., pen caps) may provide meal-based bolus recommendations based on a time of day and/or meal categories. For example, in some embodiments, the pen cap may provide different meal-based bolus recommendations based on it being breakfast time (e.g., about 8 am), lunch time (e.g., about noon), or dinner time (e.g., about 6 pm). In some embodiments, the pen cap may provide different meal-based bolus recommendations for different meal categories, meal preferences, or historical meal statistics, such as, for example, small (S), medium (M), and large (L), which may be based on the number of carbohydrates or the glycemic impact of a meal as estimated or determined by a user. For example, for each therapy recommendation, a user may see a recommended meal-based bolus for a S meal, for a M meal, and for a L meal. In some embodiments, a user may press a button or user-selectable icon to request a recommendation for a S meal, for a M meal, or for a L meal. In some cases, the meal-based bolus recommendations for each meal category (S, M, and L) can change based on the time of day. In some embodiments, the meal-based bolus recommendations for each meal category (S, M, and L) may change based on a historical evaluation of the user's meal sizes and/or consistency. In some embodiments, a single display can indicate different suggested insulin dosages based on different meal characteristics and/or display a range of dosages based on the user's typical meal sizes (e.g., customized to the user's meal sizes based on historical data), which may be based on the time of the day, day of the week, day of the year, location of user, or any other collected data.

In some embodiments, a system provided herein can include one, two, or more connected pen caps for insulin pens or other accessories for an insulin pen (e.g., a connected dose-capture insulin pen cap), a continuous glucose monitoring system (CGM) (or a flash glucose monitoring system), a mobile application, an alert accessory, and/or critical web services cloud software. In some embodiments, connectivity to the cloud-based server can enable the storage of data for use by the system when needed and transfer of information to other devices outside of the system (e.g., optional secondary display of data, reports). In some embodiments, components of systems provided herein may be wirelessly connected or can wirelessly connect using either Bluetooth Low Energy (BLE), 433 MHZ ultra-high-frequency (UHF) radio, and/or a near-field communication (NFC) protocol.

One or more embodiments of the present disclosure may include an insulin delivery system that includes an insulin delivery device, a user interface on the insulin delivery device or adapted to be secured (either releasably or non-releasably) to the insulin delivery device, memory to store one or more user-specific dosage parameters, and one or more processors in communication with the memory and adapted to receive blood glucose data, determine a recommended insulin dosage, and/or determine an estimate of insulin administered using the insulin delivery device. The user interface can display one or more recommended insulin dosages using, at least in part, blood glucose data and/or previous estimates of insulin administered, data about prior insulin dosages (e.g., IOB characteristics) associated with each of the user-selectable icons or buttons based on at least one of the user-specific dosage parameters. The processor may be adapted to update the meal characteristics associated with each of the user-selectable icons or buttons based upon the blood glucose data.

In accordance with one or more devices, systems, or methods of the present disclosure, the systems or methods may include a glucose monitor that may provide blood glucose data via one or more communication (e.g., wireless communication) techniques. In some embodiments, a glucose monitor of systems or methods provided herein can use multiple wireless communication techniques to transmit blood glucose data. For example, a glucose monitor can include a flash near-field communication circuit and a wireless radio. In some embodiments, systems and methods provided herein can have one or more insulin pens or pen accessories receive blood glucose data from a glucose monitor via a first communication technique (e.g., NFC) and have another device (e.g., a mobile device) receive data from the glucose monitor and/or the insulin pens via a second communication technique (e.g., BLE or UHF). In some embodiments, smart pen or pen accessories in methods and systems provided herein may communicate with a continuous and/or glucose monitor of methods and systems provided herein only within a first range and the mobile device may be adapted to passively receive data whenever within a second range that is larger than the first range. In some embodiments, smart pens or pen accessories provided herein may be configured so that the smart pen or pen accessories only receive data when the user elects to take action to receive data (e.g., push a "wake up" button and/or bring the pen or pen accessory within a close proximity to the glucose monitor), but another device (e.g., an associated mobile device) may be adapted to passively receive data regardless of user action if within a range determined by the communication method or link.

In accordance with one or more devices, systems, or methods of the present disclosure, a user interface on the smart insulin delivery device or accessory therefore can include one or more user-selectable buttons or icons. In some embodiments, a user-selectable button or icon may be used to wake up the smart pen or pen accessory to receive blood glucose data from a blood glucose monitoring/sensor system (e.g., that includes a CGM, BGM, flash glucose monitor, etc.). In some embodiments, a user-selectable button or icon may be used to wake up a display on the smart pen or pen accessory to display a recommended insulin dosage amount for the insulin in the smart pen or in an insulin pen secured to the pen accessory. In some embodiments, a user-selectable button or icon may be used to toggle the display between different displays. In some embodiments, a single user-selectable button or icon may be used to wake up the smart pen or pen accessory to receive blood glucose data and to wake up the display, which can then display a recommended insulin dosage upon the smart pen or pen accessory that receives the blood glucose data. In accordance with one or more devices, systems, or methods of the present disclosure, the processor may determine a dosage recommendation of rapid-acting insulin based on factors selected from the number of carbohydrates divided by the PWD's carbohydrate-to-insulin ratio, a difference between the current blood glucose level and a target blood glucose level divided by the PWD's insulin sensitivity factor, a reading from a blood glucose meter (BGM), data from a continuous glucose monitor (CGM), blood glucose trend data, Insulin-on-Board (JOB) data, Carbohydrates on Board (COB) data, whether the PWD is exercising or plans to exercise, whether the PWD is sick, whether the PWD is pregnant, whether the PWD is experiencing menses, and whether the PWD has consumed certain medications.

In some embodiments, a reusable smart pen that may include a dosing detector, a reusable chamber one or more types of insulin cartridges, and a manual delivery mechanism. The detector may be configured to detect first insulin delivery events associated with a manual delivery mechanism.

System Architecture for Therapy Management System

FIG. 1A illustrates an insulin therapy management system 10 (which may also be referred to as a diabetes management system), that includes an analyte sensor system 101 (in this example, a glucose sensor system 101), a first accessory 102, a second accessory 103, and a mobile application 104. The insulin therapy management system 10 may include one or more web services 105 that communicate with the mobile application 104 by way of a network 108. The first accessory 102 and second accessory 103 are two of many accessories that may join and leave the insulin therapy management system 10, and serve to assist users with manual insulin delivery.

While aspects of the embodiments of the disclosure are described in terms of accessories and caps, one of ordinary skill in the art would understand that many of the features could be performed in an electronics package (i.e., a smart electronics) that is integratable with an insulin delivery device, attachable to an insulin delivery device, attachable to an insulin container, and more, all of which are specifically contemplated by the inventors of this disclosure.

The first accessory 102 and second accessory 103 may be configured to capture information related to the delivery of insulin by manual delivery device 106 and manual delivery device 107, and, in various embodiments, may include internal sensors for dose capture; user interfaces for displaying information and receiving user input; and other interfaces for wireless or wired communication with one or more of the manual delivery device 106, manual delivery device 107, mobile application 104, the analyte sensor system 101, and mobile application 104.

The mobile application 104 may execute on any suitable mobile computing device that can store and execute a mobile application that is adapted to display and input therapy relevant information wirelessly received from the other components of the system as well as from a graphical user interface that enables user to interact with the application. In one embodiment, the mobile device can also store and execute a trusted mobile application within a trusted execution environment (hardware and/or software) that is not, generally speaking, accessible to users or devices communicating with the mobile device 140 but that is accessible to other applications executing on the mobile device 140. Various functions and calculations that relate to the therapy management system, including the alerts and recommendations that are presented to users may be, in part or in whole, performed by the trusted mobile application. Moreover, some or all communication with insulin pens, pen caps, glucose sensors, and other accessories may be restricted to the trusted mobile application.

Generally, the embodiments of the disclosure may use any suitable wireless communication protocol for communication among accessories, manual delivery devices, glucose sensors, and mobile devices. Examples of suitable wireless communication protocols include near-field-communication (ISO/IEC 14443 and 18092 compliant technology), wireless modems and routers (IEEE 802.11 compliant technology), and BLUETOOTH®/Bluetooth Low Energy (BLE) (IEEE 802.15 compliant technology).

The glucose sensor system 101 may be any suitable glucose sensor system 101, such as a blood glucose meter (BGM) adapted to determine blood glucose values using blood glucose test strips, and flash glucose monitor, or a continuous glucose monitor (CGM). In some cases, a glucose sensor system 101 can act as both a flash glucose monitor and a continuous glucose monitor by permitting both intermittent and on-demand transmissions of blood glucose data. In some embodiments, the glucose sensor system 101 can wirelessly transmit data when interrogated by a reader device (e.g., using NFC communication). In some embodiments, the glucose sensor can wirelessly transmit data at predetermined intervals (e.g., using radio frequencies) using any suitable communication standard (e.g., Bluetooth Low Energy (BLE)). In some cases, systems and methods provided herein can include multiple glucose sensor systems (e.g., a continuous or flash glucose monitor and a blood glucose meter).

In some embodiments, an accessory may be associated with a particular type of insulin, for example, the first accessory 102 is associated with long-acting insulin delivery and the second accessory 103 is associated with rapid-acting insulin delivery.

In some embodiments, the glucose sensor system 101 can transmit glucose data using multiple communication techniques. In some embodiments, the mobile application 104 and/or one or more of the manual delivery devices 106, 107 or accessories 102, 103 may include an NFC reader adapted to obtain blood glucose data from the glucose sensor system 101 when brought within an interrogation distance of the glucose sensor system 101. In some embodiments, the mobile application 104 and/or one or more of the manual delivery devices 106, 107 or accessories 102, 103 may wirelessly receive blood glucose data from the glucose sensor system 101 that is broadcast at predetermined periods of time (e.g., every 30 seconds, every minute, every 2 minutes, every 3 minutes, every 5 minutes, every 10 minutes, every 15 minutes, etc.).

In a polled (or interrogated) mode of operation, the glucose sensor system 101 may wirelessly send blood glucose data to one or more of the accessories 102, 103 and the mobile application 104, that corresponds to a historical period. For example, when the first accessory 102 interrogates the glucose sensor system 101 it may receive stored glucose data from the previous 1 hour, 2 hours, 3, hours, 4 hours, 5 hours, 6 hours, 7 hours, 8 hours, etc. In some cases, broadcast blood glucose data may only include a current or more recent blood glucose value. For example, in some cases blood glucose data received on the mobile application 104 received directly from the glucose sensor system 101 may include only the most current readings (e.g., from the last 10 minutes), which may be used by the mobile application 104 to issue alarms or alerts based on the most current blood glucose data.

Accessories 102, 103 can include one or more processors and memory for controlling wireless communications, controlling interfaces for wireless communication, controlling a user interface, and/or determining therapy recommendations.

In some embodiments, an application running at the accessories 102, 103 may execute one or more algorithms to determine estimated glucose values (EGVs) from raw glucose sensor data. In some embodiments, a glucose sensor system 101 can transmit EGVs to an accessory. In some embodiments, accessories and/or smart electronics provided herein can include memory that stores user-specific dosage parameters (e.g., a recommended daily dose of long-acting insulin or total daily basal dose (TDBD), insulin sensitivity factor (ISF), carbohydrate-to-insulin ratio (CR), correction amounts based on blood glucose level ranges, total daily insulin dose (TDD), target glucose value, recommended rapid-acting doses for different meal sizes or categories, etc.). In some embodiments, user-specific dosage parameters may be time or day dependent, such as CR and ISF values that depend on the hour of the day. In some embodiments, accessories 102, 103 provided herein can have memory that stores recommended doses of rapid-acting insulin for different meals or for different meal categories. In some embodiments, user-specific dosage parameters and/or different recommended doses for different meals may be updated via mobile application 104 in wireless communication with an accessory. For example, an algorithm in the mobile computing device or in the cloud can update these parameters or recommended doses. In some embodiments, parameters or recommended doses may be updated by a healthcare professional or manually by the PWD or a caregiver. In some embodiments, the accessory can include an algorithm in memory to be executed by a processor to automatically update the user-specific dosage parameters or recommended doses.

Accessories 102, 103 provided herein can, in some embodiments, display or otherwise provide notice to a user of a current blood glucose level and/or blood glucose trend data (e.g., a rate of change) based on glucose data received from the glucose sensor system 101. Accessories 102, 103 (or other smart electronics) provided herein may provide recommended doses of insulin based on one or more of blood glucose data, user-specific dosage parameters, recommended dosage amounts set by a user or healthcare professional, time-of-day, meal data or categorizations, or any other suitable input.

While system 10 is described with two accessories 102, 103, it is not limited and may include more or fewer accessories. For example, first accessory 102 may include a pairing or discoverable mode where it broadcasts information that is discoverable by mobile application 104. The broadcast may be according to a BLUETOOTH® beacon or other suitable communication protocol. Responsive to pairing confirmation such as holding the first accessory 102 and mobile device hosting the mobile application 104 close together or depressing a button for sufficient time either at the first accessory 102 or mobile application 104, the mobile application 104 may create a profile for a manual delivery device that is associated with the first accessory 102. In one embodiment, the first accessory 102 may be specifically calibrated for a specific type of manual delivery device and may provide a delivery device type identifier to the mobile application 104. In another embodiment, when the first accessory 102 and mobile application 104 are paired, setup information may be provided at the mobile application 104 or at the interface of the accessory.

In one embodiment, pairing may also involve sharing encryption keys that the devices may use to decrypt/authenticate messages from devices within the system 10.

Each accessory that is paired with the system 10 may have a profile created by the mobile application 104. In one embodiment, the mobile application 104 may query web services 105 for whether a profile for a device already exists for a user, and, if it does, request that it be sent. This enables the mobile application 104 to avoid reduplicating setup as well as may make available to the recommendation algorithms running at the mobile application 104 more historical data or physiological attributes of the user (e.g., insulin sensitivity) that have been refined by actual glucose measurements and blood glucose response analysis.

Upon creating the profile, the mobile application 104 may save insulin therapy related settings with the profile. The insulin therapy related settings may include user-specific dosage parameters for a user, delivery characteristics of the device, specific techniques that may be used to determine recommendations.

In one embodiment, each manual delivery device profile may include, or be part of a user profile that includes, pre-configured correction doses for particular blood glucose ranges. In one embodiment, the pre-configured doses may be entered at the mobile application 104. In another embodiment the pre-configured doses may be entered at one of the web services 105 (e.g., by a healthcare provider or parent), and downloaded to the mobile application 104.

As will be described in more detail below, in one embodiment, a user may select from among the available doses and the system will monitor for dosing actions at an associated manual delivery device. As described more fully herein, dosing actions may be specifically detected (e.g., by detecting medication exiting a needle of a delivery device) or inferred (e.g., using capping information). In some cases, the correction doses may not be available for a limited period of time after insulin dose or detected possible dose. For example, methods, systems, and devices provided herein may be able to detect a dose or possible dose, but not be able to determine a dose amount, thus such systems, methods, and devices may not be able to determine an amount of active insulin (e.g., IOB) remaining in the user, thus such systems may prevent the calculation or suggestion of a correction does for a certain period of time (e.g., at least 2 hours, at least 3 hours, at least 4 hours, or at least 5 hours) after a prior detected dose or detected possible dose of rapid-acting insulin.

Since, meal dose recommendations may be calculated for a manual delivery device that has rapid-acting insulin, a profile may also include or refer to algorithms for calculating meal doses for offsetting the effects on blood glucose levels of small, medium, or large meals. In one embodiment, the algorithms may be personalized to a user, initially, with physiological information about the user, and over time, personalized using actual glucose sensor data and dosing event information.

The mobile application 104 is configured to record historical therapy related information, for example, a history of blood glucose levels, dosing amounts, dosed medication, and dosing timing information.

The system 10 is also configured such that an accessory may be removed. For example, at a setup screen of the mobile application 104 a user may select a manual delivery device 107 to be removed/unpaired from the system 10. Responsive to a selection, the manual delivery device 107 may initiate a confirmation prompt to the user. In one embodiment, a confirmation process involving a specific user action (e.g., holding down a button at a mobile device and a button at the accessory) may be used to confirm the removal. Responsive to the confirmation the device profile may be stored and the second accessory 103 may change to an unaffiliated state and power down.

The system 10 is also configured to add and remove glucose sensor system 101, and other glucose monitoring devices configured to send blood glucose data. For example, and as described below, swiping or waving second accessory 103 within proximity of glucose sensor system 101 may activate a communication link between second accessory 103 and the glucose sensor system 101. In one embodiment, the communication link may be initiated according to a near-field-communication (NFC) protocol where an antenna and reader IC at the accessory interrogates a tag (typically a chip) at the glucose sensor system 101. Affiliation/activation data may be shared among the system so that other devices (accessories, mobile devices, etc.) may access the blood glucose data at the glucose sensor system 101.

Background Activity and Sync

The following activities may be carried out in the background when the necessary devices are available and online. These activities are described in the following workflow and may vary based on system status. For the following description, the first accessory 102 is associated with long-acting insulin delivery and the second accessory 103 is associated with rapid-acting insulin delivery.

Program Execution on First Accessory Associated with Long-Acting Insulin Delivery In one embodiment, the first accessory 102, or a device in communication with the first accessory 102, may execute software to calculate a user's required long-acting insulin dose. In one embodiment, glucose measurement values are sent to a long-acting insulin dose recommendation service hosted in the cloud. In various embodiments, the glucose values may be sent to the cloud services (e.g., via a wireless or cellular connection) at regular intervals such that updates to the therapy parameters may be made, as described in the workflow above. In one embodiment the pen cap 112 may include wireless or cellular equipment and may send the glucose values to the cloud service via wireless or cellular connection. In another embodiment, the first accessory 102 may piggyback on the wireless or cellular connection of a mobile device at which the mobile application 104 executes. The first accessory 102 periodically backs up data to the cloud via the mobile application 104 (e.g., via a local connection, such as a BLUETOOTH® or BLE connection).

The first accessory 102 may receive updated therapy parameters back from the cloud or web services 105 when they are approved and available. Data flow examples are described below.

Program Execution on a Second Accessory Associated with Rapid-Acting Insulin Delivery In one embodiment, the second accessory 103 associated with rapid-acting insulin delivery, or a device in communication with the second accessory 103, executes the software containing the algorithm to calculate the user's required rapid-acting insulin dose. Glucose values and meal choices may also be sent to a rapid-acting insulin dose recommendation service as well as (e.g., via a wireless or cellular connection) at regular intervals such that calculations may be made as described in the workflow above. In one embodiment the second accessory 103 may include wireless or cellular equipment and may send the glucose values to the cloud service via wireless or cellular connection. In another embodiment, second accessory 103 may piggyback on the wireless or cellular connection of a mobile device having the mobile application 104 installed and executing thereon. The second accessory 103 periodically backs up data to the cloud via the mobile application 104 (e.g., via a local connection, such as a BLUETOOTH® or BLE connection).

The second accessory 103 receives updated therapy parameters back from the cloud services when they are approved and available. This flow of data is discussed in a later section.

Program Execution on Mobile App

The mobile application 104 may run in the background to sync with BLE devices (e.g., first accessory 102 and second accessory 103, glucose sensor system 101) and the cloud to act as a conduit of information. Information is synced regularly per the descriptions above. Additionally, system status configuration, dose history, and glucose trends and forecasting may be viewed as they are calculated in the cloud and pushed to the mobile application 104.

Updating Therapy Parameters

As shown in FIG. 1A, the cloud service may execute an algorithm to update and individualize the user's therapy parameters over time (ISF, CR, TDBD, glucose target, correction chart, meal category doses) based on information provided from the local system (e.g., to the cloud). These values may be updated when data is pushed from the accessories 102, 103 via the PWD's mobile application 104 to the cloud. In one embodiment, when a new value is ready to be pushed to the user's mobile application 104, it may be first pushed to a healthcare-provider's (HCP's) Web Portal for approval (e.g., via a wireless or cellular connection).

In some cases, a portal may alert an HCP that a new set of parameters is ready for review. The clinician may then review the values and either approve or reject them. If rejected, the cloud service is notified and no other action occurs.

If accepted, the cloud or web service 105 is notified and the values (e.g., the updated parameters) are pushed to the user's mobile application 104 for acceptance (e.g., via one of the local devices of the system, such as the accessories 102, 103, and/or the mobile application running on a mobile device). For example, the values may be transmitted to the mobile application, which then communicates the values locally to one or both of the accessories 102, 103.

In some cases, an algorithm can determine if an update is suggested and send a notice to the user that suggests that the user update the user's therapy parameters (perhaps in consultation with the user's doctor).

Figure 14:
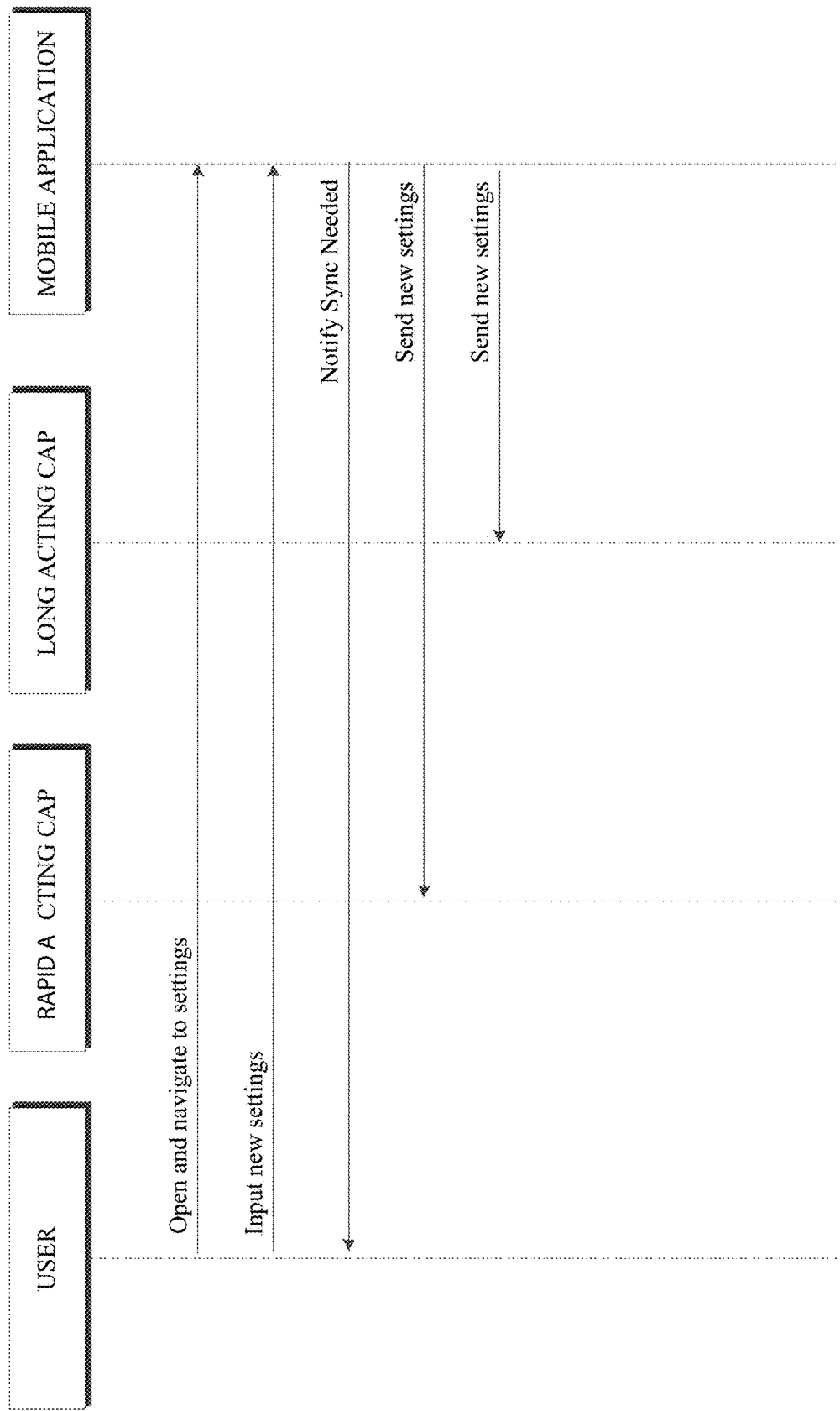
FIG. 14 illustrates a process for updating therapy information according to an embodiment of the disclosure.

FIG. 14 shows an example process for updating therapy information, according to an embodiment of the disclosure. In operation 502, a user accesses therapy settings using the mobile application 104. The therapy settings may be stored at the mobile application 104, the accessories 102, 103, or both. In operation 504, new therapy settings are provided via a user interface provided by the mobile application 104 and configured to receive new settings. In operation 506, the mobile application 104 may present a notification at the user interface that settings need to be synced to the accessories 102, 103. In operations 508 and 510, the mobile application 104 may wirelessly communicate one or more of the new settings to the accessories 102, 103. In one embodiment, long-acting relevant therapy settings are sent to the accessory associated with long-acting insulin delivery and rapid-acting relevant therapy settings are sent to the accessory associated with rapid-acting insulin delivery.

Pen Cap and Insulin Pen System Architecture

During use, insulin therapy management system 10 may assist a PWD (or their caregiver) responsible for determining when to inject insulin and how much insulin to inject. System 10 may be configured to provide recommendations to assist the PWD (or caregiver) in determining an appropriate insulin dose based on current data from the glucose sensor, based on stored therapy parameters, and/or based on data about insulin injections. In some embodiments, the accessories 102, 103 are configured to collect and provide data about insulin injection events.

Figure 1B:
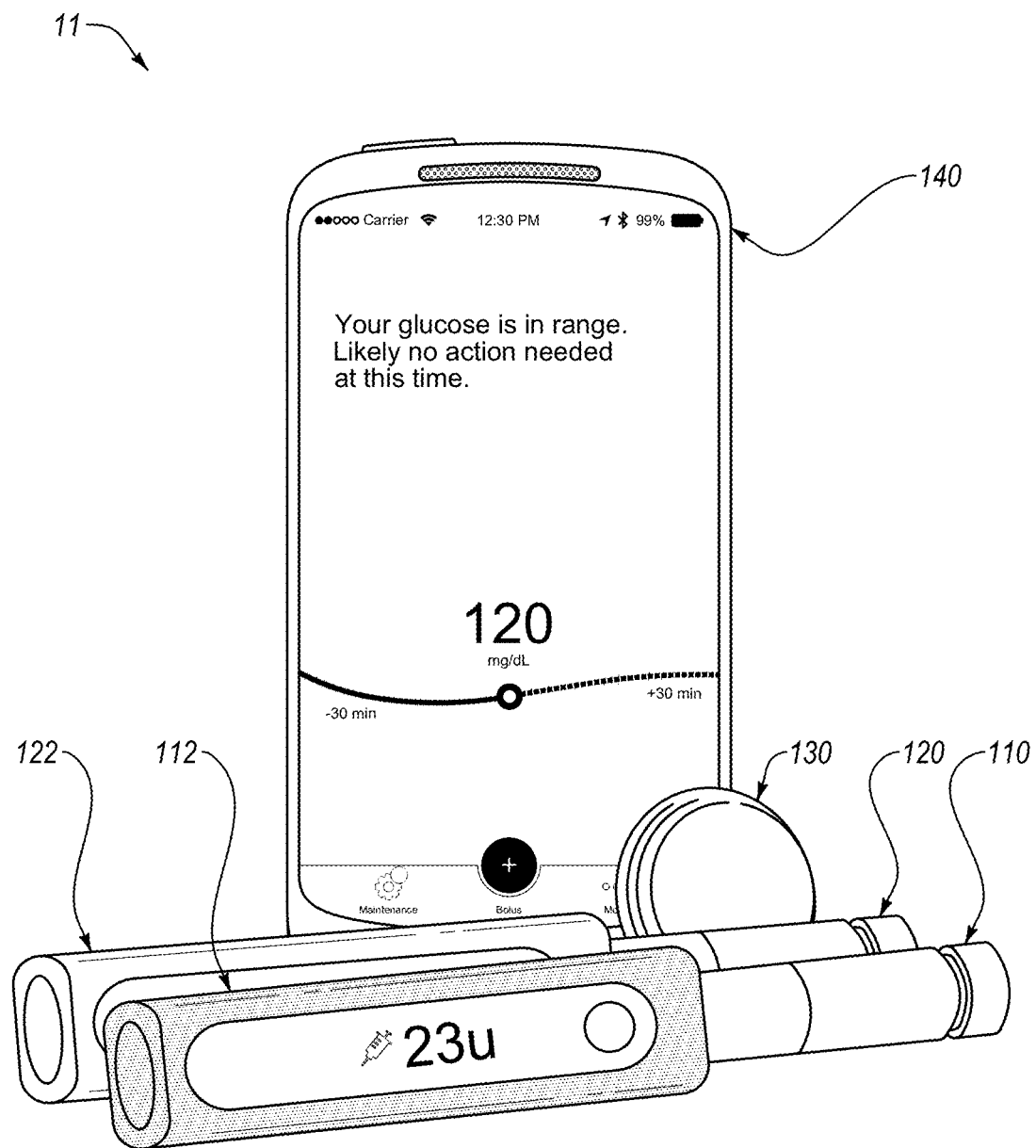
FIG. 1B illustrates the specific components of an exemplary diabetes management system.
Figure 1C:
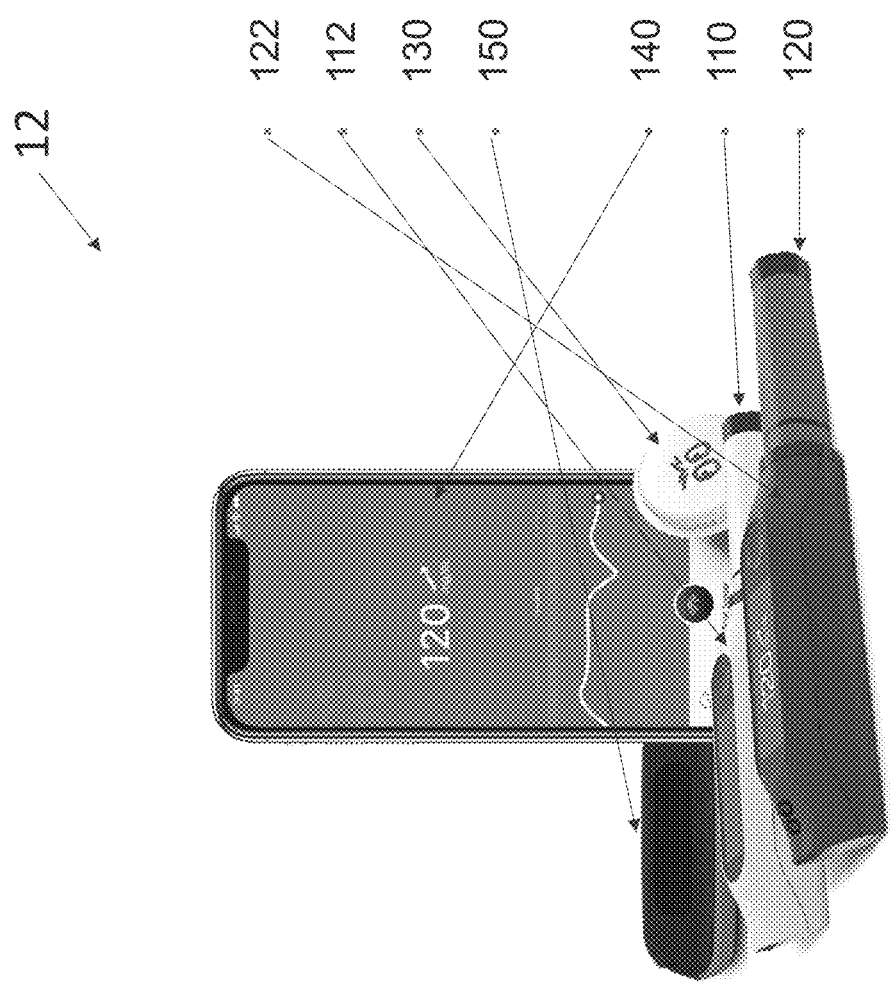
FIG. 1C illustrates a second exemplary diabetes management system.

In one embodiment the manual delivery devices 106 and 107 shown in FIGS. 1B and 1C, may be insulin pens, including, commercially available mechanical insulin pens that include any suitable insulin, for example, long-acting insulins and rapid-acting insulins (sometimes called quick-acting insulins or ultra-fast rapid-acting insulins). Suitable rapid-acting insulins include HUMALOG®, NOVOLOG®, APIDRA®, and FIASP®. Suitable long-acting insulins include LANTUS®, LEVEMIR®, TOUJEO®, and TRESIBA®.

By way of example, manual delivery device 107 may be a long-acting insulin injection pen 110, and manual delivery device 106 may be a rapid-acting insulin injection pen 120 as shown in FIGS. 1B and 1C. In FIG. 1B, shown is an insulin therapy management system 11, insulin pen 110, insulin pen 120, CGM 130, and mobile device 140, which has a therapy management mobile application executing thereon. The first accessory 102 may be a pen cap 112 and the second accessory 103 may be a pen cap 122. In FIG. 1C, shown is an insulin therapy management system 12, insulin pen 110 having pen cap 112, insulin pen 120 having pen cap 122, CGM 130, blood glucose meter ("BGM") 150, and mobile device 140, which has a therapy management mobile application executing thereon. As shown, system 12 has the components of system 11 but also has a BGM 150 and a different mobile application display of blood glucose values.

The insulin pens 110, 120 may include dials (not shown) that may be used to configure the pens to inject a dose of insulin that corresponds to the dial turn. In some embodiments, each insulin injection pen may be a reusable insulin pen that includes a display or audio and/or input devices such as those disclosed for the pen caps disclosed herein. One example of a reusable insulin pen is an insulin pen that includes a chamber for unloading depleted insulin cartridges and loading new insulin cartridges. The insulin pens 110, 120 may include interfaces for wireless and/or wired communication with one or more of the pen caps, glucose sensor, mobile devices, and other accessories.

Pen capping information (i.e., information about when the pen cap is secured to and/or released from an insulin pen—also referred to herein as "capping" and "uncapping" respectively) can include information about a current capping period (e.g., the time since the last capping), information about a duration of one or more uncapping, and the timing (e.g., time-of-day or time elapsed since) of each uncapping and each capping. In some embodiments, pen capping information may be displayed at an interface of a pen cap to a user. In some embodiments, pen capping information may be announced by a speaker in the pen cap. For example, in some embodiments, a pen cap may provide a timer clock that counts up (or a timer that counts down) from the last time the pen cap was secured to an injection pen. In some embodiments, a pen cap can wirelessly communicate pen capping information to mobile device 140 (e.g., a smartphone, tablet, etc., running a mobile application).

Pen capping information may be used to adjust the user experience. In some embodiments, the pen cap adjusts the presentation of therapy relevant information and/or recommendations provided to the user responsive to the pen capping information. For example, in some embodiments, a pen cap may provide bolus recommendations to correct for elevated glucose levels based on data from a CGM 130, but may limit the presentation of such correction bolus recommendations to time periods when the current pen capping duration is greater than a threshold period of time (e.g., at least 3 hours, at least 4 hours, or at least 5 hours). In some embodiments, the pen caps 112 and 122 may provide notifications, alerts, and/or alarms to the user based on the pen capping information (e.g., based on the amount of time that a pen has been capped and/or uncapped). For example, if the pen caps 112 and 122 are removed from an injection pen within a threshold period of time (e.g., within 30 minutes or 1 hour for a rapid-acting insulin, within 6-12 hours for a long-acting insulin) from a previous capping, the pen cap may provide a visual, audible, and/or tactile notification to indicate that the user may have recently used the pen to administer insulin. In some embodiments, the pen caps 112 and 122 may be in wireless communication with a mobile device 140 and one or more notifications, alerts, and/or alarms based on pen capping information may be announced or displayed on the mobile computing device.

A capping sensor for detecting possible capping events, uncapping events, and recapping events may be an analog or digital electronic sensor integrated with a pen cap, or, more generally, with an accessory, that responds to being attached or removed from an insulin pen. In one embodiment, it may incorporate a piezoelectric material that generates a small current when pressure (e.g., from being firmly affixed to an insulin pen) is exerted on it. In another embodiment, it may respond to relative motion between itself and a small magnetic element affixed to the medical delivery device. In yet another embodiment, it may respond to an open and closed circuit (e.g., open loop when cap off, closed when cap is on). Any suitable sensor for detecting capping and uncapping may be used.

Capping/Uncapping Events and Dosing Events

Pen capping information may be stored, displayed, and analyzed in combination with glucose data to determine user behaviors, such as whether the person is appropriately dosing insulin for meals and/or to correct elevated blood glucose levels. In some embodiments, pen capping information may be presented on a graphical representation of blood glucose data for the user and presented to a user and/or to a healthcare professional. In some embodiments, blood glucose data from a period of time after each capping event may be evaluated to determine whether the user appropriately dosed insulin for that capping event, under-dosed, or over-dosed.

In some embodiments, a pen uncapping event, pen capping event, or pen recapping event may be disregarded where other information indicates that a dose was not provided. For example, where no change in the dosage selection of the insulin pen (e.g., a dial) was detected, the event may be disregarded.

In one embodiment, pen caps 112, 122 may be configured to track pen capping events that may be used to infer dosing actions. In various embodiments, the systems 11 and/or 12 may be configured to infer that a capping event corresponds to a dosing action and record it (e.g., as a dosing event), including one or more of the time, type of insulin, and amount of insulin delivered. In one embodiment, the amount of insulin delivered may be captured at the insulin pens 110, 120 and provided to the pen caps 112 and 122. In some embodiments, pen caps 112, 122 can determine and track remaining insulin in the insulin pens 110, 120 based on the amount of each dose. In another embodiment, the pen caps 112, 122 may track the amount of insulin that remains in an insulin cartridge and determine an amount of insulin associated with a dosing action based on a change of the amount of insulin in an insulin cartridge. In additional embodiments, smart pens or pen accessories can detect the dosages set or administered using other suitable techniques.

In some embodiments, the pen caps 112, 122 may include one or more smart sensors to detect a substance on a user's fingers, sensors, such as a temperature sensor to determine (e.g., along with blood glucose data) if the insulin needs to be replaced or has gone bad, a touch screen, and a capacitive touch button. For example, one or more of the mobile application or the pen caps 112, 122 may include a temperature monitor that monitors one of more of average temperatures, high temperatures, or low temperatures experienced by the pen caps 112, 122. Such temperature ranges and/or minimum and maximums may be attributed to the therapy (e.g., insulin) attached to the pen caps 112, 122. Upon exposure to a minimum and/or maximum temperature (e.g., or a selected time period within a selected temperature range), the pen caps 112, 122 may provide an alert and/or alarm to the user that the insulin has been exposed to an out-of-range temperature (e.g., a level beyond recommendations for user and/or storage of the insulin).

In some embodiments, such a temperature sensor may be used in unison with the blood glucose sensor to indicate, where the insulin has been exposed to a select temperature level, that the insulin is not having an expected effect on the subject's blood glucose level. For example, an alarm and/or alert may be provided where the insulin has been exposed to an out-of-range temperature and where data from the blood glucose monitor data is indicating that the insulin is not having an expected effect on the subject's blood glucose levels (e.g., less than or more than an expected change). In some cases, methods, systems, and devices provided herein can condition notifications regarding temperature exposure based on additional data that indicates that the effectiveness of the insulin has been compromised or may have been compromised in order to mitigate against the user experiencing notification fatigue. In some embodiments, the mobile application or the pen caps 112, 122 may trigger a reminder for the user to make a post-injection reading to determine the effectiveness of the insulin that was recently provided to the subject.

In some embodiments, the mobile application or the pen caps 112, 122 may communicate with a wearable device on the PWD (e.g., a smartwatch) to determine an action being undertaken by the subject (e.g., if the subject is eating). For example, a wearable application may execute on the wearable device that enables a user to interface with one or more of the pen caps 112, 122, the insulin pens 110, 120, the mobile device 140, and other accessories. In some embodiments, the wearable application may interface with a mobile application executing on the mobile device 140, such as mobile application 104. The mobile application may perform the processing for various features described herein, and the wearable application may serve the alerts and recommendations to a user as well as serve information to the mobile application received from the user at the wearable device, such as indications of a meal, exercise, or dosing action.

Swiping/Gathering Glucose Information

Figure 2:
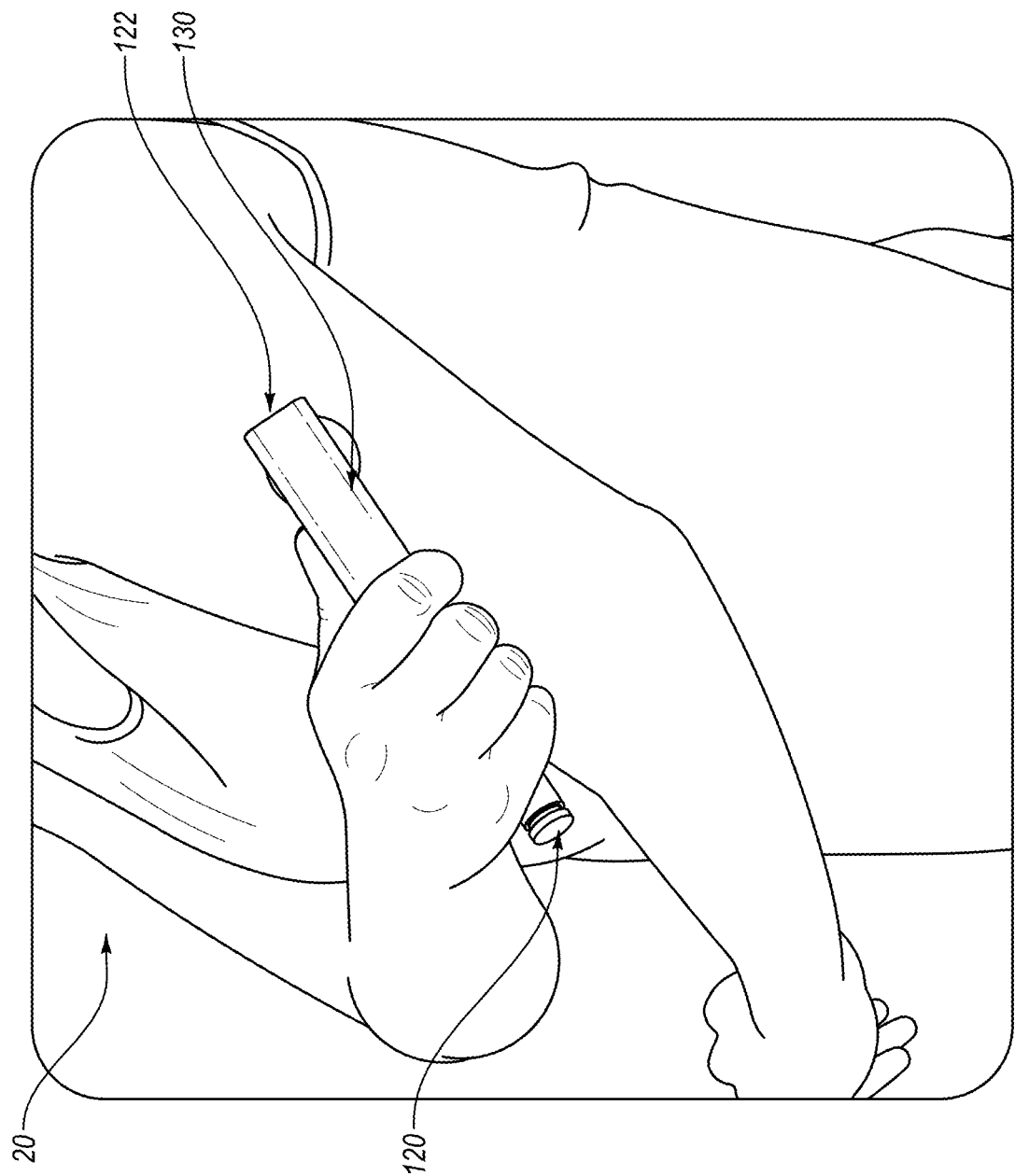
FIG. 2 illustrates a user utilizing one or more portions of a diabetes management system according to embodiments of the present disclosure.

FIG. 2 illustrates a PWD utilizing one or more portions of the insulin therapy management system 11 of FIG. 1B. As shown in FIG. 2, a PWD 20 can have, e.g., a glucose sensor system 101 applied to their arm so that it can detect the PWD's blood glucose levels, and a user may use pen cap 122, secured to rapid-acting insulin pen 120, to interrogate glucose sensor system 101. Before and after the user swipes the pen cap 122 in FIG. 2, pen cap 122 can display therapy relevant information.

Figure 3:
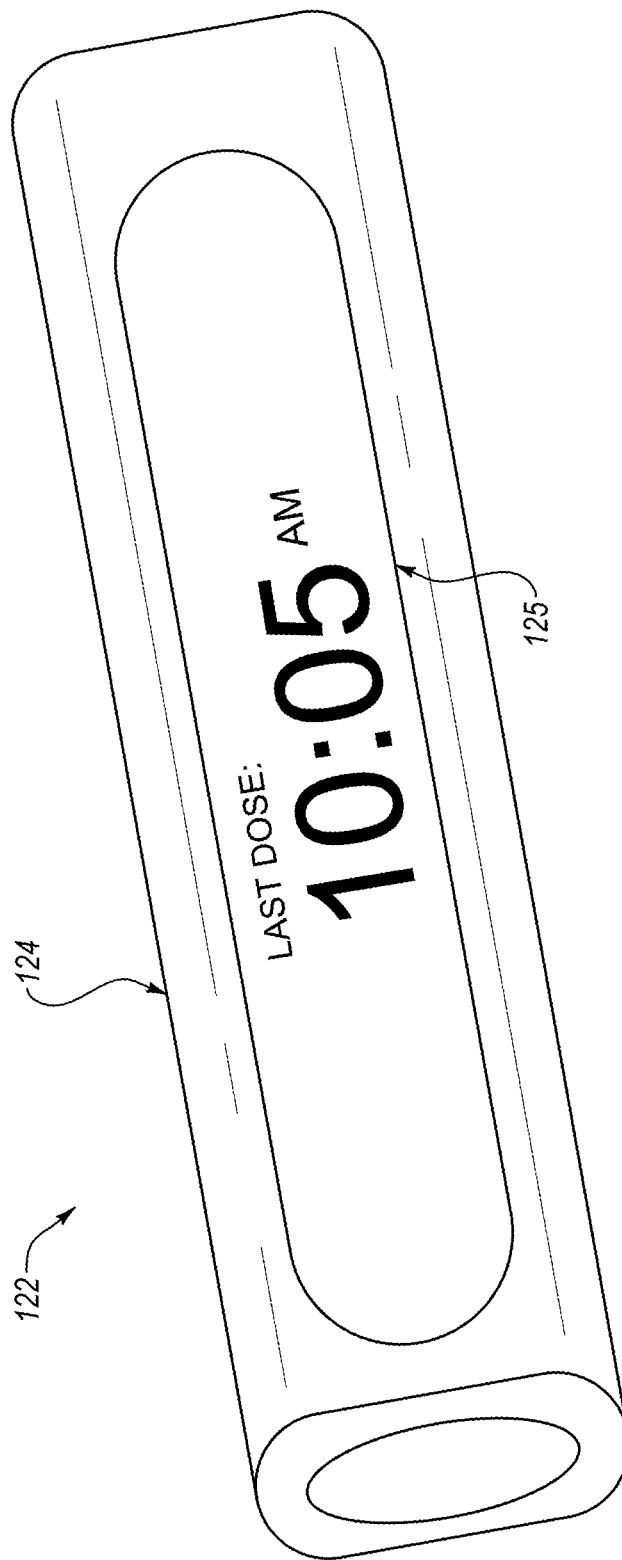
FIGS. 3 through 6 illustrate displays on pen caps according to embodiments of the present disclosure.

FIG. 3 illustrates a display on a pen cap. As shown in FIG. 3, for example, a display 124 on pen cap 122 can depict a time 125 of the most recent dose (e.g., the time and/or date of the last dose), or "last dose," which can assist a user in remembering if they bolus for a recent meal and help a user avoid the unintentional stacking of boluses. In some embodiments, such as cases with pen caps capable of detecting an amount of a dose, the display can additionally display the number of units of the last dose. In some embodiments, the timing of the last dose could be a clock that ticks up to indicate how long ago the last dose was administered. In some embodiments, the display might depict a most recently obtained blood glucose level and the time it was obtained. In some embodiments, the display might be a bistable display, such as an electronic paper display. Electronic paper displays are displays that mimic the appearance of ordinary ink on paper. In some embodiments, the display can include identifying information (e.g., a label identifying the user, such as "Sarah's pen") and/or information about the type of insulin pen that the pen cap is attached to (e.g., the brand of insulin, whether the insulin is rapid-acting or long-acting, etc.). As shown, pen cap 122 can include a button 123, which may be used to wake up (change a mode) the pen cap, toggle between screens, and/or provide other functionality.

Figure 4:
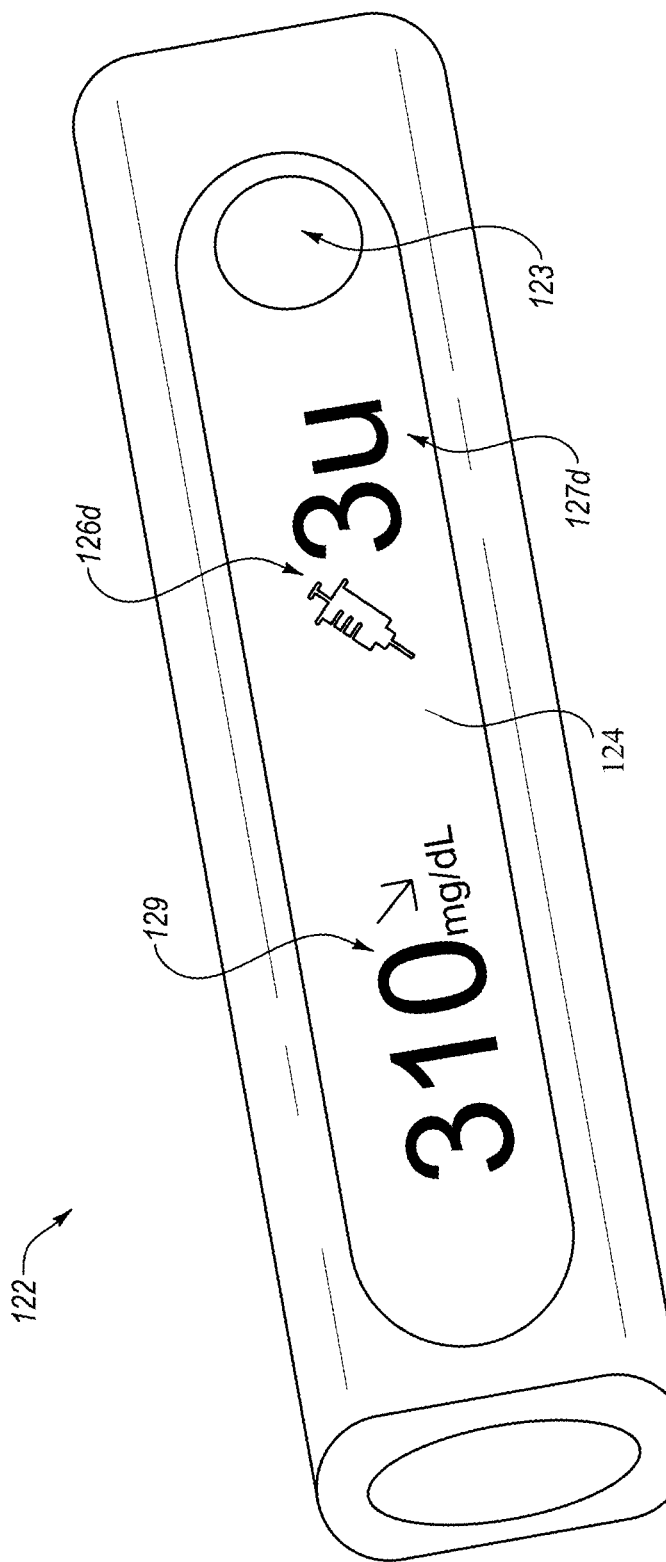

FIG. 4 depicts pen cap 122 showing blood glucose data 129, which can include a current blood glucose level and a trend arrow. The blood glucose level may be received from glucose sensor system 101 after scanning the pen cap 122 as shown in FIG. 2. In some embodiments, placing the pen cap 122 in proximity to the glucose sensor system 101 (e.g., scanning over the glucose monitor 130) may act to wake the pen cap 122 from an idle mode. In some cases, pushing button 123 can wake up the pen cap 122 to allow for a scanning of the glucose sensor system 101. In some cases, removing pen cap 122 from the pen 120 can wake up the pen cap 122 to allow for a scanning of the glucose sensor system 101.

Delivery Recommendations for Rapid Acting

In one embodiment, system 11 and/or system 12 may be configured to provide a correction dose recommendation and present the recommendation at a user interface. Turning to FIG. 4, the display of the pen cap 122 includes a recommended correction dose 127d and a corresponding correction dose icon 126d. If the user's glucose level is in an acceptable range, the pen cap 112 may, responsive to a recommendation system, display information indicating no correction dose is needed. In some embodiments, further input may be entered by or required from the user, such as, for example, an indication of a meal (e.g., where the pen cap 112 may then display a number of meal options, as discussed below) for the user to select. In some cases, button 123 may be progressively pushed to increase the size of the meal, to progressively display larger meal sizes, and/or to highlight different meal sizes. The dosage relating to the meal and any correction dose, if necessary, may be provided to the user along with an indication of the size of the meal. The indication of the size of the meal may be based on a size of an icon, a displayed number of carbohydrates, and/or a label (e.g., Small or S, Medium or M, Large or L). In other embodiments, the meal indicators or icons may be based on other characteristics of the meals, such as, for example, preferred meal selections made by the user, meals having selected nutritional characteristics (e.g., carbohydrates), certain meals based on time of day (e.g., breakfast, lunch, dinner, snack), etc.

A recommended correction dose may only be valid for a set period of time, for example, because blood glucose levels change due to factors such as basal metabolism, meals, and exercise. In one embodiment, the pen cap 122 may be configured to display a recommended correction dose for a set period of time (e.g., a period of time from the last scanning event as shown in FIG. 2). The set period of time may be user defined or it may be determined based on a confidence level that corresponds to the age of the recommendation and physiological factors of the user. Thus, a recommended correction dose may have an associated confidence level and "rate of decay" for that confidence level. After the timer expires (e.g., within the last 5, 10, 15, 20, 30 minutes, or more) the pen cap 122 may stop displaying a recommended correction dose. In some cases, the pen cap 122 may stop displaying a recommended correction dose when a received glucose value expires (e.g., it is more than 10, 15, 20, or 30 minutes old). In various embodiments, glucose data transmitted from a glucose sensor system 101 to a pen cap 122 in a single transmission can include data that may be used by the pen cap to determine at least two estimated glucose values (EGVs) for a time period extending for at least 30 minutes. In some embodiments, a single transmission can include at least 1 hour of glucose data, at least 2 hours of glucose data, at least 4 hours of glucose data, at least 6 hours of glucose data, or at least 8 hours of glucose data. For example, a CGM and/or flash glucose monitor, such as glucose monitor 130, can transmit multiple hours of glucose data in a single transmission event.

In one embodiment, responsive to expiration of the timer, the display 124 on the pen cap 122 may instruct the user that a new blood glucose reading is needed before an updated recommendation may be made based on the blood glucose data. In some cases, a pen cap that does not have current blood glucose data may provide recommendations based on the meal sizes alone, but may optionally additionally include an indication that the recommendation does not include a correction component.

In one embodiment, a correction dose may only be displayed if a current blood glucose value is available (for example, a valid blood glucose value from the previous 10 minutes, from the previous 15 minutes, or from the previous 30 minutes). If no valid blood glucose value is available, a message may be displayed to a user that a current blood glucose value is needed.

Figure 5:
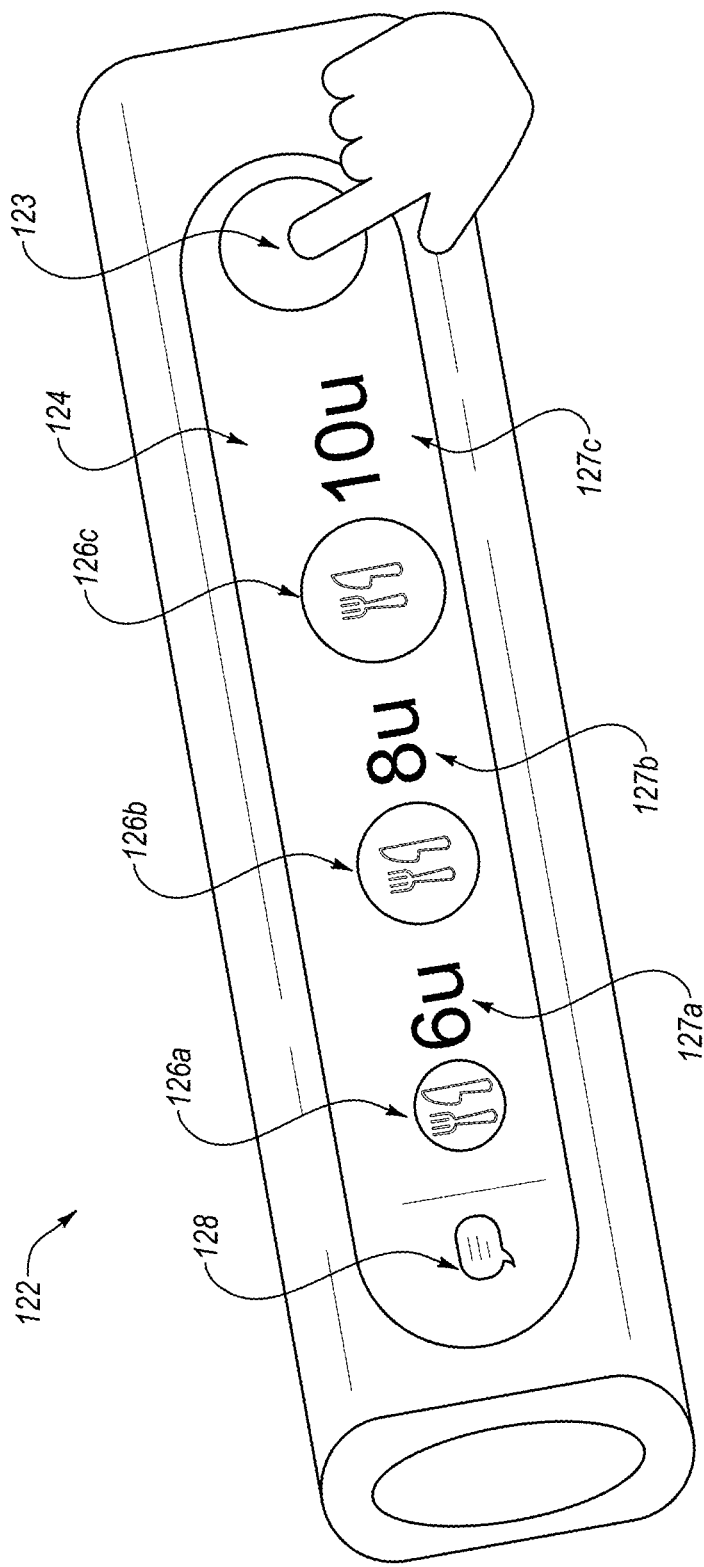

FIG. 5 depicts pen cap 122 with meal-related dosing recommendations (referred to herein as "meal recommendations") 127a-127c, which may be displayed for differently sized meals that are identified by meal icons 126a-126c. For example, in use, a user might press button 123 to obtain meal recommendations after seeing the screen of FIG. 4. In some embodiments, the meal recommendations may be based on meal doses that are set by a healthcare professional, the PWD, and/or a caregiver using the mobile application during set up or as updated by the health care professional, the PWD, and/or caregiver. In some embodiments, the meal recommendations may be based on user-specific dosage parameters that are automatically updated by the system, using any suitable algorithm to update dosage parameters. In some embodiments, when the user has recently (e.g., within the last 5, 10, 15, 20, 30 minutes, or more) obtained a blood glucose reading, meal recommendations 127a-127c can include both a meal dosage and a correction dosage. In some embodiments, the meal recommendations 127a-127c may include only a meal dosage and the pen cap 122 may not require that the user scans a glucose sensor in order to receive the meal recommendations 127a-127c.

In some embodiments, pen caps 112 may refuse to provide a correction dose for a predetermined period of time after a prior dose and/or for a period of time after a prior dose based on a determination of an amount of active insulin (e.g., IOB) in the PWD. In some cases, correction doses may be adjusted based on an estimation of active insulin (e.g., an IOB estimate). In some cases, an IOB may not be known, but an estimated percentage of the prior dose remaining active maybe be determined and displayed to a user. In some cases, a correction dose calculation may be reduced based on an estimated percentage of active insulin remaining being within a predetermined range (e.g., active insulin remaining being determined to be between 5% and 25% results in a 25-75% reduction in correction doses recommended). For example, the pen caps 112 may continue to increase a recommended correction dose over time between hours 2 and 4 after a prior dose based on estimated active insulin percentage in the subject.

Alarms/Alerts Thresholds on Dosing Actions

In some embodiments, if pen cap 122 has identified other recent doses (e.g., by detecting a capping action of the pen cap within the last 3 hours, the last 4 hours, or last 5 hours) without knowing the amount of the dose, the pen cap might refuse (e.g., initially refuse, with an optional override) to add a correction component in order to prevent the unintentional stacking of correction boluses. In some embodiments, meal icons 126a-126c can indicate whether the recommendation includes a correction component or not. In some embodiments, additional icons or displays can indicate if there is a recommended correction dose included and/or the size of the recommended correction dose. In some embodiments, by pushing button 123, the user can obtain a screen that displays the current blood glucose value, trend information (e.g., a trend arrow), and a recommended correction dose. In some embodiments, if there has been a recent dosage of insulin (e.g., within the last 1, 2, 3, or 4 hours) a warning screen might appear next to or over the recommendation to indicate that there has been a recent dose in order to prevent unintentional stacking of insulin. In some embodiments, a notice icon 128 can appear on pen cap 122 in order to indicate to the user that a more detailed suggestion, tip, alert, or alarm is available for the user in the mobile application on the mobile device 140.

Recommendation Specific to Long-Acting Insulin Delivery

Figure 6:
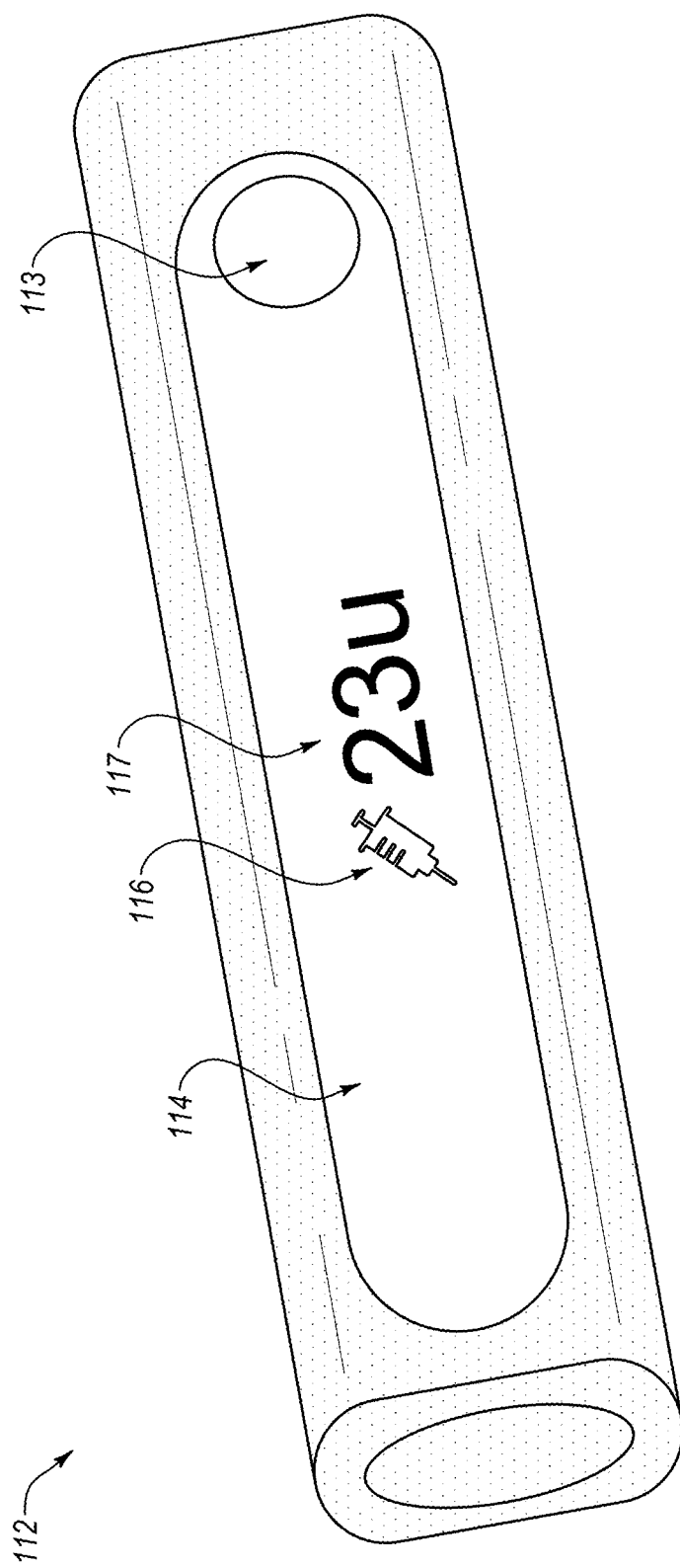

FIG. 6 depicts pen cap 112, which may be used on a long-acting insulin injection pen 110. In some embodiments, pen cap 112 and pen cap 122 may share one or more (e.g., a majority of, all) operational features. As shown in FIGS. 3 through 6, pen caps 112 and 122 can have distinct visual appearances (e.g., different colors, markings, patterns, etc.) or physical structures (shapes, textures, etc.) to assist the user to distinguishing between long-acting insulin and rapid-acting insulin, as the unintentional delivery of the wrong type of insulin can cause hypoglycemic or hyperglycemic events. Pen cap 112 can include a button 113 and a display 114 (e.g., an electronic paper display). When button 113 is pressed by the user (e.g., to wake the pen cap 112), the display 114 can remind the user about the amount of long-acting insulin 117 (with an appropriate icon 116) that the PWD should inject based on stored therapy parameters (e.g., even without having received a blood glucose reading from an associate blood glucose sensor).

In some embodiments, if the user has recently uncapped pen cap 112 from pen 110, the display can depict information about when the pen cap 112 was uncapped or other warnings to prevent the unintentional double delivery of long-acting insulin. In some embodiments, pen cap 112 may provide a notice sound to indicate to a user that it is time to deliver the long-acting insulin based on stored therapy parameters. In some cases, methods, devices, and systems may provide an alarm, alert, or notification to a user (e.g., via a pen cap or via a mobile app) if the user has not taken a dose within a certain threshold period of time of a schedule dose time (i.e., a "missed dose"). In some embodiments, a suitable therapy titration algorithm may suggest that a user change the stored therapy parameters and/or automatically update the stored therapy parameters relevant to the dosing of long-acting insulin.

In some embodiments, long-acting insulin pen cap 112 may infer dosing actions using pen capping information. If a dosing action is not inferred for a certain time or within a certain time range, then pen cap 112 may detect a missed dose of long-acting insulin. A missed dose alarm, alert, and/or notification to a user may be generated and provided to a user. A missed dose notification may include information about the missed dose, including an expected time and an expected amount of long-acting insulin to be delivered.

In some embodiments, a time threshold parameter may be provided that defines a period of time since a last inferred dosing action. The time threshold parameter may be configurable, so a user may set different time periods (e.g., values may be entered by a user or selected from among a list of recommended time periods in a setup screen). If a time since a last inferred dosing action exceeds a time threshold parameter, then a missed dose may be inferred and a missed dose alarm, alert, and/or notification may be generated and provided to a user.

In some embodiments, pen cap 112 can interrogate glucose monitor 130 to receive glucose data and/or receive blood glucose data via the mobile device 140 and/or pen cap 122. In some embodiments, display 114 can depict recent blood glucose data, the time of that data, and/or glucose trend data (e.g., a trend arrow). In some cases, pen cap 122 may be adapted so that it does not display a current blood glucose level in order to avoid a user confusing rapid-acting pen cap 122 with long-acting pen cap 112. In some embodiments, display 114 may include a recommended dose of long-acting insulin 117. In some cases, if a correction dose is needed, pen cap 112 may indicate that the user should also deliver a correction dose of rapid-acting insulin using pen 120.

Therapy Relevant Information

In some embodiments, one or more of the pen caps 112, 122 may track and display the estimated percentage of an administered dose over time. For example, the pen caps 112, 122 may track an estimated percentage of active insulin (e.g., IOB) remaining in a subject over time after each dose has been administered. In some cases, an IOB percentage left indicator may be displayed based on the time of the most recent capping (e.g., immediately after capping an IOB percentage left indicator may indicate that the IOB remaining is 100%, but then be reduced over time after the last capping until it hits zero). In some cases, pen cap 112 can include a rapid-acting insulin active percentage calculation, which may decay over a 3-6-hour period. In some cases, pen cap 122 can include a long-acting insulin active percentage calculation, which may decay over a 12-36-hour period. In some cases, a pen cap adapted for an intermediate-acting insulin may determine a percentage of active intermediate insulin, which may decay over a 6-12-hour period. In some cases, pen caps 112 and/or 122 may be adapted to determine an amount of insulin remaining in an insulin injection pen and thus determine dosage amounts and display a real-time estimation of active insulin as a number of units of insulin for each type of insulin.

Example System Architecture

Figure 7:
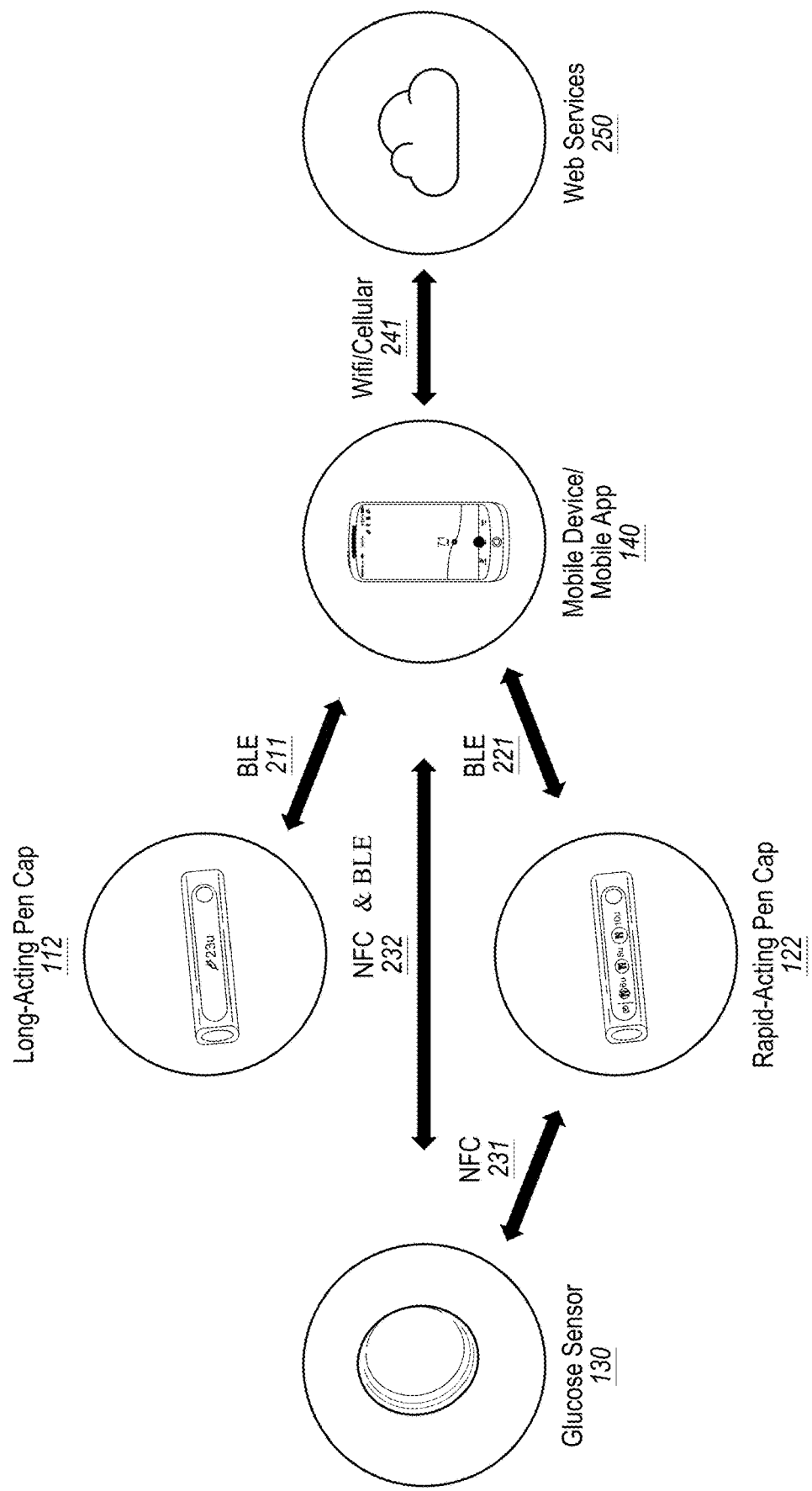
FIG. 7 illustrates example communications architecture for a system according to embodiments of the present disclosure.

FIG. 7 depicts example communications architecture for a system (e.g., the system 11 depicted in FIG. 1B) showing possible communication links between components of the system. The various components can interface with each other via controlled wireless, NFC, or BLE protocols. Each of these components display, transmit, and receive information based on the system workflow in-progress at the specified point in time. As shown, glucose monitor 130 can communicate via NFC with rapid-acting pen cap 122, communication link 231, and/or with mobile device 140, communication link 232. In some cases, a second BLE communication link 232 may be between mobile device 140 and glucose monitor 130, which can permit real-time alarms or alerts based on current blood glucose being received by the mobile device 140 via BLE communications without the need for user action. In some embodiments, long-acting pen cap 112 can communicate with glucose monitor 130 via NFC communications. In some embodiments, long-acting pen cap 112 does not directly communicate with the glucose monitor 130 via NFC (or, in some embodiments, a BGM via BLE), which may prevent user confusion due to the fact that only rapid-acting insulin should be used for a correction or meal dose. In some embodiments, glucose monitor 130 can additionally communicate with the mobile device via a wireless radio that transmits glucose values are predefined intervals. Both pen caps 112 and 122 can communicate with the mobile device 140 via BLE communications. Glucose data, programmed therapy parameters (e.g., daily dosage of long-acting insulin, dosages for different meal sizes (which can vary by time of day), insulin sensitivity factor, carbohydrate-to-insulin ratio, etc.), pen capping data (and, optionally, dosage amount data if detected by the pen caps) may be communicated between the mobile device 140 and each pen cap 112 and 122, and system data may be communicated via WiFi or cellular connection 241 to web service 250 (which may be any remote server). In some embodiments, each pen cap 112, 122 can include a processor and memory configured to run algorithms to determine recommended dosages. In some embodiments, the mobile device 140 can execute therapy recommendation or therapy parameter update algorithms to recommend changes to programmed therapy parameters and/or to automatically update programmed therapy parameters. In some embodiments, web services 250 can execute algorithms to recommend changes to programmed therapy parameters and/or to automatically update programmed therapy parameters. In some embodiments, the timing data from the capping and/or uncapping events (Capping events and uncapping events may, individually, be referred to herein as "capping events." Another event that generates capping information is an uncapping event followed by a recapping event) of the pen caps 112 and 122 may be included in the algorithms for providing therapy recommendations.

In some embodiments, initial therapy parameters may be programmed into the mobile application on mobile device 140 and transmitted to the pen caps 112 and 122 via BLE communication links 211 and 221. In some embodiments, pen cap 122 can use therapy parameters received from the mobile app to recommend correction doses and meal doses. In some embodiments, the therapy parameters can include meal doses for differently sized meals (e.g., small meal, medium meal, and large meal). In some embodiments, the therapy parameters can include a therapy parameter for correcting glucose values, such as an insulin sensitivity factor. In some embodiments, the correction may be based on a linear sliding scale correction, such as discussed below. In some embodiments, pen cap 112 can receive a therapy parameter indicating a daily amount of long-acting insulin. In some embodiments, pen cap 112 can receive recommended times for dosing long-acting insulin from the mobile application of mobile device 140 (e.g., every day at 9 p.m., every day at 8 a.m., twice a day at 8 a.m. and 8 p.m., etc.).

Delivering a Rapid-Acting Insulin Dose

When the user decides to deliver a rapid-acting insulin dose (for example, before a meal), the system can initiate the following workflow. Some of the acts are optional and may not be invoked if particular devices are unavailable or if the user chooses not to use them.

Acquire Glucose Reading

The user may initiate an NFC transfer from the sensor to the rapid-acting insulin smart cap (RCap) by waking up the pen cap and waving it over the sensor, as shown in FIGS. 2 and 3.

After acquiring the glucose reading, the pen cap presents the user with their current glucose value and a trend line, along with a recommended correction dose or action. If there is no glucose value available from within the last ten minutes, the pen cap displays the home screen with no value and the system proceeds to the next step in the workflow when initiated by the user. In some embodiments, as discussed elsewhere, a suggested correction dose may be dependent on pen capping information. For example, in some embodiments, a recommended correction dose for an elevated glucose reading will only be displayed if the pen cap has been on the pen for at least a threshold period of time (e.g., at least 2 hours, at least 3 hours, or at least 4 hours). The time of the last dose may be displayed, which would be based on the most recent capping of the pen cap.

Figure 8:
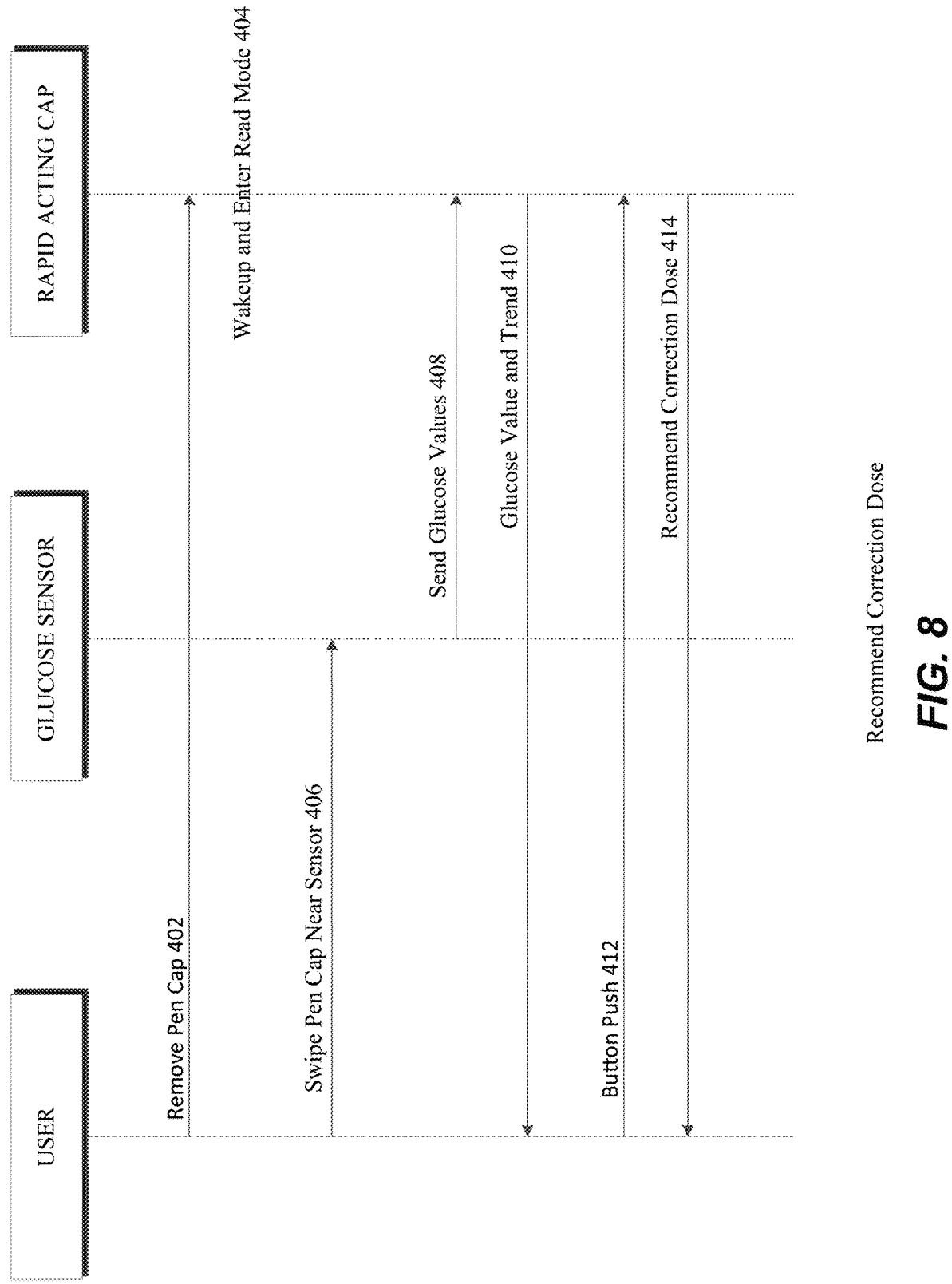
FIG. 8 illustrates a process for recommending an insulin dose according to an embodiment of the disclosure.

FIG. 8 shows a correction dose recommendation process, according to an embodiment of the disclosure. In operation 402, detected removal of a rapid-acting pen cap 122 (e.g., by a user) enables a recommendation mode. In one embodiment, the pen cap 122 may change from a low power mode to an active mode when then pen cap 122 is removed from an insulin pen. In one embodiment, while in the low power mode a pen cap may display information about the last dosing action, for example, the amount of insulin and/or time of the last dose, such as shown at FIG. 3. In operation 404, the pen cap 122, responsive to the uncapping and being waived near the glucose monitor 130, enables an intermediate mode to read the glucose measurements from the glucose monitor 130, and sends a prompt to the user to swipe the pen cap 122 near the glucose monitor 130. In one embodiment, the pen cap 122 may also enable a reader that is configured to interrogate the glucose monitor 130 when the pen cap 122 is near. In one embodiment, the reader may be an NFC antenna that advertises itself as available for BLE communication. In one embodiment, a BLUETOOTH® tag may be coupled to the glucose monitor 130 that may communicate with the reader responsive to the advertisement. In operation 406, the glucose monitor 130 provides the blood glucose measurements to the pen cap 122 responsive to an interrogation, and the pen cap 122 decodes the received measurements. In one embodiment, the glucose measurements may be encrypted or encoded using a proprietary format. In operation 408, the user pushes button 123 and the pen cap 122 enables a correction dose recommendation mode responsive to the user asserting the button. In operation 410, the pen cap 122 recommends a correction dose at a display on the pen cap 122. In one embodiment, the correction dose is determined at the pen cap 122. In another embodiment the correction dose is determined at another device, such as the mobile device 140 and communicated to the pen cap 122. In various embodiments, the pen cap 122 may be configured to toggle back and forth between a glucose read mode and recommendation mode, and a user may be able to receive current measurements and current recommendations. The pen cap 122 may be configured to change back to a low power mode responsive to a time-out.

User Assessment of Glycemic Impact of Meal (Optional)

If the user intends to dose for a meal, they move to the next screen and are presented with three different dose recommendations, for meals that will have a small, medium, or large impact on their blood sugar. These recommendations may change over time to adapt to the user's habits and physiology. The recommended doses include a correction based on the user's glucose reading, if applicable.

Inject Rapid-Acting and Capture Insulin Dose

The user removes the RCap from the insulin pen and installs the needle onto the insulin pen. The needle is primed and then the user dials their desired dose and injects the insulin. The user removes the needle and replaces the cap on the rapid-acting insulin pen. The glucose values (if applicable) are transmitted via BLE to the mobile app where they are stored locally on a smartphone. When a connection to the cloud is available via cellular or WiFi, the data is then synced to the cloud. In some embodiments, a portion of the system (e.g., the cap, the mobile application) may monitor use of the pens (e.g., based on data inputted by the user regarding usual use of the devices) to detect priming actions (e.g., clicks, such as two sets of clicks, from the pen and/or input from the user regarding the priming or lack thereof) and/or selection of dosages. In some cases, methods, systems, and devices provided herein can detect a needle presence to infer priming behavior (i.e., assume priming if the needle was removed and replaced). In some cases, methods, systems, and devices provided herein can assume priming based on dose volume and expected glucose impact.

Figure 9:
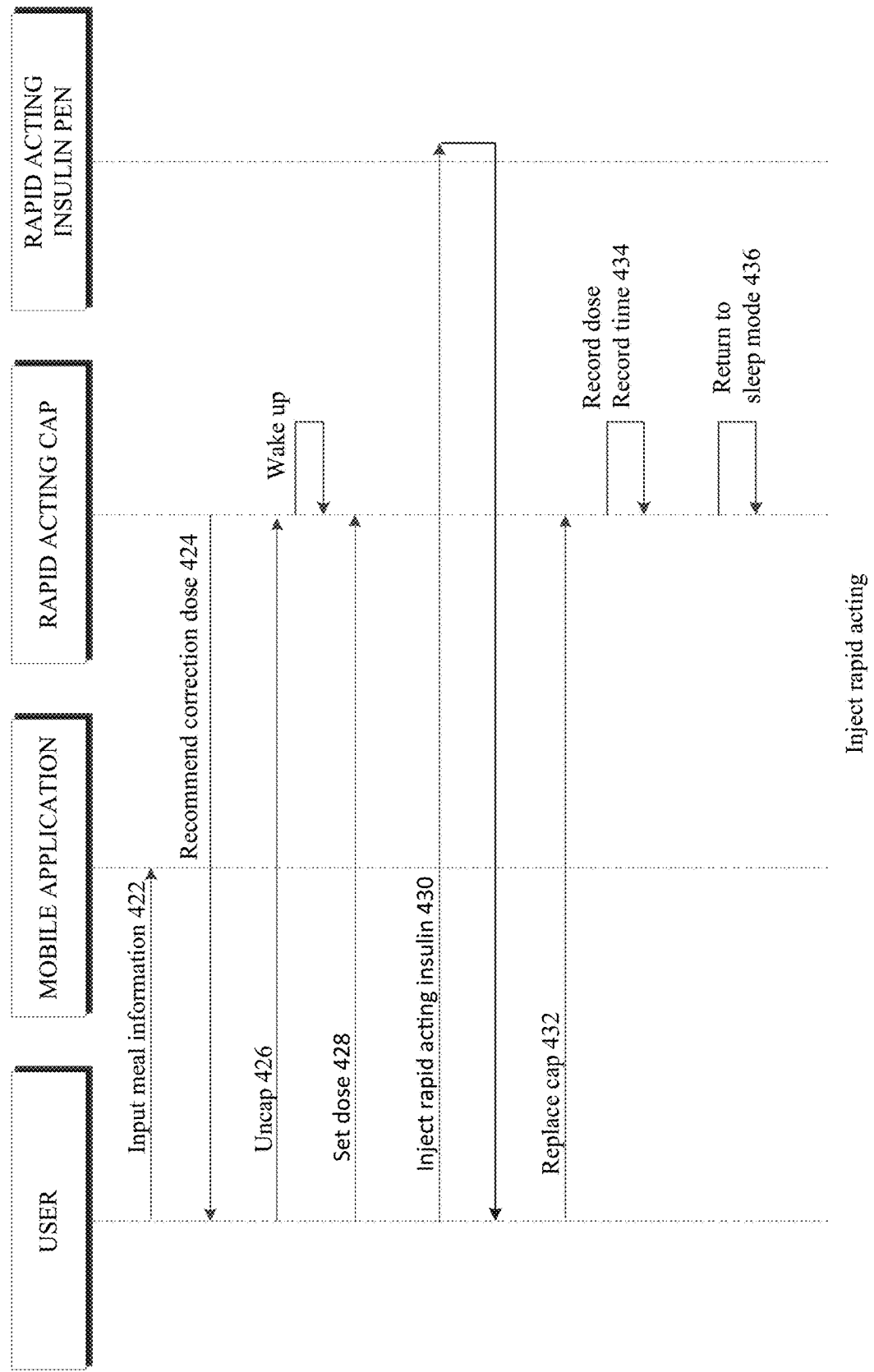
FIG. 9 illustrates a process for injecting insulin according to an embodiment of the disclosure.

FIG. 9 shows a rapid-acting dose injection process according to an embodiment of the disclosure. In operation 422, the user activates the mobile application and inputs meal information. In operation 424, the mobile application presents one or more correction dose recommendations to the user. In one embodiment, the recommendations are based on a sliding scale of aggressiveness. In one embodiment, the recommendations may be based on a low, medium, or high glycemic impact of the meal information input by the user. In another embodiment, the recommendations may be based on a glucose reading and the recommendations may be based on a degree of confidence that the glucose reading is not too old. For example, if three recommendations are presented, the first recommendation may correspond to a high degree of confidence that the last glucose reading is still valid. The second recommendation may correspond to a medium degree of confidence that the last glucose reading is still valid. The third recommendation may correspond to a low degree of confidence that the last glucose reading is still valid. In operation 426, the user uncaps the pen cap 122, which is detected by the pen cap 122. In operation 428, the user primes the insulin injection pen 120 to deliver a dose amount. In operation 430, the user injects a dose of insulin from the insulin injection pen 120. In operation 432, the user replaces the pen cap 122, which the pen cap 122 detects. In operation 434, the pen cap 122 records the dose action and time of dose action responsive to the detected capping event. In operation 436, the pen cap 122 returns to a low power mode responsive to the capping event.

Delivering a Long-Acting Insulin Dose

When the user decides to deliver a long-acting insulin dose, the system initiates the following workflow. Some of the steps are optional and may not be invoked if particular devices are unavailable or if the user chooses not to use them.

Acquire Glucose Reading

The user may initiate an NFC transfer from a glucose sensor (typically a CGM) to the long-acting insulin pen cap 112 by waking up the pen cap and waving it over the sensor.

After acquiring the glucose reading, the pen cap presents the user with their current glucose value and a trend-line, along with a recommended long-acting insulin dose. If there is no glucose value available from within the last ten minutes, the pen cap displays only the long-acting insulin dose recommendation, which is tailored to the user's habits and physiology and may change over time with clinician oversight and approval.

Figure 10:
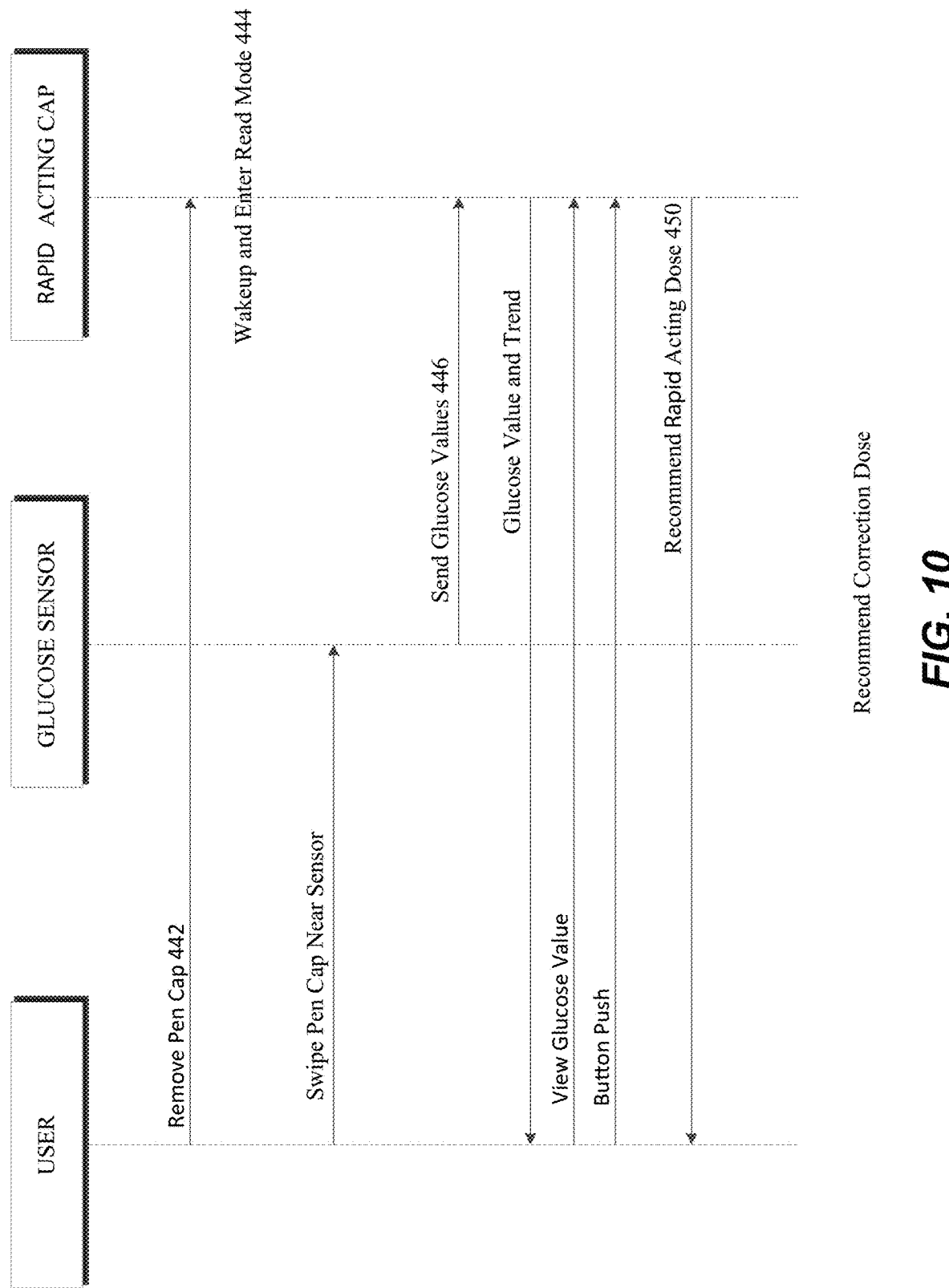
FIG. 10 illustrates a process for recommending an insulin dose according to an embodiment of the disclosure.

FIG. 10 shows a correction dose recommendation process, according to an embodiment of the disclosure. In operation 442, a user removes a pen cap 112 to enable a recommendation mode. The pen cap 112 may change from a low power mode to an active mode when the pen cap 112 is removed from the insulin pen. In one embodiment, while in the low power mode a pen cap may display information about the last long-acting insulin dosing action, for example, the amount of insulin and/or time of the last dose, such as shown at FIG. 3. In operation 444, the pen cap 112, responsive to the uncapping and being waived near the glucose monitor 130, enables an intermediate mode to read the glucose measurements from the glucose monitor 130, and sends a prompt to the user to swipe the pen cap 112 near the glucose monitor 130. In one embodiment, the pen cap 112 may also enable a reader that is configured to interrogate the glucose monitor 130 when the pen cap 112 is near. In one embodiment, the reader may be an NFC antenna that advertises itself as available for BLE communication. In one embodiment, a BLUETOOTH® tag may be coupled to the glucose monitor 130 that may communicate with the reader responsive to the advertisement. In operation 446, the glucose monitor 130 provides the blood glucose measurements to the pen cap 112 responsive to an interrogation, and the pen cap 112 decodes the received measurements. In one embodiment, the glucose measurements may be encrypted or encoded using a proprietary format. In operation 448, the user pushes button 113 and the pen cap 112 enables a correction dose recommendation mode responsive to the user asserting the button. In operation 450, the pen cap 112 recommends a correction dose at a display on the pen cap 112. In one embodiment, the correction dose is determined at the pen cap 112. In another embodiment the correction dose is determined at another device, such as the mobile device 140 and communicated to the pen cap 112. In various embodiments, the pen cap 112 may be configured to toggle back and forth between a glucose read mode and recommendation mode, and a user may be able to receive current measurements and current recommendations. The pen cap 112 may be configured to change back to a low power mode responsive to a time-out.

Inject Insulin Dose

The user removes pen cap 112 from the insulin pen and installs the needle onto the cartridge. The needle is primed and then the user dials their desired dose and injects the insulin. The user removes the needle and replaces the cap on the rapid-acting insulin pen. The glucose values (if applicable) are transmitted via BLE to the mobile app where they are stored locally on a smartphone. When a connection to the cloud is available via cellular or WiFi, the data is then synced to the cloud. In some embodiments, a portion of the system (e.g., the cap, the mobile application) may monitor use of the pens (e.g., based on data inputted by the user regarding usual use of the devices) to detect priming actions (e.g., clicks, such as two sets of clicks, from the pen and/or input from the user regarding the priming or lack thereof) and/or selection of dosages.

Figure 11:
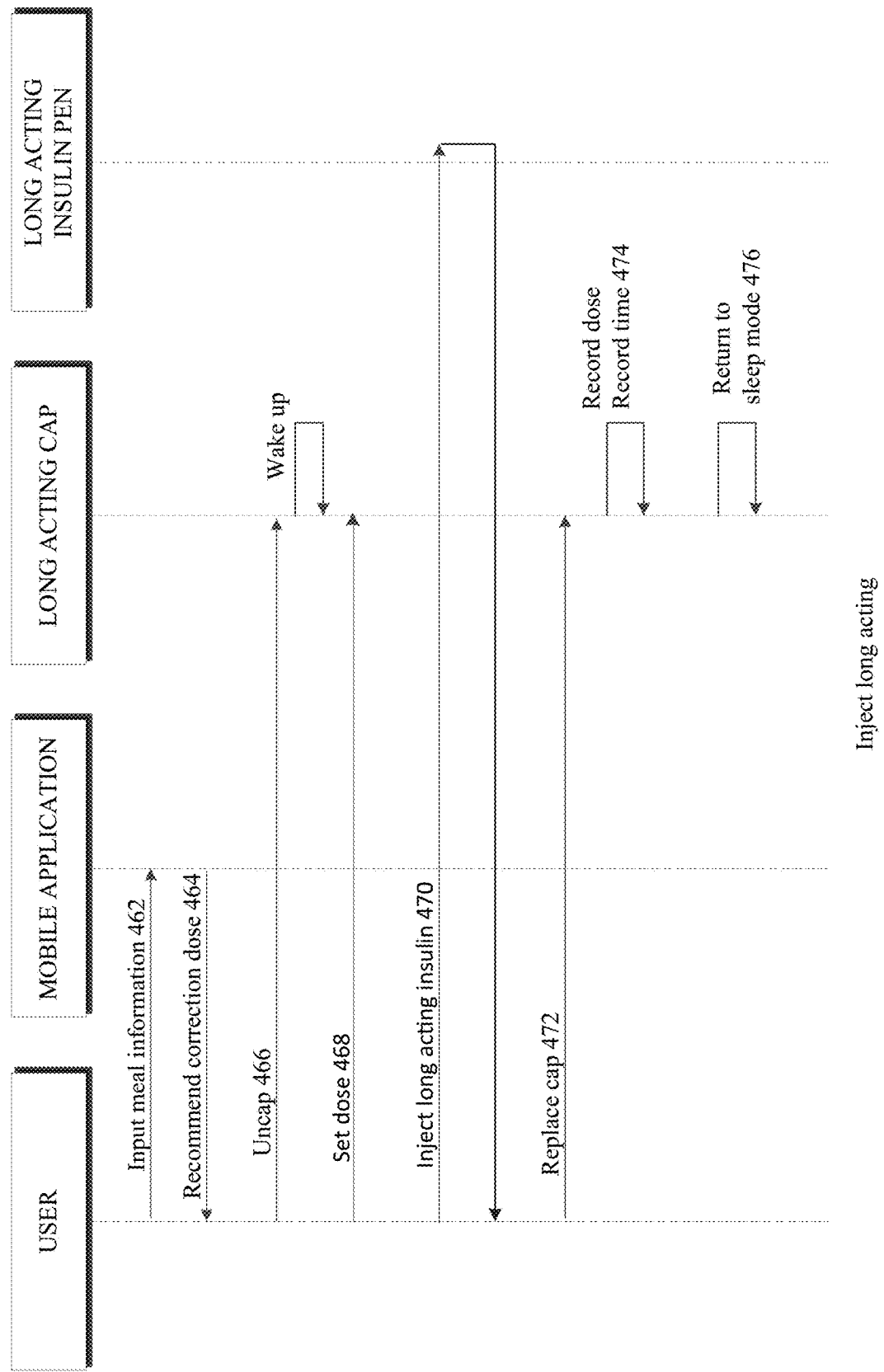
FIG. 11 illustrates a process for injecting insulin according to an embodiment of the disclosure.

FIG. 11 shows a rapid-acting insulin injection process according to an embodiment of the disclosure. In operation 462, the user activates the mobile application and inputs meal information. In operation 464, the mobile application presents one or more correction dose recommendations to the user. In one embodiment, the recommendations are based on a sliding scale of aggressiveness. In one embodiment, the recommendations may be based on a low, medium, or high glycemic impact of the meal information input by the user. In another embodiment, the recommendations may be based on a glucose reading and the recommendations may be based on a degree of confidence that the glucose reading is not too old. For example, if three recommendations are presented, the first recommendation may correspond to a high degree of confidence that the last glucose reading is still valid. The second recommendation may correspond to a medium degree of confidence that the last glucose reading is still valid. The third recommendation may correspond to a low degree of confidence that the last glucose reading is still valid. In operation 466, the user uncaps the pen cap 112, which is detected by the pen cap 112. In operation 468, the user primes the long-acting insulin injection pen 110 to deliver a dose amount. In operation 470, the user injects a dose of insulin from the insulin injection pen 110. In operation 472, the user replaces the pen cap 112, which the pen cap 112 detects. In operation 474, the pen cap 112 records the dose action and time of dose action responsive to the detected recapping event. In operation 476, the pen cap 112 returns to a low power mode responsive to the capping event.

Checking Status on Rapid-Acting Pen Cap and Long-Acting Pen Cap

Figure 12:
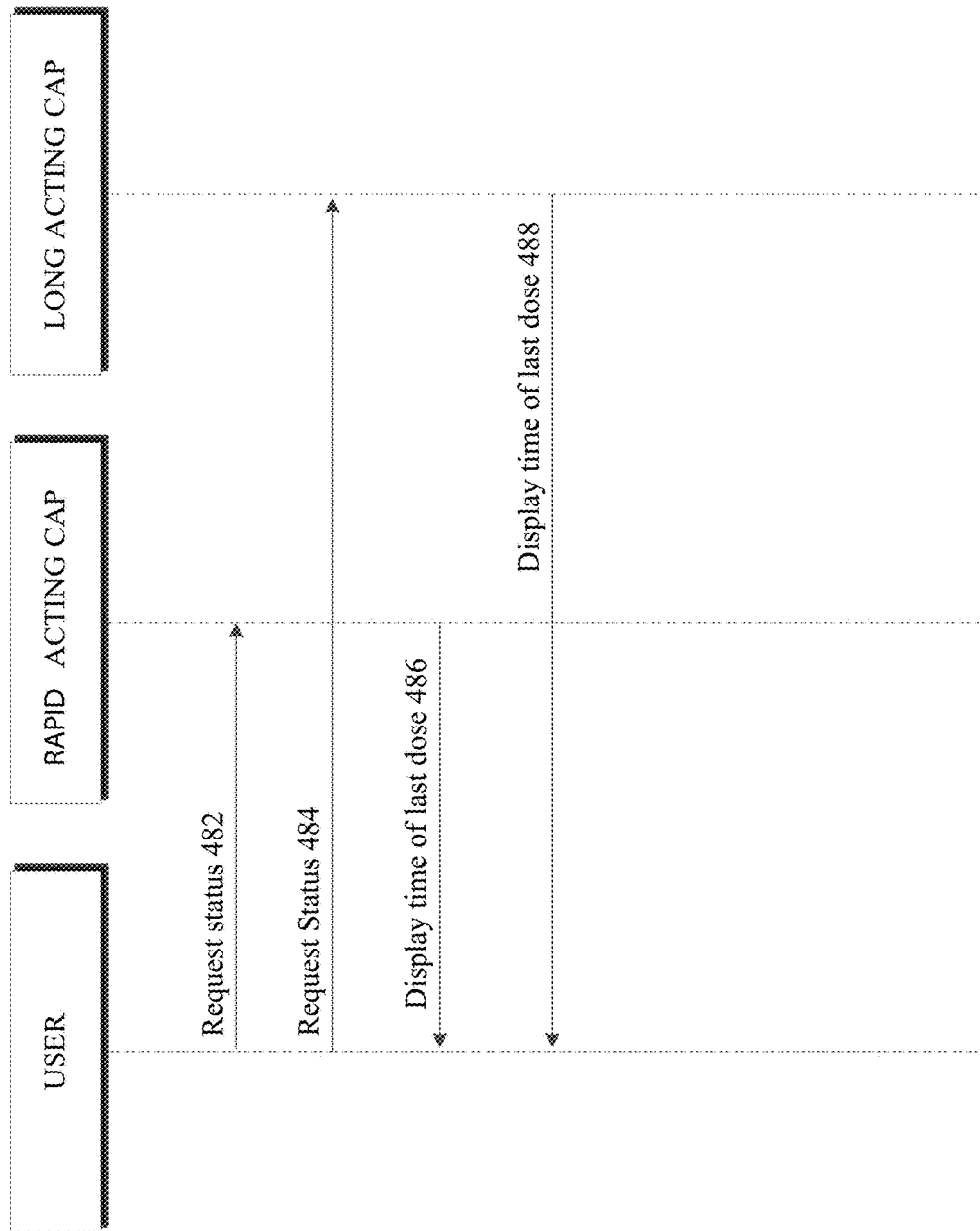
FIG. 12 illustrates a process for checking the status of a therapy system according to an embodiment of the disclosure.

FIG. 12 shows a status check at the pen caps 112 and 122 according to an embodiment of the disclosure. By way of example, status information may include the date and time of the last rapid-acting dose, a glucose trend-line, most recent glucose reading and time, and recommended correction doses. In operation 482 the user requests a status check from the pen cap 122 associated with rapid-acting insulin delivery. In operation 484, the user requests a status check from the pen cap 112 associated with long-acting insulin delivery. In operation 486, the pen cap 122 may display the status information responsive to the user's request. In some embodiments, the pen cap 122 may persistently display the date and time of the last rapid-acting dose when it is in a low power mode. In operation 488, the pen cap 112 may display the status information responsive to the user's request. In some embodiments, the pen cap 112 may persistently display the date and time of the last long-acting dose when it is in a lower power mode.

Checking System Status

Figure 13:
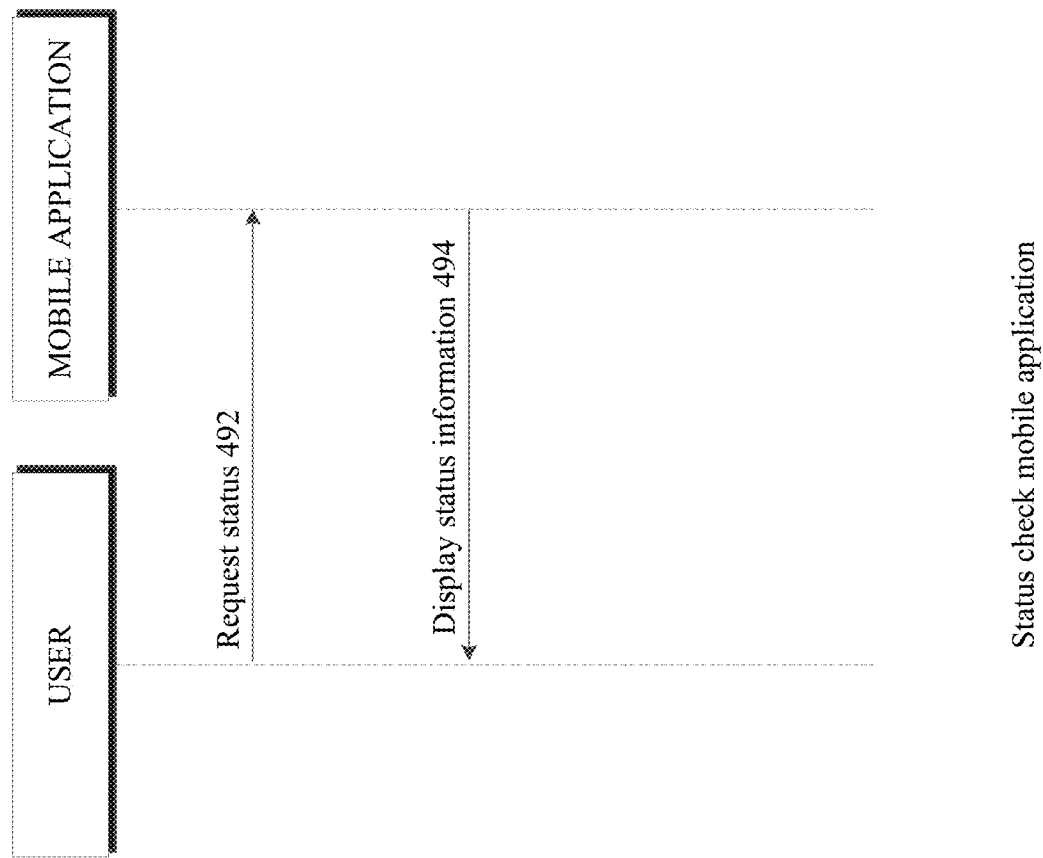
FIG. 13 illustrates a process for checking the status of a therapy system according to an embodiment of the disclosure.

The user can check system status in the following locations:

FIG. 13 shows a status check at the mobile application according to an embodiment of the disclosure. By way of example, status information may include system maintenance information (power remaining, insulin remaining, sensor status etc.) the date and time of the last rapid-acting dose or long-acting dose, a glucose trend-line, most recent glucose reading and time, detailed forecasts and trends, and recommended correction doses. In operation 492A, the user requests a status check from the mobile application. In operation 494A, the mobile application may display the status information responsive to the user's request.

Figure 15:
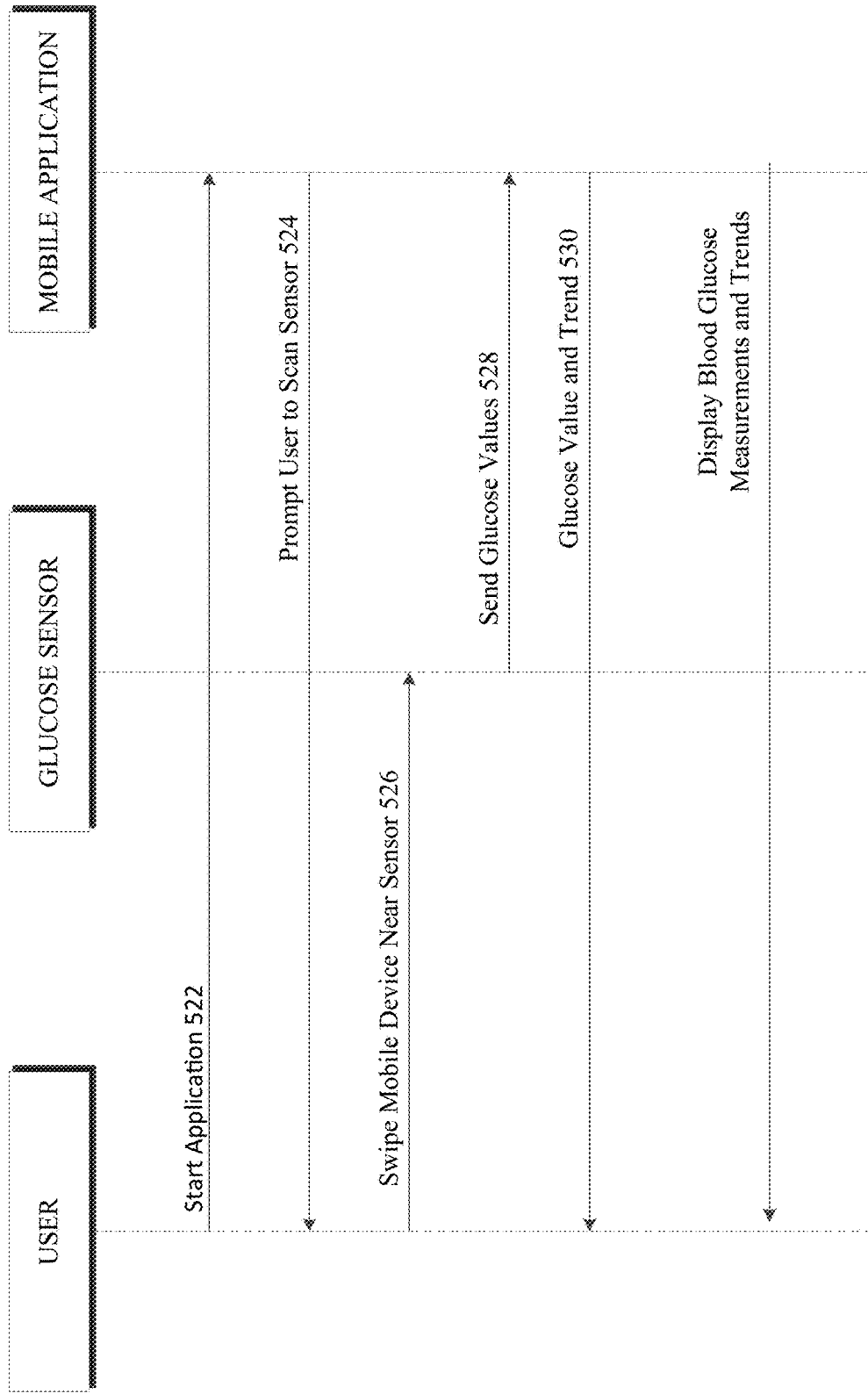
FIG. 15 illustrates a process for checking the status of a therapy system according to an embodiment of the disclosure.

FIG. 15 shows a process for checking the status of the system, according to an embodiment of the disclosure. In operation 522, the mobile application 104 is started. In operation 524, the mobile application 104 presents a prompt for a user, the prompt being to scan the glucose sensor system. In one embodiment, the mobile application 104 may present the prompt responsive to a request received at the user interface to check system status. In operation 526, the mobile device running the mobile application 104 is swiped near one or more glucose sensors. In operation 528, the mobile application 104 receives blood glucose data from the one or more glucose sensors. In operation 530, the mobile application 104 determines and presents glucose data and trends, typically for a recent time window.

Mobile Application User Interface

Methods and systems provided herein can additionally include a mobile application that runs on a mobile device (e.g., a smartphone or tablet) that is in wireless communication (e.g., via BLE) with one or more pen caps described herein. In some embodiments, blood glucose data may be transmitted from a glucose sensor system 101 (e.g., from a glucose monitor 130 and/or a blood glucose meter 150), either via the pen caps and/or directly from the glucose sensor system. In some embodiments, a mobile application can have a user interface that displays a graphical representation of the blood glucose data. In some embodiments, a graphical display of blood glucose data over time can include indicators communicating pen capping information.

Figure 16:
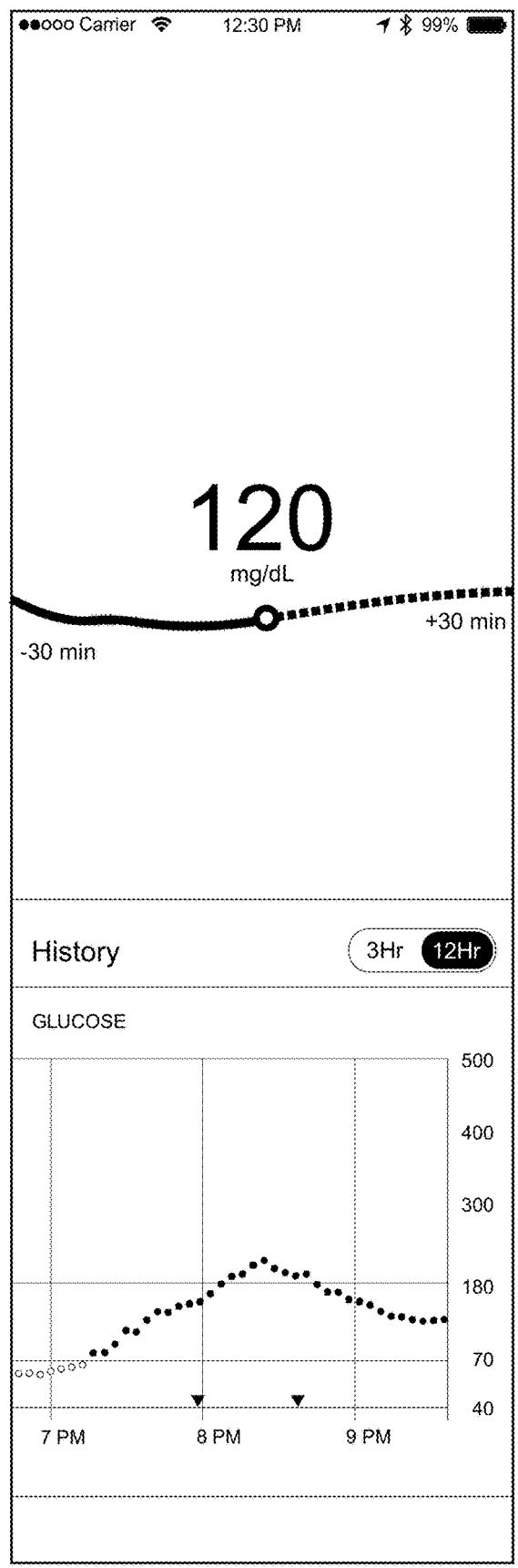
FIGS. 16 through 25 illustrate example displays and/or user interfaces of a portion of the system (e.g., of the mobile device) according to embodiments of the present disclosure.

FIG. 16 shows an example display of the system (e.g., of the mobile device). For example, FIG. 16 shows an example user interface for a mobile application that includes a graphical presentation of blood glucose data with markings (e.g., triangles, circles, wedges, or any other suitable icon or indication of a dose) along the x-axis showing the timing of certain actions, such as, for example, re-capping actions, which may be assumed to be the timing of an insulin dosage, and/or other actions, such as the timing of glucose readings. In some embodiments, if an uncapping is prolonged (e.g., if the pen is left uncapped for a long period of time before the pen cap is re-capped), the triangle may be wider to indicate the time during which a dose of insulin might have been administered. In some embodiments, the icons may be different (e.g., different colors or shapes) depending on the type of insulin associated with the pen cap that had a re-capping action. In some embodiments, a graphical presentation of blood glucose levels may be toggled between a 3-hour and a 12-hour time frame. In some embodiments, a home screen can include a simplified presentation of the current EGV, a curve shown prior to 30 minutes of the EGVs, and a curve showing projected EGVs over the next 30 minutes.

Messages may be displayed on the home screen to provide the user with reminders about recommended actions that the user might take to improve their therapy. In some embodiments, a mobile app may provide coaching to a user based on a combination of the glucose data and/or pen capping information. In some embodiments, coaching via the app may be approved by a healthcare professional via a cloud connection before it is provided to the user. For example, in some embodiments, blood glucose data after a capping action may indicate that the user is typically under dosing or typically overdosing insulin for particular meals. In some embodiments, methods and systems provided herein can then adjust the user-specific therapy parameters or recommended dose amounts for rapid-acting insulin based on blood glucose data after each capping event. In some embodiments, glucose data after or surrounding each capping event may be sent to a healthcare professional to have the healthcare professional update user-specific dosage parameters or recommended dose amounts for that user, which may be based on the time of day. In some embodiments, data surrounding each capping event may indicate that the user is typically dosing rapid-acting insulin after the meal has begun, and might be adapted to coach the user to pre-bolus for meals when the user intends to eat. In some embodiments, data surrounding each capping event along with blood glucose levels may be utilized to recommend injection timings relative to when a meal is begun after the injection. In some embodiments, data surrounding each capping event and/or blood glucose levels may be utilized to recommend the modifications of doses of insulin taken by the subject. Again, such coaching may be automatic, approved by the healthcare professional, and/or developed by a healthcare professional.

In some embodiments, blood glucose levels may further be utilized to track and/or make recommendations for the type of insulin being taken. In some cases, blood glucose levels may be analyzed in conjunction with dose capture data to determine if the wrong insulin was taken. In some cases, blood glucose data in combination with temperature sensor data from a pen cap may be analyzed to determine if the insulin has gone bad, if the wrong insulin was taken (e.g., as discussed above), or if there are other issues with the therapy or associated devices.

The mobile application may be adapted to enable the user to provide additional information that may be used to determine how often the user is following the recommended doses. In some embodiments, a user may be provided with the possibility to input dose amounts for each capping event and/or may input multiple doses (e.g., an amount of insulin taken throughout a selected period of time, such as, over a day) into the mobile application or directly into the pen cap. For example, the markings along the graph may be tapped by a user to allow a user to enter to dose administered.

Figure 17:
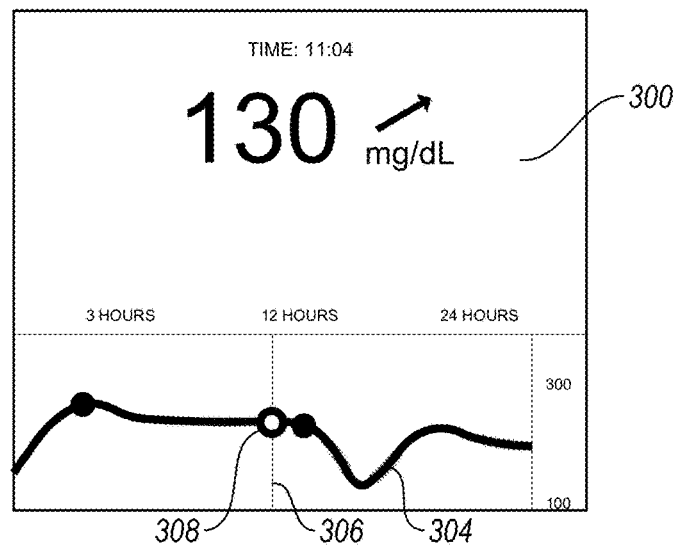

FIG. 17 illustrates another example display 300 of a portion of the system (e.g., of the mobile device, such as mobile device 140 shown in FIG. 7). As shown in FIG. 9, the display 300 may be somewhat similar to that shown in FIG. 16 and may include a graphical presentation of blood glucose data with markings (e.g., circles 302) along the x-axis showing the timing of events relating to the system 10, such as, for example, the timing that glucose readings are received from an associated glucose monitor (e.g., a flash monitor). The circles 302 may be connected by (e.g., may overlie) a trend line 304 of the user's blood glucose levels.

In embodiments where data is only intermittently received from a blood glucose monitor (e.g., where segments or blocks of data regarding BGVs are downloaded at discrete time periods on demand), the data preceding the current data point circle 302 indicating the latest glucose reading (e.g., the area between the current circle 302 and the immediately preceding circle 302) may be received from the glucose monitor and populated into the trend line 304. In some embodiments, another marker (e.g., a most recent circle 306) may be positioned at the latest reading (e.g., the most recent circle 302) and may be visually distinct from the preceding circles 302. In some embodiments, the time of the last scan may be displayed on the display 300. In some embodiments, the horizontal position on the trend line 304 of the most recent circle or marker 306 may also be indicated on the display 300 with a marker (e.g., vertical line 308).

In some embodiments, the pen cap may query the blood glucose sensor when the device is placed near the sensor and/or when a button (e.g., a virtual scan sensor button 310)

is selected or pushed (e.g., and held) by a user. In some embodiments, the display 300 may include an indicator (e.g., meter 312 extending around the user button 310) that displays a measurement related to the system. For example, the meter 312 may display the remaining lifespan of the blood glucose sensor (e.g., the estimated time before the sensor needs to be replaced). As depicted, the meter 312 may increase (e.g., grow) or decrease (e.g., recede) around the button 310 as the related data changes. For example, the meter 312 may decrease or increase over time as the lifespan of the blood glucose sensor approaches zero (e.g., resulting in either a full meter 312 or an empty or outlined meter 312). In some embodiments, the meter 312 may display other metrics, such as, for example, time since last scan, time until next recommend scan, the percentage remaining of a previously administered dose (e.g., a correction dose), etc.

Figure 18:
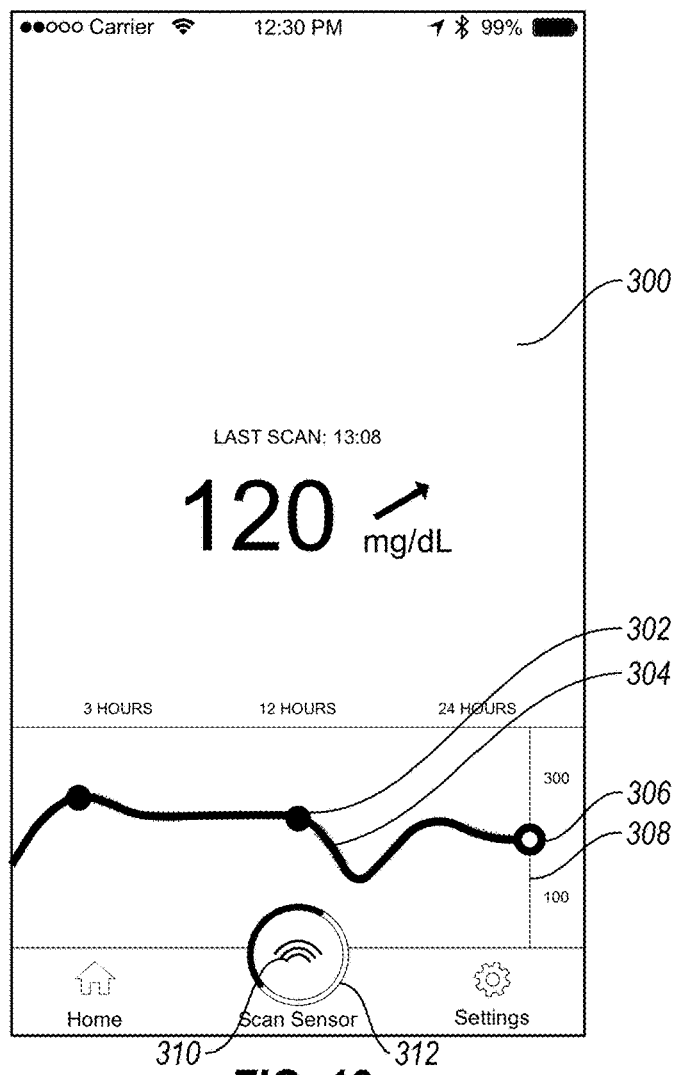

As shown in FIG. 18, in some embodiments, the display 300 may enable the user to track previous values on the trend line 304. For example, the user may drag the most recent circle or marker 306 (e.g., along with the vertical line 308) backward along the trend line to a previous time period. As depicted, the display 300 may track the position of the most recent circle 306 and display the time and blood glucose level of the selected time period.

In some embodiments, the most recent circle 306 (e.g., along with the vertical line 308) may be anchored to the most recent data position of the trend line 304 and may jump back to the most current position once the most recent circle 306 is released by the user. For example, the vertical line 308 may be deformed into a "slingshot" and spring the circle 306 back to the most current reading position when released by the user.

Figure 19:
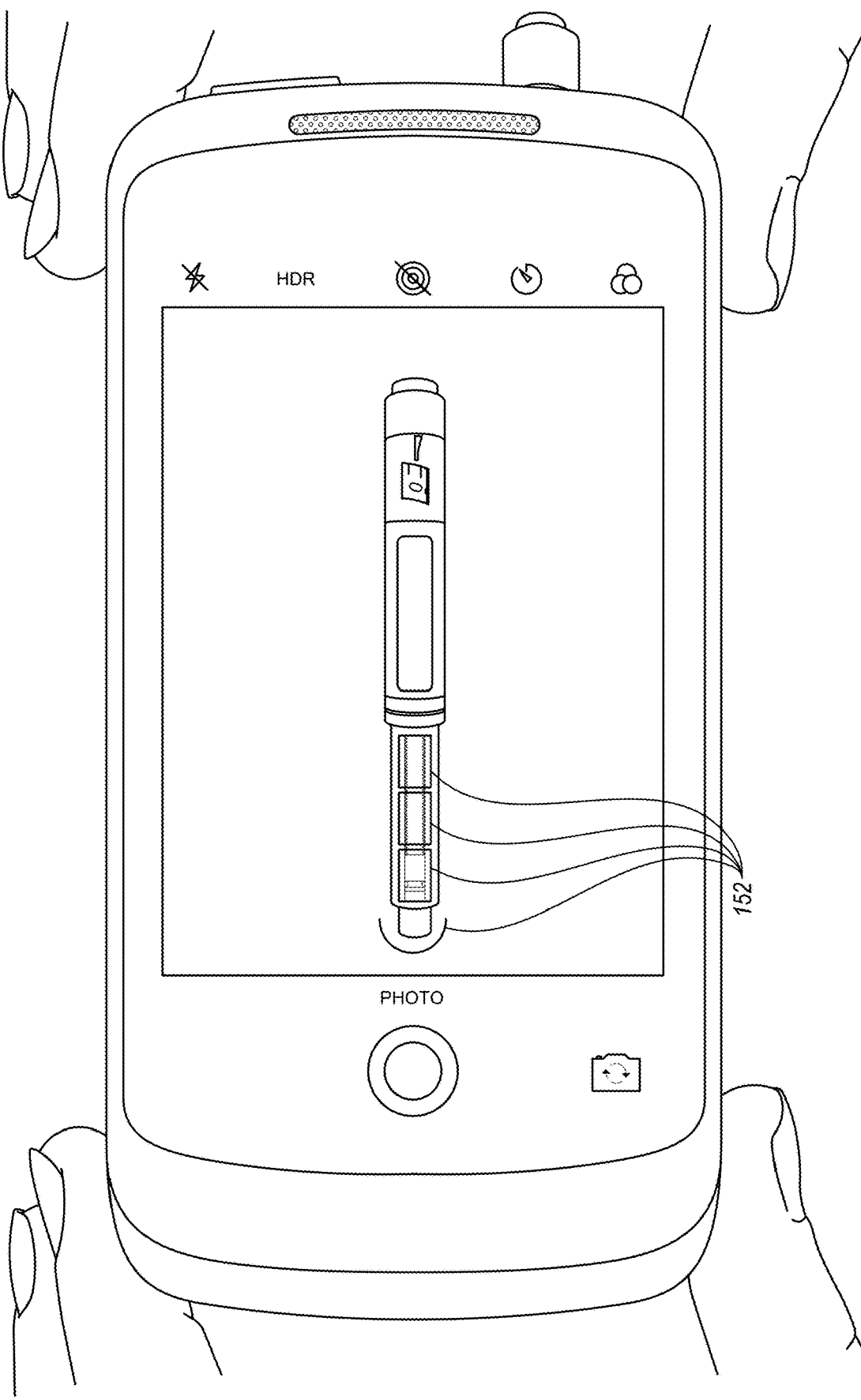

In some embodiments, a user might be asked to estimate a number of units of insulin remaining in a pen every so often. In some embodiments, a user might be asked to take a photo of the insulin pen and the app might be adapted to analyze the image of the insulin pen to determine an approximate number of units left in the pen. For example, FIG. 19 shows an example user interface where a user might use the smartphone's camera to take a picture of the pen. In some embodiments, the user interface may overlay the real time view of the smartphone's camera with guiding lines that correspond to features on the pen in order to assist the user with aligning the pen with the smartphone's camera. In some embodiments, the mobile app may be adapted to automatically snap a picture of the pen when features in view of the smartphone's camera align with the guiding lines 152. As shown, the guiding lines 152 can include lines showing windows in the pen that permit the viewing of plunger. In some embodiments, the guiding lines can move in relationship to the position of the pen. In some embodiments, the mobile app can detect if the pen is too close or too far away from the camera to instruct the user to move the pen relative to the smartphone's camera. In some embodiments, the camera can automatically zoom in on the pen. In some embodiments, a user might be asked to estimate how often the user follows the recommended doses. In some embodiments, the device may automatically analyze the amount of insulin when the pen or a portion thereof is in view of the mobile device (e.g., the camera).

In one embodiment, the device may automatically analyze an insulin vial and infer meal information based on changes to an image of the insulin vial. For example, based on several successive images, meal intake and mealtimes may be inferred based on changes in the amount of insulin in a vial and the type of insulin (i.e., rapid acting).

In some embodiments, the pen may include indicators (e.g., graduated markings) that enable a user to easily identify a position of a portion of the pen (e.g., the plunger) and input an associated value into the application.

Pen caps may be configured to gain insights into which recommended dose the user is likely to be following. For example, as described in U.S. patent application Ser. No. 15/717,805, filed Sep. 27, 2017, entitled "Medicine Injection And Disease Management Systems, Devices and Methods," the contents and disclosure of which is hereby incorporated by reference in its entirety, a pen cap (whether or not there is any dose capture feature incorporated into the pen cap) can include meal announcement categorizations (such as S, M, L) and data from each announcement might indicate whether the user is likely to have dosed an appropriate amount for a S, M, or L meal. In some embodiments, a button on pen cap 122 might be pressed multiple times to show recommendations for successively a S meal, a M meal, and a L meal, and methods and systems provided herein may assume that the user dosed insulin based on the last displayed recommendation. In some embodiments, information added via the mobile application indicating an amount of insulin left in the pen at various intervals (once a day, once every few days, once a week) can indicate whether the user is generally following the therapy recommendations or whether the user is ignoring them. In some embodiments, methods and systems provided herein can analyze glucose data, pen capping information, data regarding amounts of insulin left in one or more pens, and/or answers to questions presented via the mobile app to determine a likelihood or rating of the user's conformance to recommended doses, which may be used by methods and systems provided herein to determine whether to adjust the recommended doses or to provide coaching to the user.

System Setup

Therapy management systems provided herein may be set up using any suitable method. In some embodiments, a health care professional can input initial therapy parameters from a web portal or directly into a user's mobile device (e.g., during an appointment). In some embodiments, the user may input initial therapy parameters based on advice from a doctor. Therapy management systems provided herein provide a way for users to clearly understand their therapy settings so that they gain trust in the system.

Figure 20:
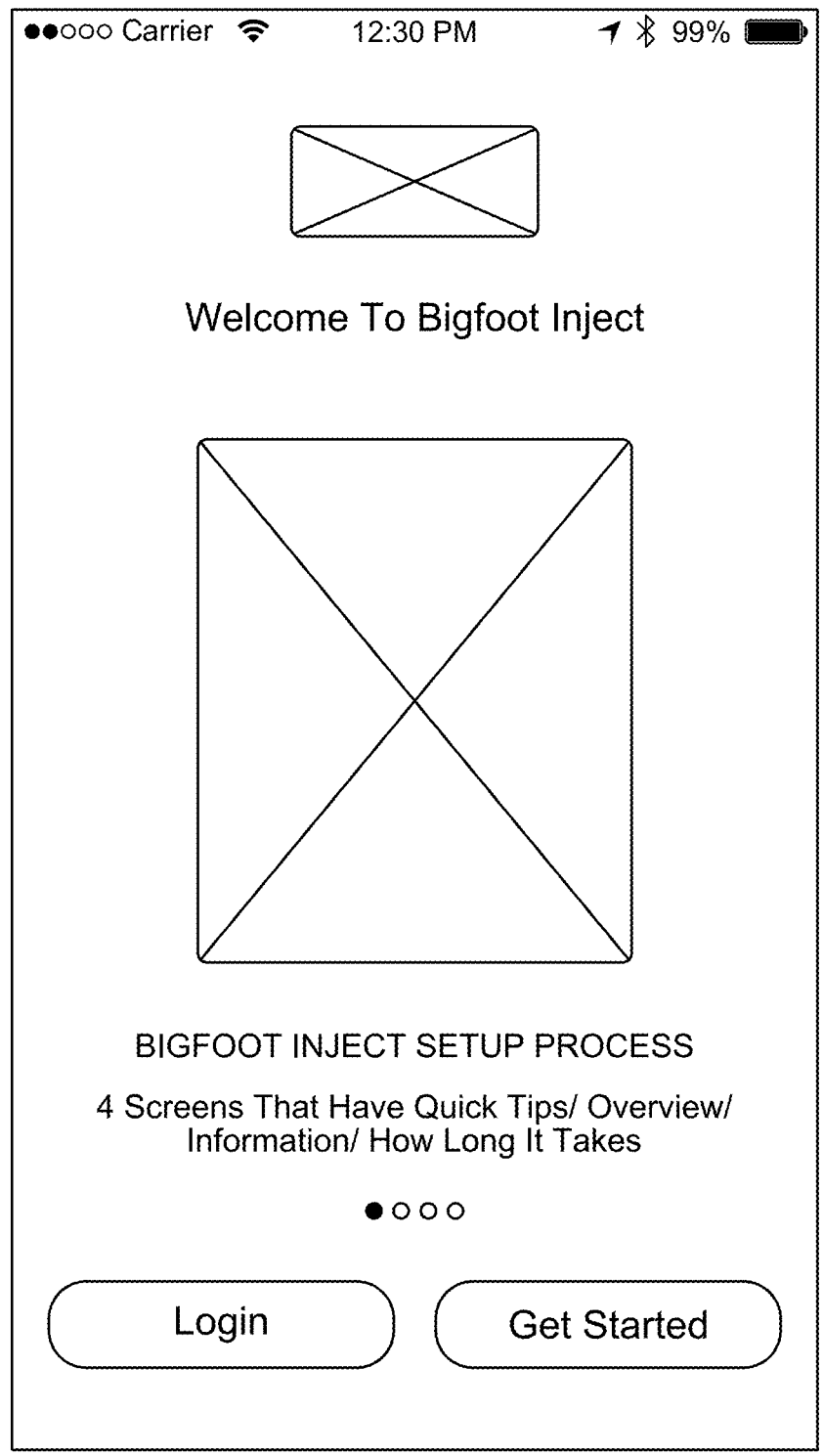

FIG. 20 shows an example welcome screen in a mobile application of a mobile device 140 for a diabetes management system, such as those depicted in FIG. 1A, 1B, or 1C. In the welcome screen, the user can click a get started button to enter their settings, which might be dictated by a healthcare professional. The user may be given the opportunity to enter information relating to their insulin therapy (e.g., the brand and/or generic name of the long-acting and/or rapid-acting insulin, average dosage information, etc.). In some embodiments, a user may be asked to select long-acting insulin brands and/or rapid-acting insulin brands from a list of known brands. In some cases, a user may also be asked about whether they use two insulin pens or one, and the product configuration may occur on the fly during setup. For example, some therapy settings may be automatically set responsive to selected insulin brands. In some embodiments, prescription information may be associated with a pen cap (for example, downloaded from a therapy management system or entered by a medical provider), and list of insulin brands may be curated based on the prescription information. Moreover, therapy settings may be automatically set responsive to the prescription information.

Figure 21:
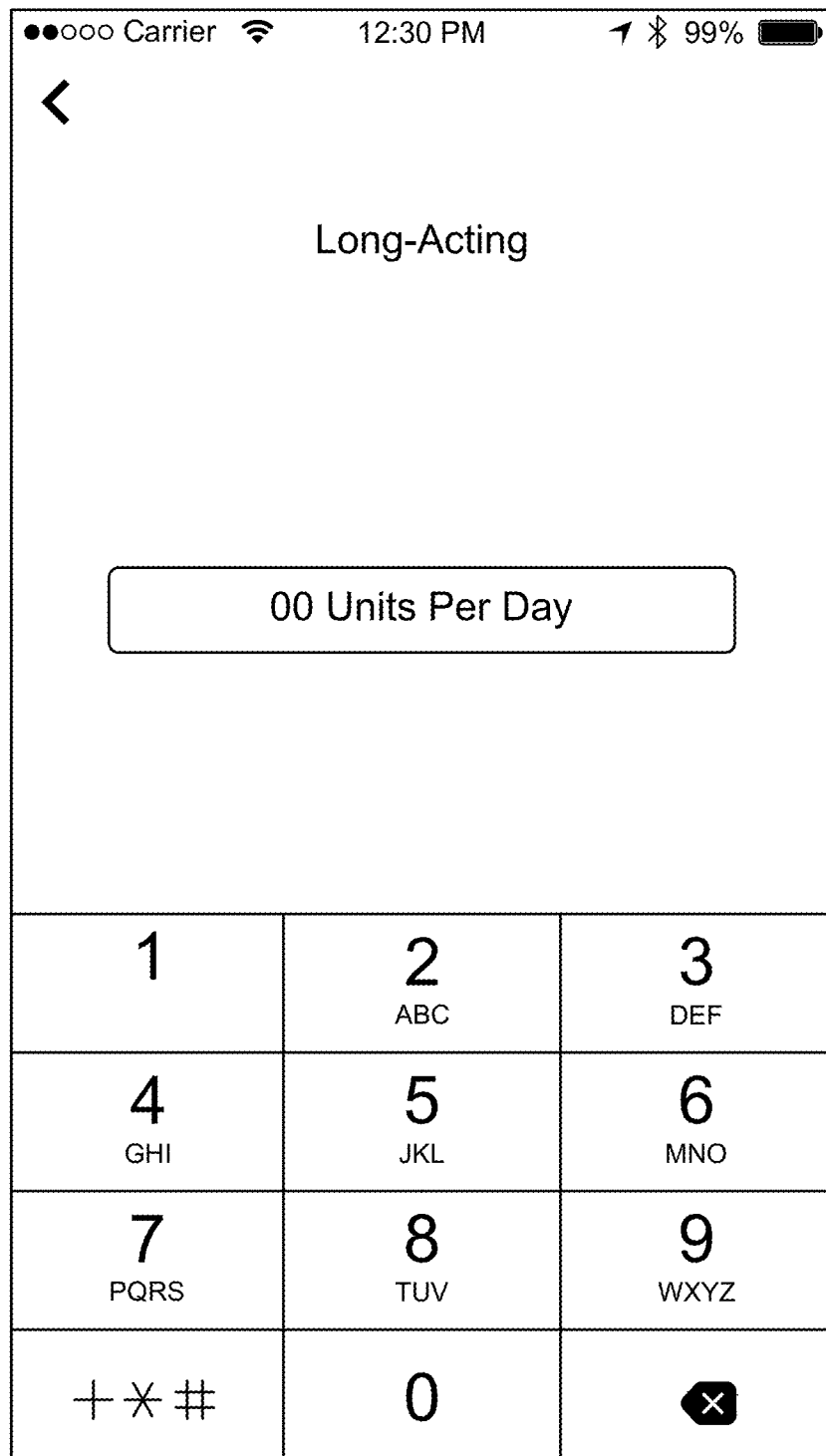
Figure 22:
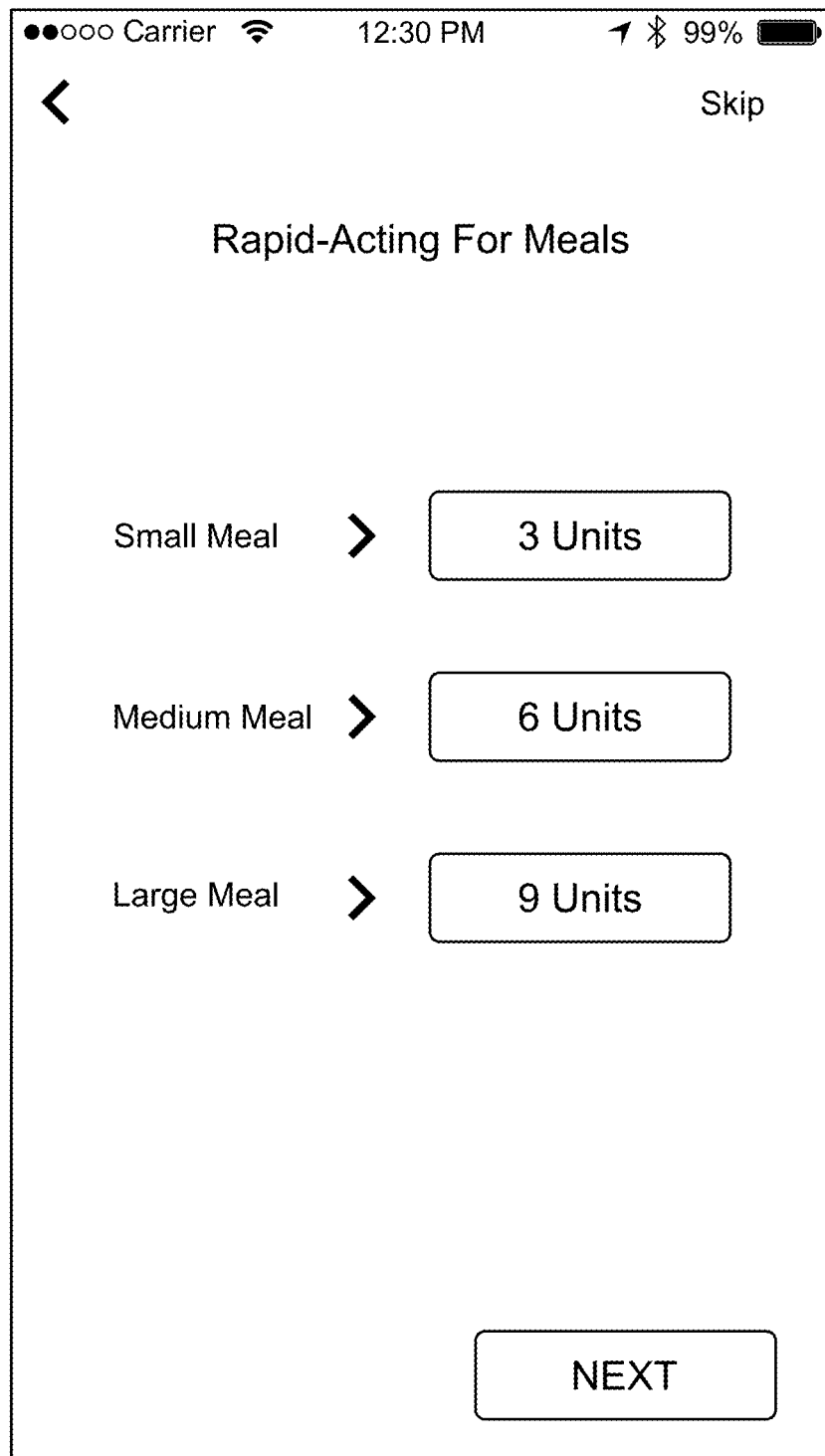
Figure 23:
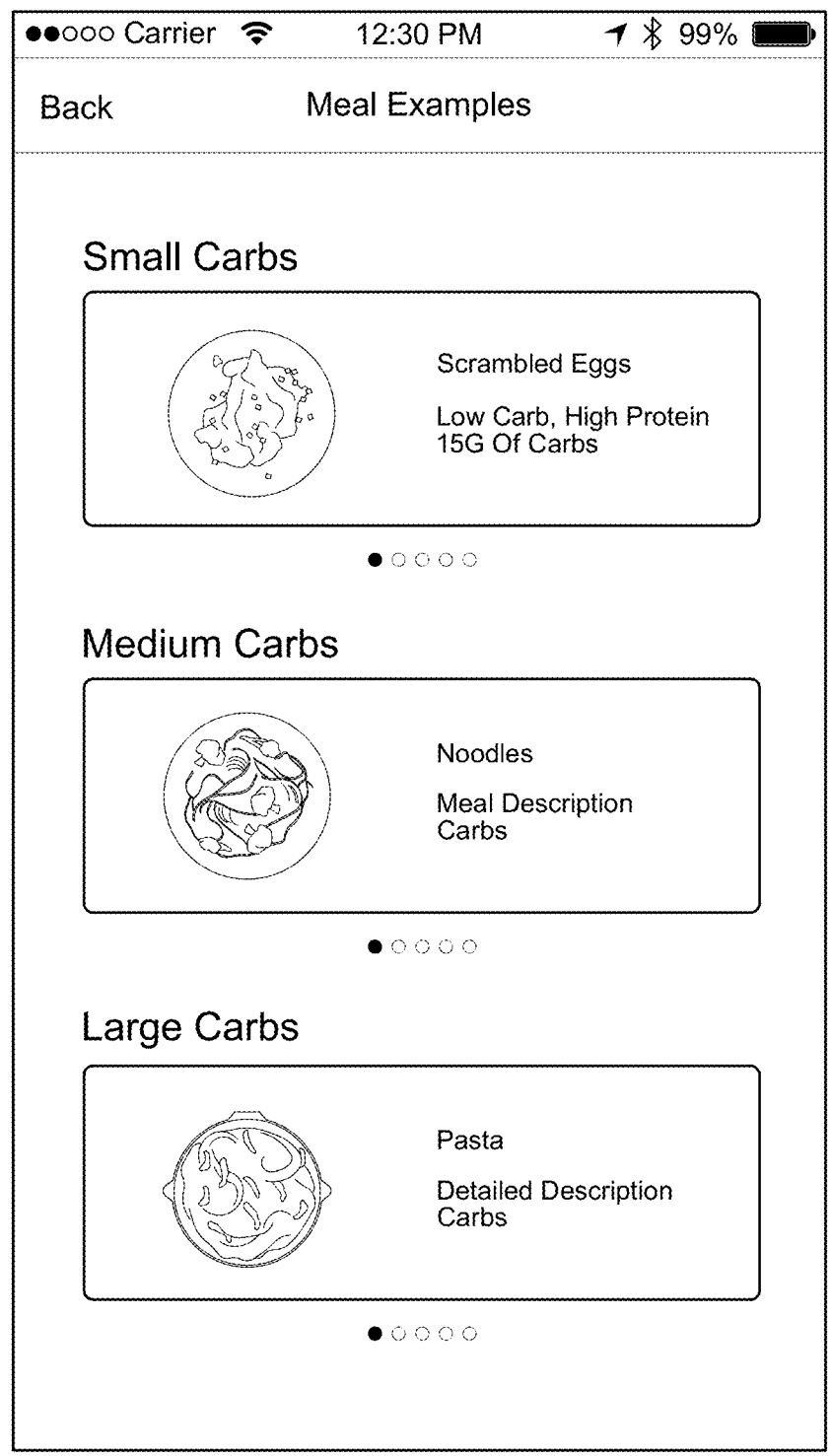

The mobile application might present the screen shown in FIG. 21 where the user is asked to enter their daily dose of long-acting insulin (e.g., in whole or half units or other resolution based on the resolution of the user's long-acting insulin pen 110). The user interface might use, for example, a sliding wheel or a number pad as shown. In some embodiments, the user might be asked to enter the time (or times) of the day when the user generally injects their long-acting insulin. In another screen, such as shown in FIG. 22, the user can enter their normal dosage amounts for differently sized meals. In some embodiments, each of these fields may be prefilled with a recommended amount based on the user's daily dosage of long-acting insulin, which may be based on population models. For example, preset amounts may be prefilled based on a relationship as discussed in U.S. patent application Ser. No. 15/717,805, but the user interface can allow the user to override these prefilled numbers by pressing in the fields to enter their own doses for each meal size. In some embodiments, the mobile application can show the user examples of meals that fit each category so that the user can compare their mental model regarding what constitutes a small meal, a medium meal, and a large meal to the assumptions of the system. FIG. 23 depicts an example user interface for depicting example meals having a portion size that fit the different categories. For example, for the "Small Carbs" meal, each meal depicted would have a similar glycemic impact (e.g., a similar carbohydrate amount). Likewise, the "Medium Carbs" meals and "Large Carbs" meals would also have similar glycemic impacts (e.g., the same amount of carbohydrates) for those depicted in each category. For example, the meals depicted for "Small Carbs" could each include about 15-20 grams of carbohydrates, the meals depicted for "Medium Carbs" could each include between 35-45 grams of carbohydrates, and the meals depicted for "Large Carbs" could each include between 60-80 grams of carbohydrates. After setting the meal doses, the user can then select a glucose goal or glucose target range.

Figure 24:
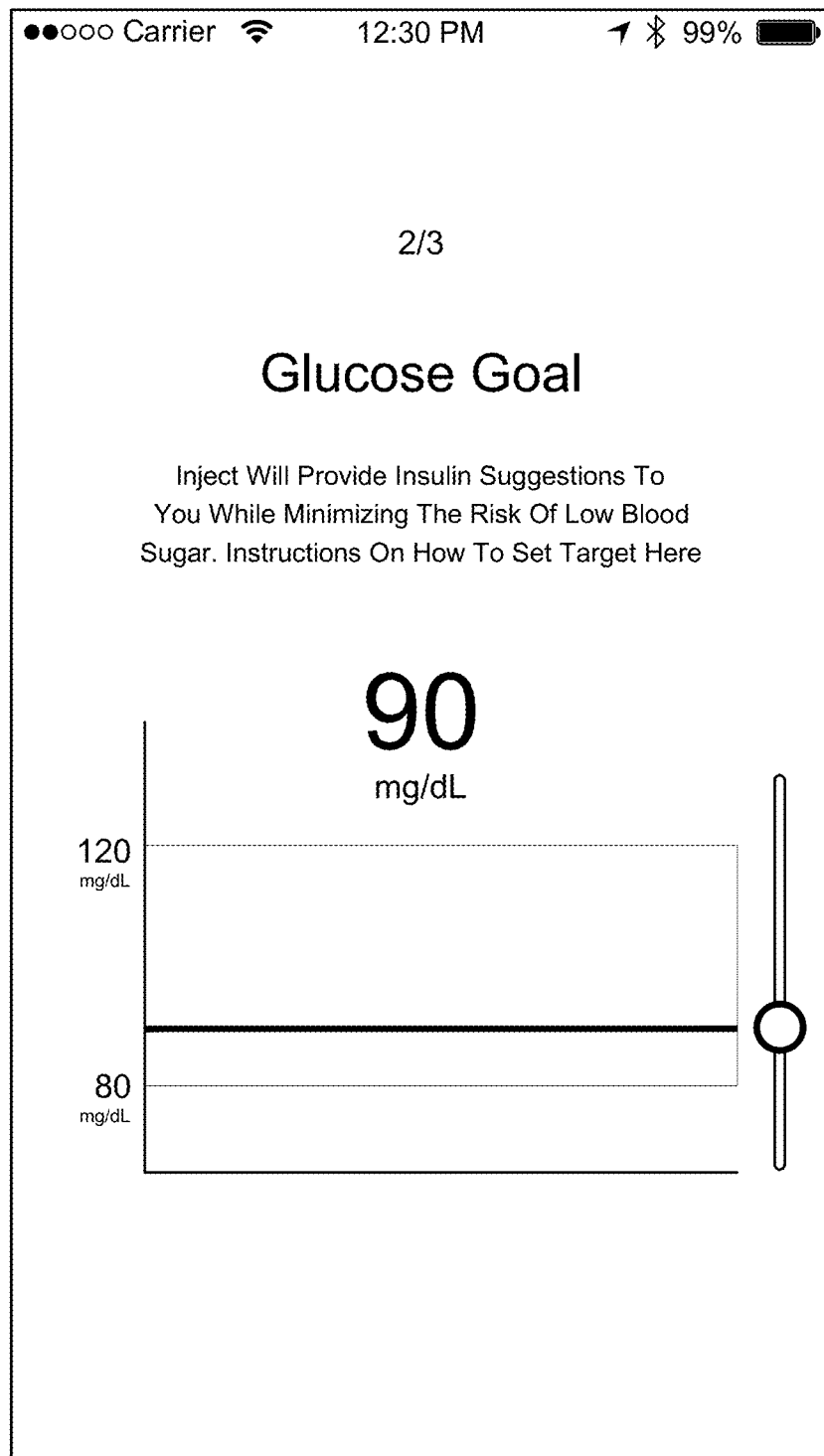

FIG. 24 depicts an example user interface where a user can upwardly or downwardly adjust a glucose goal value. In some embodiments, the glucose goal value can default to a preset number (e.g., 100 mg/dl, 80 mg/dl, 120 mg/dl, etc.).

Figure 25:
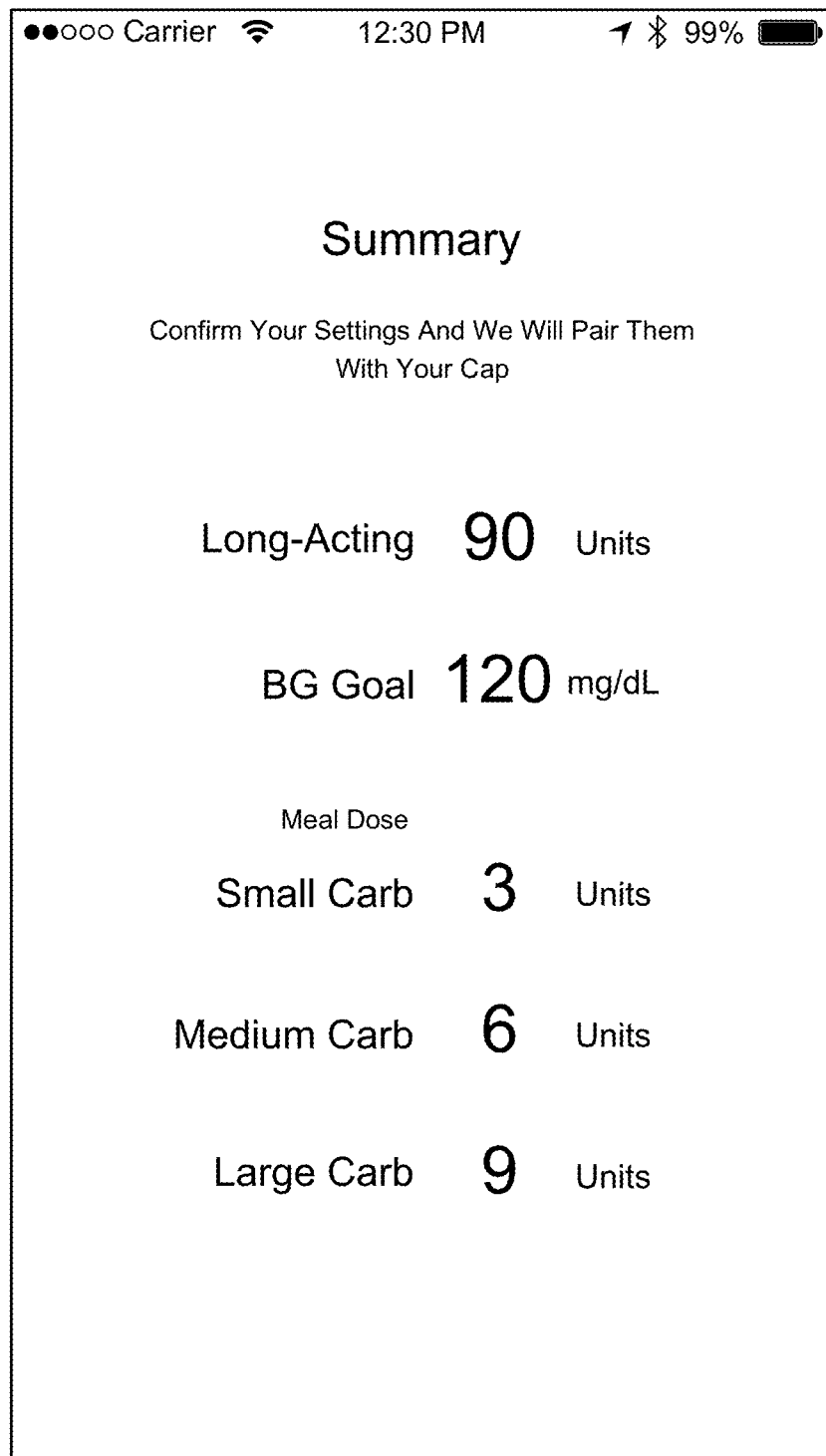

In the screen shown in FIG. 25, a user can review their settings (and, optionally, further adjust their settings).

Diabetes management systems provided herein can, in some embodiments, use data relating to the user to customize one or more correctional doses.

In some embodiments, a user interface on the mobile device 140 or available via the cloud from a remote server can permit a health care professional or a PWD to set an ISF or input other data use to determine correction doses. In some embodiments, a glucose goal value set in FIG. 24 may be used along with an ISF (or increment value) input by or at the direction of a health care professional to produce a linear sliding-scale correction chart. For example, the equation that might define the linear sliding-scale correction chart would be as follows:

Correction dose=rounddown(Current Blood Glucose−Glucose Goal)/ISF.

Figure 33:
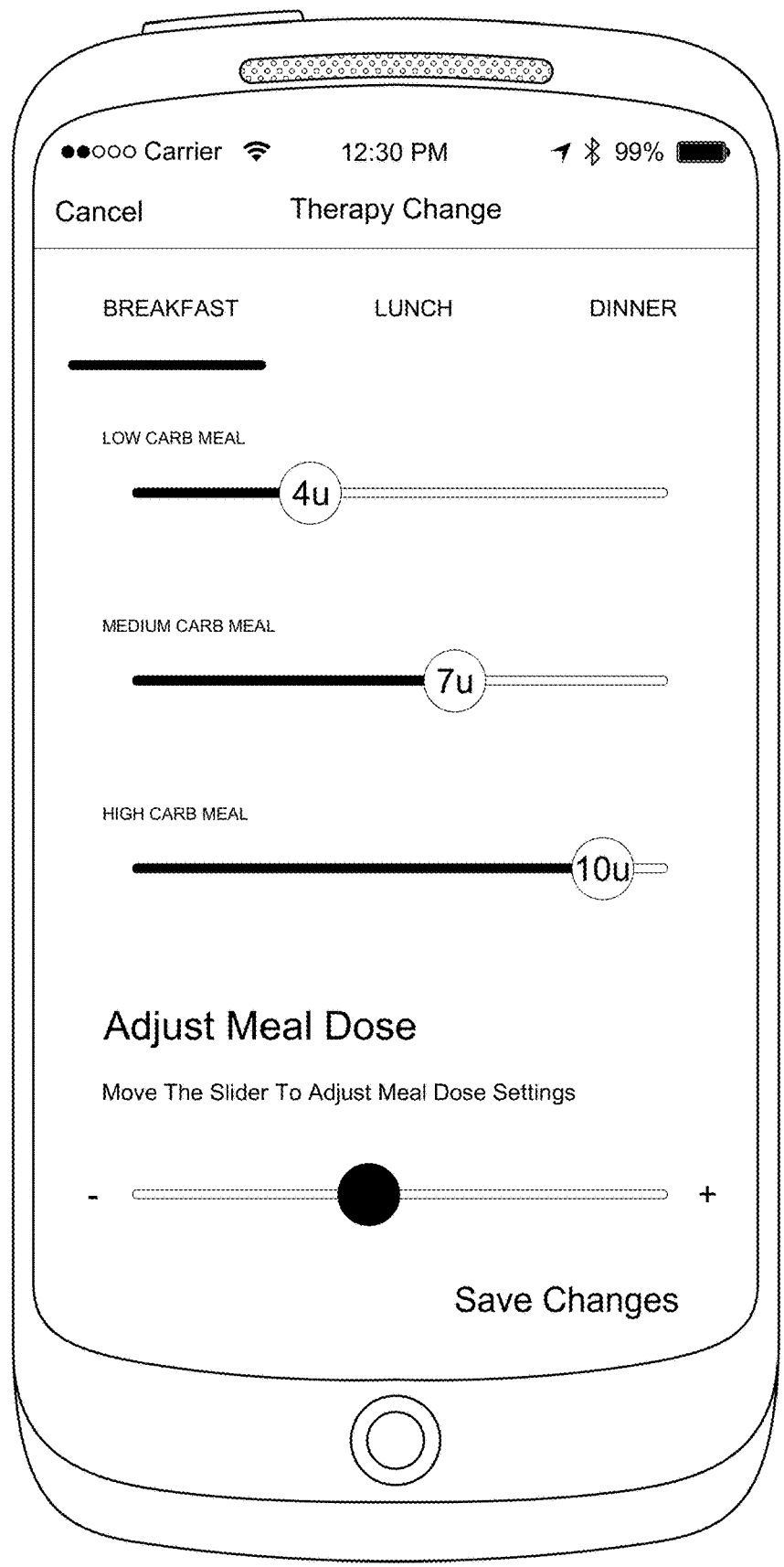

In some embodiments, the glucose goal set in FIG. 24 can define a midrange of a glucose target range and the equation can use the lower bound of the glucose target range to calculate a correction dose. In some embodiments, the ISF may be inferred from a mathematical relationship between the user's daily dosage of long-acting insulin. FIG. 26 depicts how a sliding scale chart may be determined by an ISF or interval and a glucose goal or target. In some embodiments, a user interface on the mobile application or in a web portal can generate a sliding scale chart for the PWD, caregiver, or health care professional to review before accepting the summary shown in FIG. 24. In some embodiments, a sliding scale chart may be included in the therapy summary. The sliding scale chart can simplify the user's understanding of how the system is adjusting their therapy based on real-time blood glucose readings from the glucose sensor. In some embodiments, a user interface may use a slider to enable a user to update the increment or the start and to have the generated sliding scale correction chart dynamically update in order to enable a health care professional or PWD have the generated chart match their desired therapy settings (e.g., as shown in FIG. 33).

Figure 27:
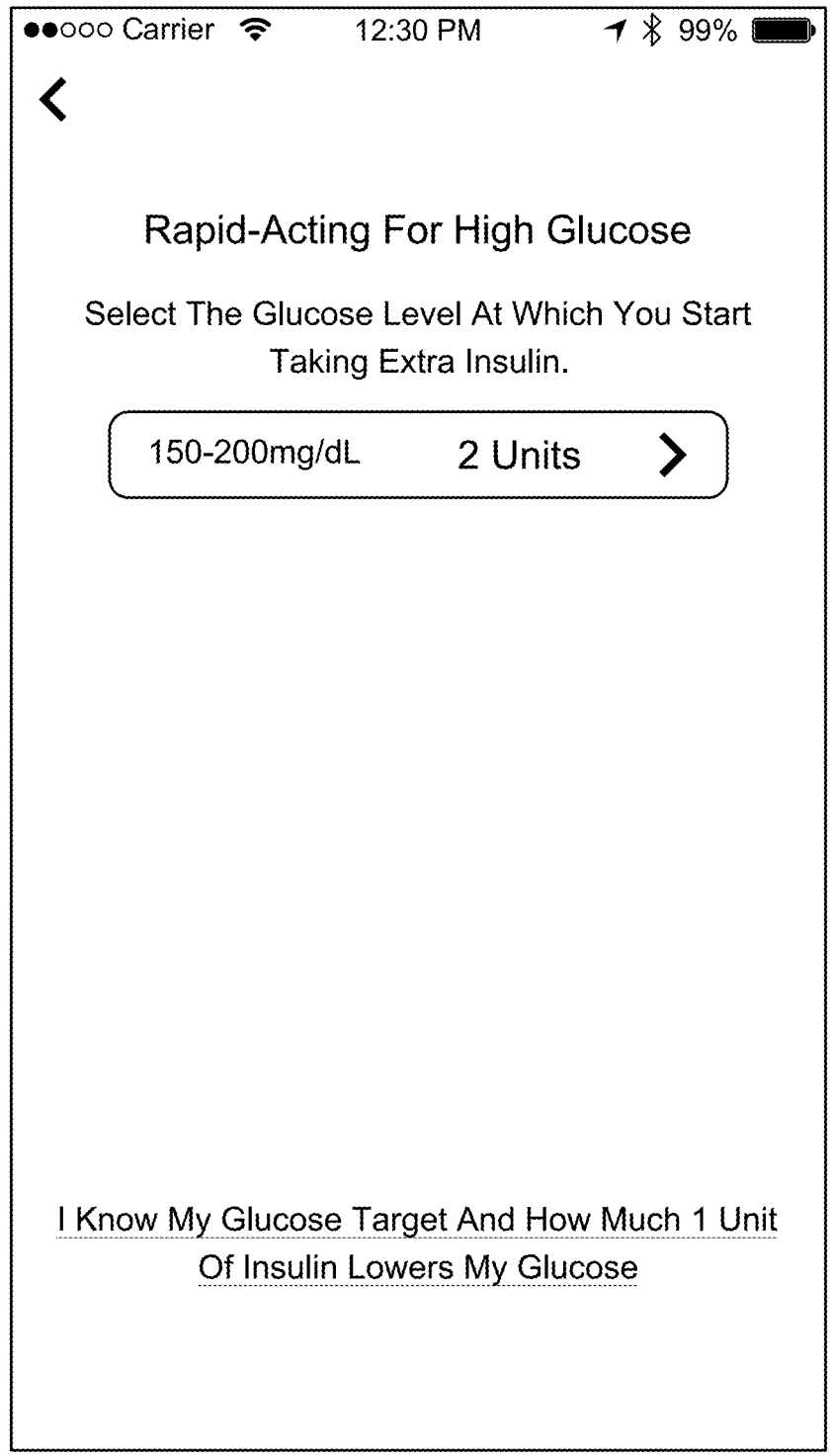
Figure 28:
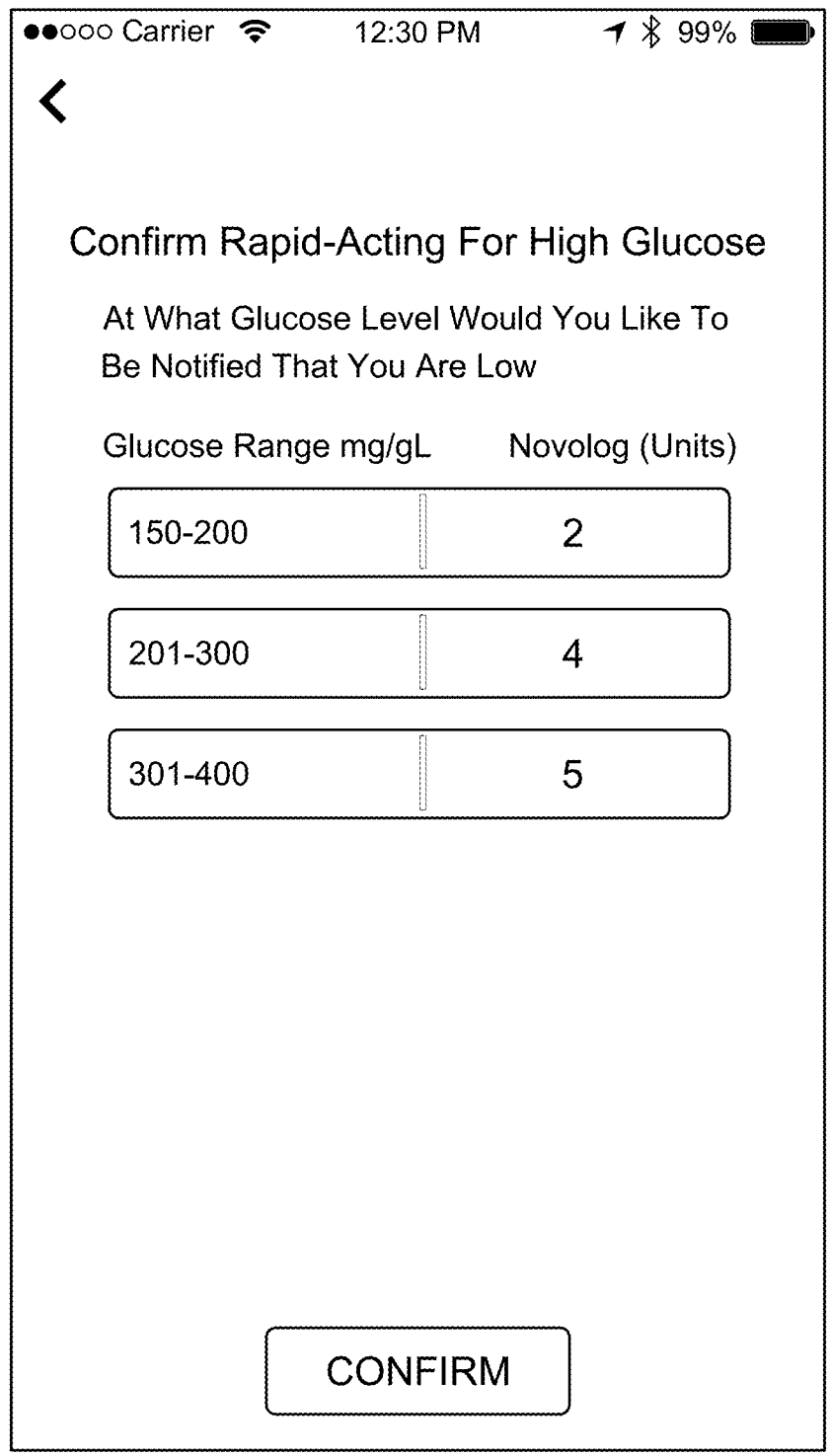

FIGS. 27 through 30 depict different options that may be presented to the user via a user interface to enable the mobile application to create a sliding scale (e.g., as shown above in FIG. 18). As shown in FIG. 27, as a first option, the mobile application may prompt the user (e.g., the subject and/or a caregiver) to enter values relating to actions (e.g., based on historical use) taken by the subject while managing blood glucose levels. For example, historical data relating to the amount (e.g., units) of insulin (e.g., rapid-acting insulin) taken in response to a certain blood glucose level range. As shown in FIG. 28, more than one range may be inputted to create a user-inputted scale, which may be (e.g., result in) a non-linear scale.

Figure 29:
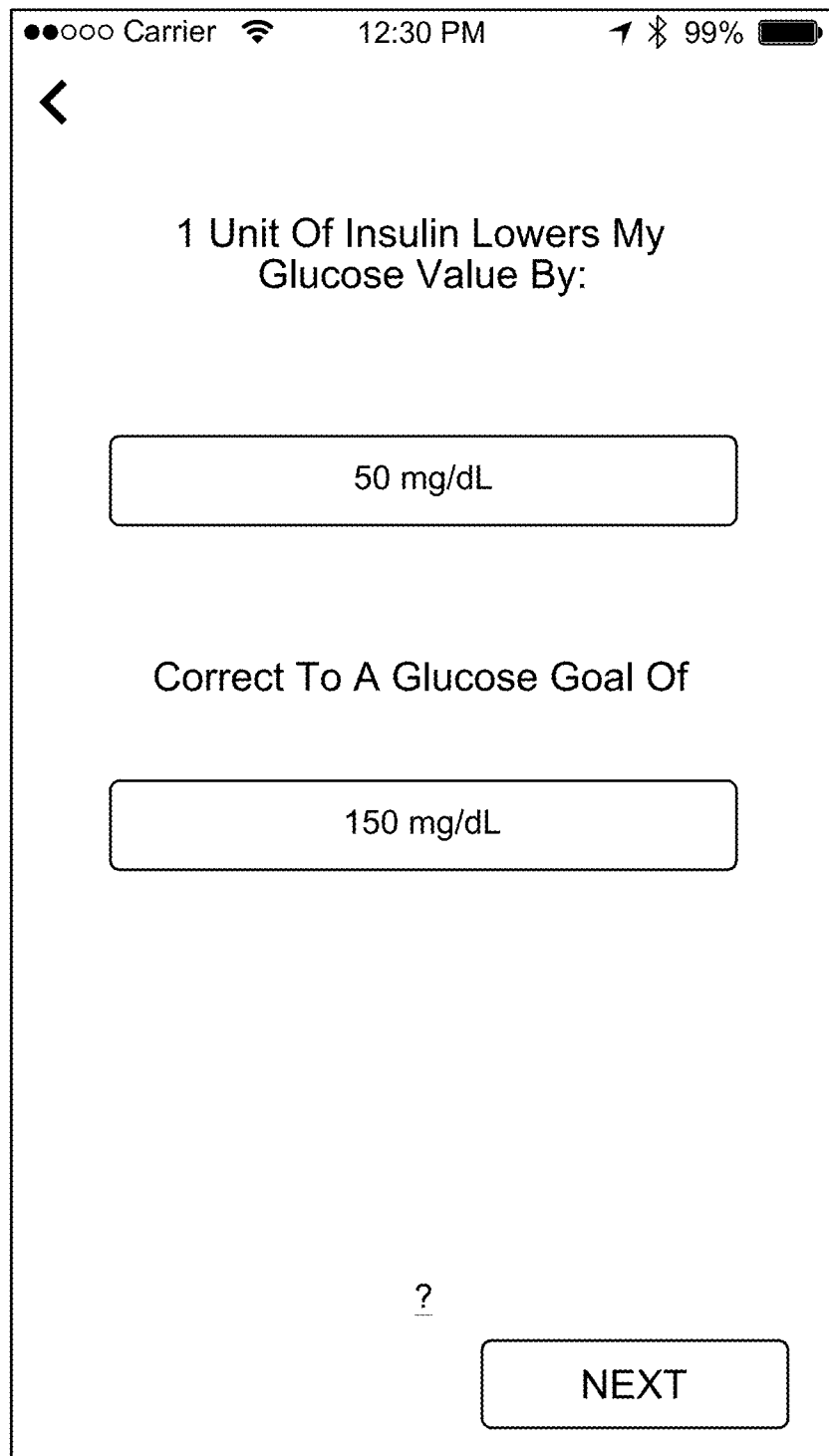
Figure 30:
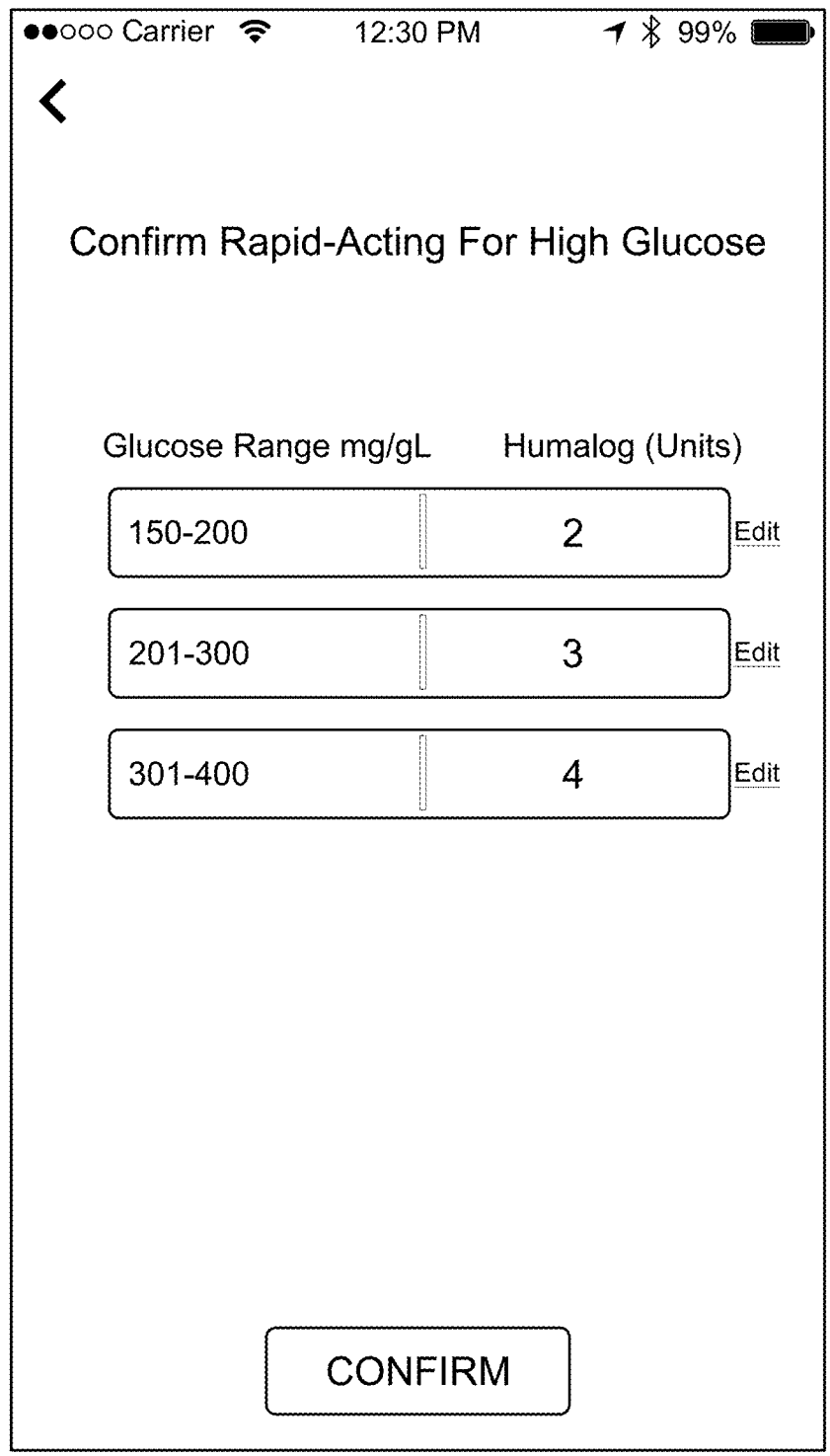

As shown in FIG. 29, as a second option, the mobile application may prompt the user to directly enter values relating to the ISF of the subject. For example, the user may enter the average drop in blood glucose level, measured in milligrams per deciliter (mg/dl), caused by each unit of insulin taken by the subject. In some embodiments, the mobile application may enable the user to enter a target blood glucose level.

In either option, the mobile application may display a confirmation of the scale (e.g., non-linear scale) entered manually by the user under the first option or a confirmation of the scale (e.g., a linear scale) generated using the ISF value entered by the user under the second option.

Figure 32:
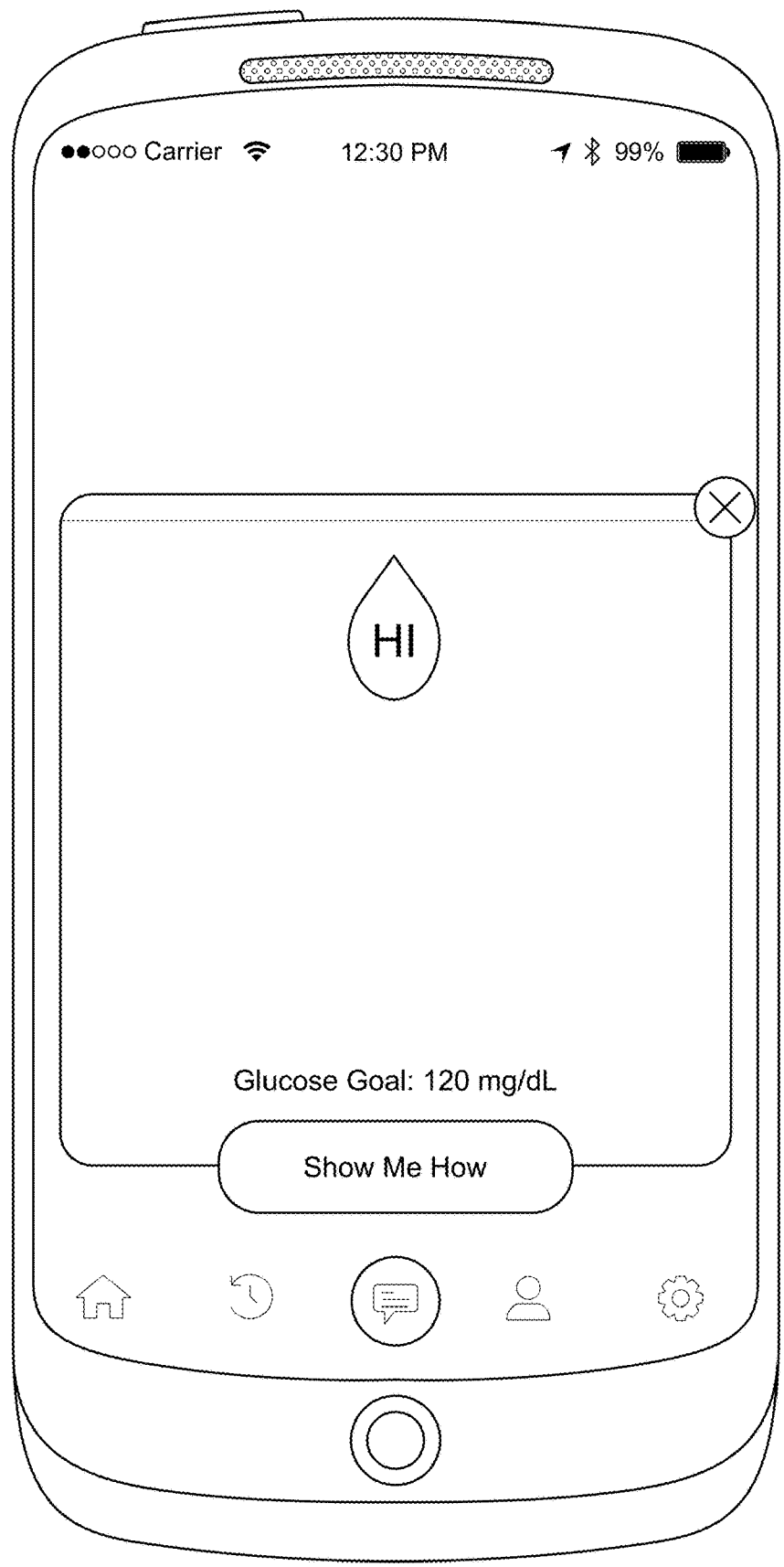

Methods, devices, and systems provided herein may detect patterns in blood glucose levels and/or patterns of injections that enable the devices or systems to understand the impact of dosing and determine recommended therapy setting changes to improve glycemic outcomes. In some embodiments, the mobile device can determine appropriate therapy changes. In some embodiments, a remote server can determine appropriate therapy settings. In some embodiments, methods, devices, and systems can incrementally automatically adjust dosages for different meal sizes as described in U.S. patent application Ser. No. 15/717,805, which is hereby incorporated by reference. In some embodiments, algorithms can update the ISF or the correction doses based on detected patterns. In some embodiments, methods, devices, and systems can determine if there is a therapeutically relevant change recommended and then use that information to tell the user about the pattern or to tell the user about the pattern with a trigger, a tip, or a suggestion to the user (e.g., a message in the mobile application); examples of which are depicted in FIG. 31. For example, messages might be as shown in FIG. 31 and/or displayed on the mobile device as shown in FIG. 32. As shown in FIG. 32 the message might include a button to bring the user to a screen that shows the user how to make an appropriate change (e.g., in-app training) and/or to a screen to actually make the change. Pressing this button might bring the user to a screen shown in FIG. 33, which includes a plurality of sliders for each meal size. In some embodiments, the user might elect to just change the size of one meal or might desire to change things across the board by changing the bottom slider. In some embodiments, changing the bottom slider might change an ISF value. In some embodiments, the settings may be based on time of day (e.g., breakfast time, lunch time, dinner time) and a user can adjust the settings particularly for one of those mealtimes or all of those mealtimes.

Alerts and Alarms

In some embodiments, diabetes management systems, devices, and methods provided herein may provide notifications, alarms, and/or alerts. In some embodiments, notifications, alarms, and/or alerts may be automatically triggered on one or more portions of the system, such as, for example, the mobile device, the pen caps, and/or one or more separate alert accessories. In some embodiments, therapy management systems, devices, and methods provided herein can include a smart pen or pen accessory (e.g., an accessory adapted to be secured to a pen, such as, for example, a pen cap and/or another accessory that is integral with or may be applied and/or coupled to the pen) that is adapted to provide notifications, therapy recommendations, and/or alerts upon the user taking action to retrieve blood glucose data. In some embodiments, therapy management systems, devices, and methods provided herein can include both one or more alert accessories and one or more smart pens or pen accessories that can each wirelessly receive blood glucose data (e.g., from a continuous glucose monitor). In some embodiments, therapy management systems, devices, and methods provided herein may have one or more smart pens or pen accessories that communicate with a blood glucose monitoring system (e.g., a continuous glucose monitor) via a first communication technique (e.g., NFC) and have one or more alert accessories that communicate with a blood glucose monitoring system (e.g., the same continuous glucose monitor) via a second communication technique (e.g., UHF, BLE). In some embodiments, the communication technique for communicating blood glucose data to the alert accessory has a larger range than the communication technique for communicating blood glucose data to the smart pens or pen accessories. In some embodiments, therapy management systems, devices, and methods provided herein can include one or more alert accessories that passively receive blood glucose data (e.g., via wireless communication), provided that it is in a communication range, and one or more smart pens or pen accessories that are configured to only wirelessly receive blood glucose data if a user takes action to have the smart pen or pen accessory receive blood glucose data (e.g., presses a button, swipes the pen or pen accessory adjacent to a glucose sensor, etc.). In some embodiments, having a smart pen or pen accessory that only receives blood glucose data upon user action can reduce the power consumption for the smart pen or pen accessory, thus reducing the burden on the user to recharge or replace batteries in the smart pen or pen accessory. In some embodiments, having an alert accessory as provided herein can enable the user to decide when and where to receive disruptive alarms, alerts, and notifications, and further permit the user to not feel a need to carry around their insulin pens between doses.

Methods, systems, and devices provided herein can include one or more alert accessories that can take any suitable form. In some embodiments, an alert accessory can include one or more illuminable icons. In some embodiments, an alert accessory can include a digital display screen. In some embodiments, an alert accessory can include one or more speakers and/or vibrational motors. In some embodiments, alert accessories contemplated herein may be secured to a smartphone (e.g., as a phone case). In some embodiments, alert accessories contemplated herein may be secured to a keychain. In some embodiments, alert accessories contemplated herein may be adapted to serve as a bedside alarm clock. In some embodiments, alert accessories are contemplated herein.

In some embodiments, methods, systems, and devices provided herein may provide guidance regarding an appropriate dosage of insulin. In some embodiments, the dosage of insulin may be administered with an insulin delivery pen or syringe. In some embodiments, the insulin may be long-acting insulin. In some embodiments, the insulin may be rapid-acting insulin. In some embodiments, an insulin delivery pen, or accessory therefor (e.g., a cap), can detect an amount of insulin delivered from the pen (or an amount of insulin that was set for delivery). In some embodiments, an insulin pen, or an accessory therefor, can include a user-interface, which can display data or recommendations to the user and/or permit the user to enter data into the insulin pen or accessory.

The following example therapy management system includes insulin delivery pens having dose-capture pen caps, but other embodiments are envisioned where the functionality disclosed herein is incorporated into other accessories for an insulin delivery pen or the insulin delivery pen itself. Additionally, the following example therapy management system includes a single alert accessory (e.g., a CGM fob), but other embodiments are envisioned that include multiple alert accessories or where the functionality of the alert accessory is merged into a smartphone or other web-connected mobile computing device (e.g., using WiFi or cellular communications).

In some embodiments, one or more portions of the system (e.g., the pens, the mobile application, the alert accessory) may be configured to present one or more of the following alarms or alerts:

Glucose Alerts: low glucose, high glucose, high likelihood of low glucose in the future, high likelihood of high glucose in the future, high glycemic variability Timing Alerts: alerts to check blood glucose (e.g., for a specific diurnal time segment), alerts for meal timing, pen uncapped for a certain duration, double doses (e.g., pen uncapped twice in a short time period)

Rapid-acting Insulin Alerts: take correction dose, missed rapid-acting dose, dangerous rapid-acting dose, dose exceeding threshold Long-acting Insulin Alerts: take long-acting dose, missed long-acting dose, dangerous long-acting dose, dose exceeding threshold Switched Insulin Alerts: dangerous dose taken—switched doses, wrong pen cap Temperature Alerts: out of range conditions of the insulin detected, as discussed above Maintenance Alerts: out of insulin, low power, sensor failure, sensor expired In some cases, methods and systems provided herein include an alarm or alert that is triggered if a user removes a long-acting pen cap or rapid-acting pen cap during a time period when a user should not (or should administer a different dose) administer long-acting insulin or rapid-acting insulin. For example, when an uncapping of a long-acting pen cap is detected, then insulin dose information about a recent dose of long-acting insulin may be reviewed. Reviewed dose information may include dose amount, dose time, type of insulin, and/or brand of insulin. Based on dose information and uncapping information, a risk of a user mistake may be inferred. Examples of user mistakes for which a risk may be inferred include, but are not limited to, administering a dose of long-acting insulin instead of rapid-acting insulin and administering a dose of long-acting insulin and/or rapid-acting insulin too soon after a previous dose. So, a contemplated operation of methods and systems of this disclosure includes, for example, an uncapping event is detected for a long-acting pen cap at 9:30 AM. Dosing events corresponding to inferred dosing actions (e.g., based on capping events as described herein) are reviewed and a dosing event for long-acting insulin at 8:00 AM is identified. Dosing information indicates that a dose of long-acting insulin was administered at 8:00 AM, the amount of insulin administered corresponds to a basal dose, and a risk of a user mistakenly administering a second dose of long-acting insulin is inferred (such a risk may also be characterized as a risk of insulin stacking). In some cases, the earlier dose may be confirmed based on blood glucose data, changes in which would be indicative of insulin action on a user's blood glucose levels. Upon inferring the risk of a user mistakenly administering long-acting insulin, an alarm or alert may be generated and presented to a user. For example, a pen cap, injection pen, or mobile device may vibrate or emit an audible sound indicating to a user that there may be an error.

Upgradable System

Diabetes management systems provided herein may be adapted to add or remove components from use and/or to be configured based on the needs of the person with diabetes (PWD). For example, FIGS. 34A-34D illustrate different systems and the associated communication architecture that permit use for PWDs having different types of diabetes (Type 1 or Type 2, as shown, or additionally including gestational diabetes or other types of diabetes), different progressions of diabetes, and/or different preferences for how to monitor and/or treat their diabetes. In some cases, methods and devices provided herein may be adapted to determine when additional therapies are warranted and recommend the addition of additional therapies or devices to the therapy and/or the system.

Figure 34A:
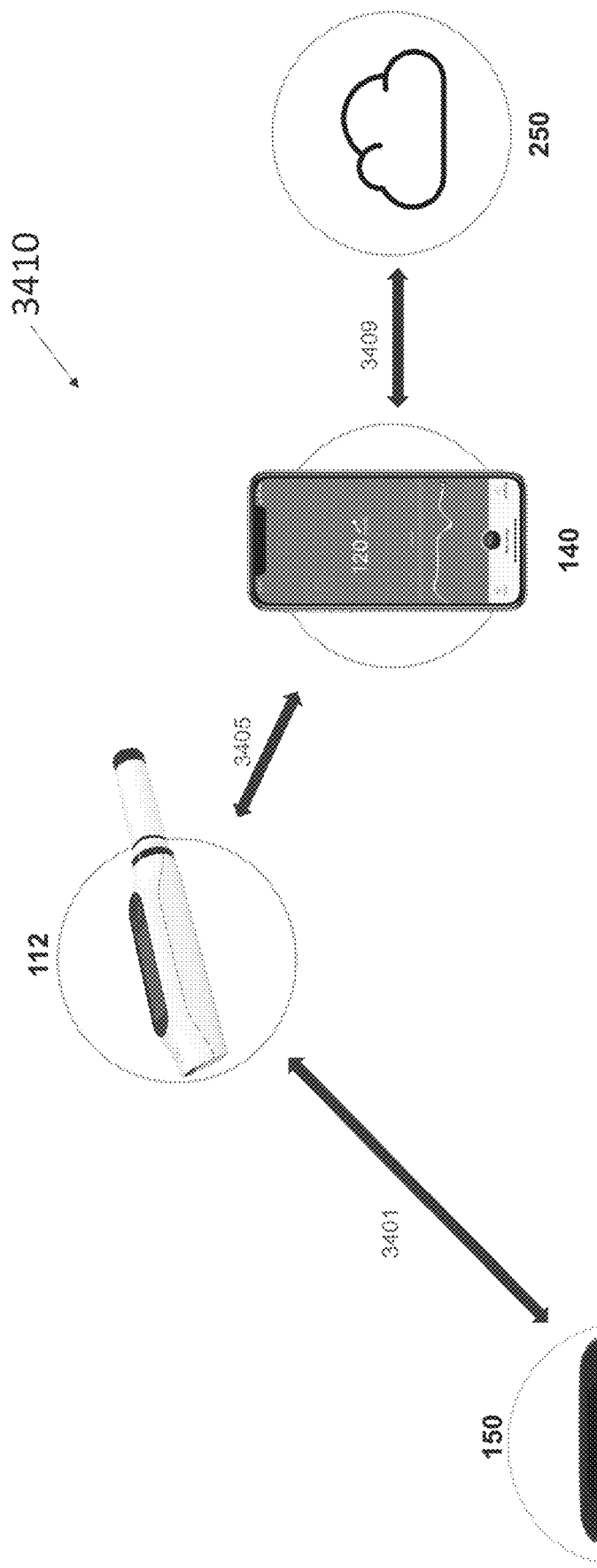
FIGS. 34A-34D illustrate example communications architectures for an upgradable system according to embodiments of the present disclosure.

FIG. 34A depicts a system 3410 that includes only a BGM 150, a mobile device 140 having a mobile app, a long-acting insulin injection pen 110, and a long-acting pen cap 112. System 3410 can communicate with cloud or web services 250 via mobile device 140 as discussed above. System 3410 may be adapted for use by PWDs that do not require mealtime insulin (e.g., early progression of type 2 diabetes and/or gestational diabetes) or PWDs that do not want rapid-acting insulin doses to be tracked. BGM 150 is a blood glucose meter adapted to determine estimated glucose values (EGVs) through the use of test strips that analyze in-vitro blood samples. As shown, BGM 150 can transmit single-point EGVs to pen cap 112 via BLE communications link 3401. The EGVs from BGM 150 can then be transmitted from pen cap 112 to mobile device 140 via BLE communications link 3405, and via mobile device 140 to cloud or web services 250 for analysis via network communications link 3409. BLE communications link 3405 can also transmit pen capping data to mobile device 140, which can also be transmitted via link 3409 to web services 250. Mobile device 140 can display the most recent EGVs and/or a graph of collected EGVs. Recommended doses of long-acting insulin may be displayed on pen cap 112 in a manner similar to that shown in FIG. 6 and in FIG. 35A. System 3410 can prompt a use to collect fasting EGVs with BGM 150. System 3410 can use fasting EGVs to recommend changes or automatically make changes to the displayed recommended doses of long-acting insulin using standard long-acting insulin titration techniques or any other suitable algorithm. In some cases, algorithms may be used in system 3410 to determine if a PWD should add rapid-acting insulin to their therapy.

Figure 34B:
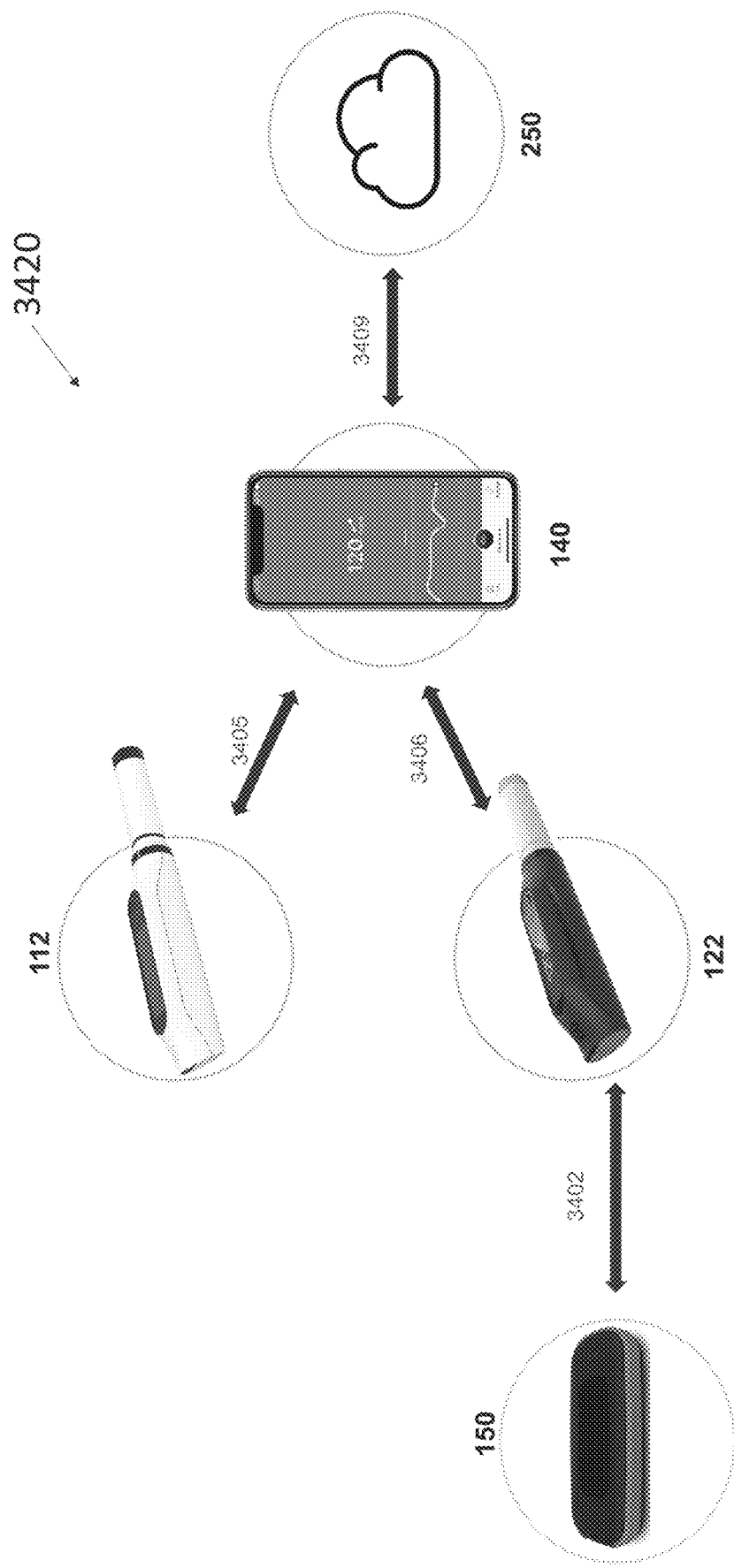
Figure 35B:
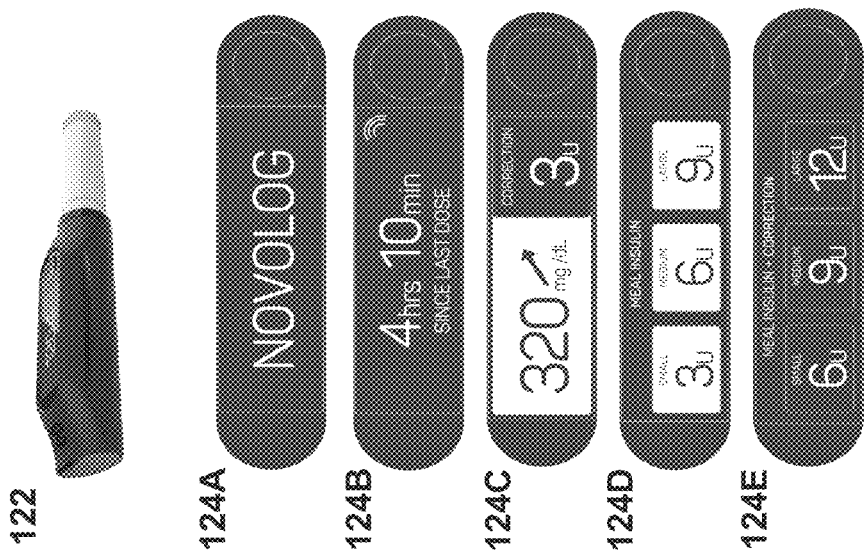
FIGS. 35A and 35B illustrate exemplary displays on pen caps according to embodiments of the present disclosure.

FIG. 34B depicts a system 3420 that includes the components of system 3410 but adds a rapid-acting insulin pen 120, and a rapid-acting pen cap 122. System 3420 may be adapted for use by PWDs that require both long- and rapid-acting insulin but that wish to monitor EGVs with a BGM instead of a continuous or flash glucose monitor. When the rapid-acting pen cap is added to the system, communication link 3401 is eliminated and long-acting pen cap 112 does not receive EGVs from BGM 150 as BGM values are not used in real time to determine an instant dose of long-acting insulin, but may be used to determine a correction dose of rapid-acting insulin. As shown, BGM 150 can transmit single-point EGVs to pen cap 122 via BLE communications link 3402. The EGVs from BGM 150 can then be transmitted from pen cap 122 to mobile device 140 via BLE communications link 3406, and via mobile device 140 to cloud or web services 250 for analysis via network communications link 3409. BLE communications links 3405 and 3406 can also transmit pen capping data to mobile device 140, which can also be transmitted via link 3409 to web services 250. Mobile device 140 can display the most recent EGVs and/or a graph of collected EGVs. Recommended doses of rapid- and long-acting insulin may be displayed on pen cap 112 in a manner similar to that shown in FIGS. 3-6 and in FIGS. 35A and 35B. System 3420 can prompt a use to collect fasting and/or post-prandial EGVs with BGM 150. For example, system 3420 can in some cases trigger reminders to a user to check an EGV at a predetermined time after a pen capping event to collect post-prandial EGVs. System 3420 can use fasting EGVs to recommend changes or automatically make changes to the displayed recommended doses of long-acting insulin using standard long-acting insulin titration techniques or any other suitable algorithm. System 3420 can use post-prandial EGVs to recommend changes or automatically make changes to the displayed recommended doses of rapid-acting insulin using standard insulin titration techniques or any other suitable algorithm. In some cases, algorithms may be used in system 3420 to determine if a PWD should add a continuous glucose monitor to help the PWD achieve better glycemic control.

Figure 34C:
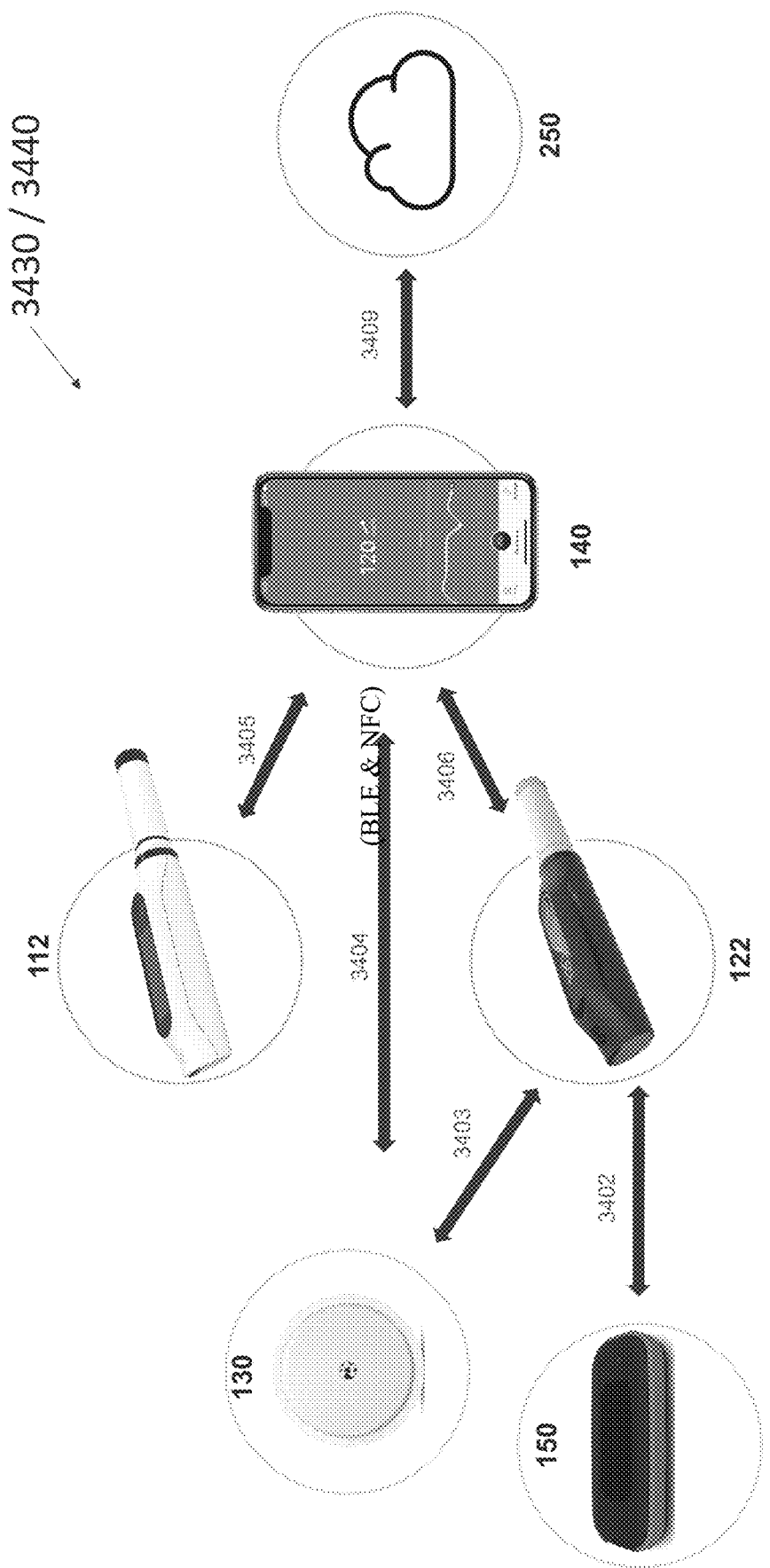

FIG. 34C depicts a system 3430 that includes the components of system 3420 but adds a continuous glucose monitor 130. CGM 130 can enable both broadcast data via BLE or UHF radio and user-initiated data transfers via NFC communications, according to one or both methods of communication may be used to transmit EGVs from CGM 130 to pen cap 122 and/or mobile device 140. No direct communication between CGM 130 and pen cap 112 is required because long-acting doses of insulin do not use a correction component. For example, NFC communication link 3403 can allow for pen cap 122 to receive EGVs from CGM 130 upon a user's decision to retrieve EGVs, such as by using a method depicted in FIG. 2 and discussed above. BLE communication link 3402 still permit the transfer of EGVs from BGM 150 to pen cap 122. The EGVs from BGM 150 and/or CGM 130 can then be transmitted from pen cap 122 to mobile device 140 via BLE communications link 3406, and via mobile device 140 to cloud or web services 250 for analysis via network communications link 3409. Additionally, EGVs from CGM 130 may be received by the mobile device 140 via communication link 3404, which can include both BLE and NFC communications. Broadcast BLE EGVs may be used to trigger EGV-based alarms or alerts announced from the mobile device 140. Missed EGVs may be filled in by scanning the CGM 130 the mobile device 140 or pen cap 122 to get multiple hours of prior EGV data (e.g., 4 hours, 6 hours, 8 hours, or 10 hours). BLE communications links 3405 and 3406 can also transmit pen capping data to mobile device 140, which can also be transmitted via link 3409 to web services 250. Recommended doses of rapid- and long-acting insulin may be displayed on pen cap 112 in a manner similar to that shown in FIGS. 3-6 and in FIGS. 35A and 35B. System 3430 can use EGV data in combination with dose data (e.g., timing data) to recommend changes or automatically make change to the displayed recommended doses of rapid-acting insulin using standard insulin titration techniques or any other suitable algorithms.

FIG. 34C also indicates that a system 3440 can also include the same components. System 3440 differs from system 3430 in that it includes pen caps 112 and 122 adapted to detect amounts of insulin remaining in insulin pens 110 and 120, which may be used to determine dose amounts of insulin. Other methods may be used to detect doses, either in caps or other accessories or as part of a smart pen or smart inhaler, and are thus contemplated herein. Additionally, system 3440 may use captured dose data to more aggressively automate changes to user-specific dosage parameters.

Figure 34D:
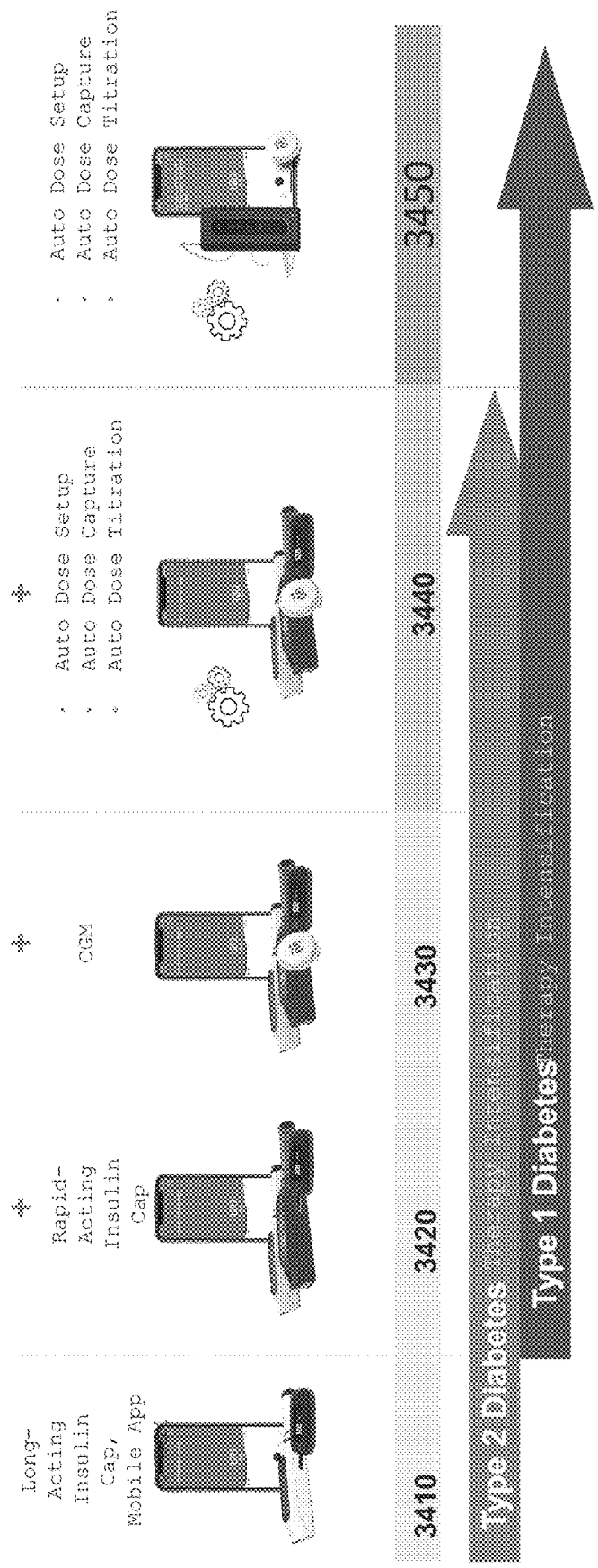

FIG. 34D illustrates the continuum of care and how components may be added to each system 3410-3440 to upgrade the system. Additionally, system 3450 is an automated insulin delivery system using an insulin pump. In some cases, the use of system 3440 or 3430 may detect candidates for switching to pump therapy, such as system 3450. In some cases, system 3450 can include pen caps 112 and/or 122, which can allow a user to selectively move between an injection therapy (e.g., MDI therapy) and a pump therapy (e.g., infusion pump therapy).

Figure 35A:
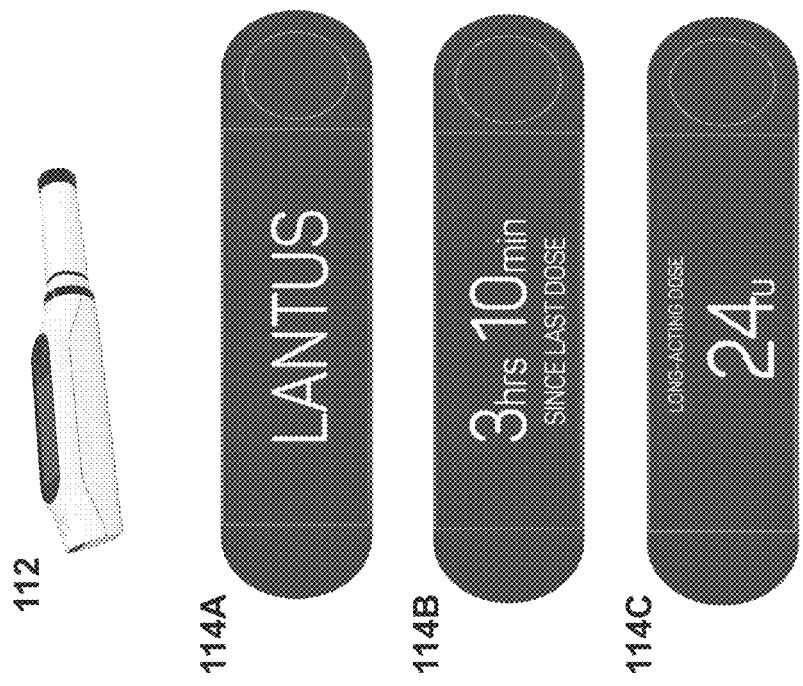

FIG. 35A illustrates example displays 114A-114C for pen cap 112. FIG. 25B illustrates example displays 124A-124E for pen cap 122. For pen cap 112, display 114A may be the standard display when the pen cap is not in use. As discussed above, the display 114 may be a bistable display that can retain an image without excessive power supply. Display 114A can include a label of the type of insulin so that a user glancing at the pen cap 112 will immediately know the type of insulin. When a button is pressed or the pen cap 112 removed a time of a last dose may be displayed in display 114B. In some cases, if the time since the last dose is less than a threshold (e.g., less than 12 hours), a warning may appear and/or the pen cap may refuse to provide a recommended dose. In display screen 114C, a recommended dose amount is shown.

For pen cap 122, display 124A may be the standard display when the pen cap is not in use. As discussed above, the display 124 may be a bistable display that can retain an image without excessive power supply. Display 124A can include a label of the type of insulin so that a user glancing at the pen cap 122 will immediately know the type of insulin. When a button is pressed or the pen cap 122 removed a time of a last dose may be displayed in display 124B. A retrieval of an EGV (e.g., via a scan of CGM 130) can cause display 124C to appear. As shown, display 124C includes a correction dose, which may be based on the EGV (and optionally trend data) using any suitable technique. In some cases, the correction dose may only appear if a time since the prior dose is greater than a predetermined number of hours and the pen cap 122 is still on the pen 120. In some cases, if the time since the last dose is less than a threshold (e.g., less than 1 hour, less than 30 minutes), a warning may appear and/or the pen cap may refuse to provide a recommended dose. In display screen 124D, meal dose recommendations are shown. In display screen 124E, meal+correction doses are shown. In some cases, display 124 can progress through display screens 124C-124E with successive button pushes.

The embodiments described herein may include the use of a special-purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general-purpose or special-purpose computer. "Special-purpose computer" is intended to be interpreted broadly and encompasses embedded systems, microcontrollers, application-specific integrated circuits, digital signal processors, and general-purpose computers programmed for specific purposes. "Segments" (e.g., code segment or data segment) may refer to a portion (e.g., address) of memory, virtual memory, or an object file.

By way of example, and not limitation, such computer-readable media may include non-transitory computer-readable storage media including Random-Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid-state memory devices), or any other storage medium that may be used to carry or store desired program code in the form of computer-executable instructions or data structures and that may be accessed by a general-purpose or special-purpose computer. Combinations of the above may be included within the scope of computer-readable media.

Computer-executable instructions comprise, for example, instructions and data that cause a general-purpose computer, special-purpose computer, or special-purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Any ranges expressed herein (including in the claims) are considered to be given their broadest possible interpretation. For example, unless explicitly mentioned otherwise, ranges are to include their endpoints (e.g., a range of "between X and Y" would include X and Y). Additionally, ranges described using the terms "approximately" or "about" are to be understood to be given their broadest meaning consistent with the understanding of those skilled in the art. Additionally, the terms "approximately" or "substantially" include anything within 10%, or 5%, or within manufacturing or typical tolerances.

The features of the various embodiments described herein are not mutually exclusive and can exist in various combinations and permutations, even if such combinations or permutations are not expressly described herein, without departing from the scope of the disclosure. In fact, variations, modifications, and other implementations of what is described herein will occur to one of ordinary skill in the art without departing from the scope of the disclosure. As such, the invention is not to be defined only by the preceding illustrative description, but only by the claims that follow, and legal equivalents thereof.

Additional non-limiting embodiments of the disclosure relate, generally to a pen cap for insulin injection pens and associated methods and systems:

Embodiment 1: A pen cap for a manual insulin delivery device, comprising: a wireless communication interface configured to receive blood glucose data from a glucose sensor system; at least one detection circuit configured to detect one or more cappings and one or more decappings of the pen cap from the manual insulin delivery device; at least one user interface configured to present one or more of therapy relevant information, therapy recommendations, and timing information associated with detected cappings or detected decappings of the pen cap; and a processor and a memory, the memory comprising: a data segment configured to store one or more of at least one user-specific dosage parameter and a recommended dose; and a code segment configured to store instructions that, while executed by the processor, are adapted to enable the processor to determine content presentable by the at least one user interface responsive to the timing information associated with detected cappings or detected decappings of the pen cap.

Embodiment 2: The pen cap of Embodiment 1, wherein the user interface is configured to present a recommended correction dose of insulin responsive to a determination that the replacement cap has been capped on the manual insulin delivery device for at least a threshold period of time, wherein the recommendation correction dose of insulin is based on an insulin sensitivity factor and target glucose value stored at the data segment of the memory.

Embodiment 3: The pen cap of any one of the preceding Embodiments, wherein the wireless communication interface is configured to communicate with the glucose sensor system via a near-field communication protocol when in proximity to at least one part of the glucose sensor system.

Embodiment 4: The pen cap of any one of the preceding Embodiments, wherein the wireless communication interface is configured to transmit messages that are associated with an insulin therapy.

Embodiment 5: The pen cap of any one of the preceding Embodiments, wherein the messages comprise indicators, and the indicators are associated with the insulin therapy.

Embodiment 6: The pen cap of any one of the preceding Embodiments, wherein the messages are configured to be received by one or more insulin therapy applications executing at one or more mobile computing devices.

Embodiment 7: The pen cap of any one of the preceding Embodiments, wherein the wireless communication interface is configured to transmit messages by broadcasting advertising messages.

Embodiment 8: The pen cap of any one of the preceding Embodiments, wherein the wireless communication interface is configured to transmit messages using data transmission.

Embodiment 9: The pen cap of any one of the preceding Embodiments, wherein wireless communication interface is configured to automatically transmit data ton insulin therapy application executing on a mobile device.

Embodiment 10: The pen cap of any one of the preceding Embodiments, wherein the wireless communication interface is configured to automatically communicate with the mobile application.

Embodiment 11: The pen cap of any one of the preceding Embodiments, wherein the wireless communication interface is adapted to communicate with the glucose sensor system using a first wireless communication technique having a first communication range and the wireless communication interface is adapted to communicate with the mobile computing device using a second wireless communication technique having a second communication range, the second communication range being greater than the first communication range.

Embodiment 12: The pen cap of any one of the preceding Embodiments, wherein the glucose sensor system comprises a flash glucose monitor.

Embodiment 13: The pen cap of any one of the preceding Embodiments, wherein the content includes a representation of a percentage of active insulin remaining within a user based on a time of a previous capping or decapping of the replacement pen cap and a current time.

Embodiment 14: The pen cap of any one of the preceding Embodiments, wherein the code segment is configured to store instructions that, while executed by a processor, are adapted to enable the processor to: determine an amount of insulin remaining in the manual insulin delivery device; and determine a dose amount for a time of a previous capping or decapping, and wherein the at least one user interface is configured to display an estimation of active insulin remaining within a user responsive to a current time and one or more dosing events.

Embodiment 15: The pen cap of any one of the preceding Embodiments, wherein the memory segment is configured to store dosing events over a first time period, the time period comprising: a first block of discrete time units; a start time unit of the first block of discrete time units; and an end time of the first block of discrete time units, and wherein the end time corresponds to the current time and at least one of the discrete time units is associated with a dosing event of the dosing events.

Embodiment 16: The pen cap of any one of the preceding Embodiments, wherein the code segment is configured to store instructions that, while executed by the processor, are adapted to enable the processor to record dosing events responsive to detected capping and/or detected decapping and associate the dosing events with one or more discrete time units of the discrete time units.

Embodiment 17: The pen cap of any one of the preceding Embodiments, wherein the code segment is configured to store instructions that, while executed by the processor, are adapted to enable the processor to: select a block of discrete time units that form the first time period responsive to an active insulin estimation request and the current time; select the one or more dosing events that are associated with the first time period; determine the estimation of active insulin remaining within the user responsive to the current time and the one or more dosing events.

Embodiment 18: The pen cap of any one of the preceding Embodiments, wherein the at least one user interface is configured to display the estimation of active insulin remaining as a percentage of a dose amount associated with a most recent dosing action.

Embodiment 19: The pen cap of any one of the preceding Embodiments, further comprising an inner sleeve and an outer housing, the inner sleeve and the outer housing defining a water-tight cavity.

Embodiment 20: The pen cap of any one of the preceding Embodiments, wherein at least a part of one or more of the at least one detection circuit, processor, memory, and wireless communication interface is retained within the watertight cavity.

Embodiment 21: The pen cap of any one of the preceding Embodiments, further comprising an adapter configured to reversibly couple with a corresponding adapter at the manual insulin delivery device.

Embodiment 22: An insulin delivery system comprising: an insulin injection pen for delivering insulin; and a pen cap adapted to be reversibly secured to the insulin injection pen, the pen cap comprising: a wireless communication interface adapted to receive blood glucose data from a glucose sensor system; at least one circuit adapted to detect one whether the pen cap is secured to the insulin injection pen; and at least one user interface to communicate therapy relevant information, therapy recommendations, or a time of a previous capping or decapping of the pen cap from the insulin injection pen; memory to store at least one user-specific dosage parameter or recommended dose; and at least one processor adapted to determine content presented by the user interface, the at least one processor using information about one or more capping or decapping to determine the content.

Embodiment 23: The insulin delivery system of Embodiment 22, wherein the user interface is adapted to display a recommended correction dose of insulin based on an insulin sensitivity factor and target glucose value stored in memory if the pen cap has been capped on the insulin injection pen for at least a threshold period of time.

Embodiment 24: The insulin delivery system any one of the preceding Embodiments, wherein the content includes a representation of a percentage of active insulin remaining within a user based on a time of a previous capping or decapping of the pen cap and a current time.

Embodiment 25: The insulin delivery system of any one of the preceding Embodiments, wherein the replacement pen cap is adapted to determine an amount of insulin remaining in the insulin injection pen and determine a dose amount for the time of a previous capping or decapping, wherein the pen cap displays an estimation of active insulin remaining within the user based a current time and the times and dose amounts associated with one or more a previous capping or decapping of the pen cap.

Embodiment 26: A diabetes management system comprising: a mobile computing device configured to receive one or more user-specific dosage parameters or predetermined doses from a user; a glucose sensor system configured to collect and wirelessly transmit blood glucose data; and a pen cap adapted to be reversibly secured to an insulin injection pen, the pen cap comprising: a wireless communication interface adapted to receive the blood glucose data from the glucose sensor system and the one or more user-specific dosage parameters or predetermined doses from the mobile computing device; at least one circuit adapted to detect one whether the pen cap is secured to the insulin injection pen; and at least one user interface to communicate therapy relevant information, therapy recommendations, or a time of a previous capping or decapping of the pen cap from the insulin injection pen; memory to store the one or more user-specific dosage parameters or predetermined doses received from the mobile computing device; and at least one processor adapted to determine content presented by the user interface, the at least one processor using information about one or more capping or decapping to determine the content.

Embodiment 27: The diabetes management system of Embodiment 26, further comprising an insulin injection pen adapted to be reversibly secured to the pen cap.

Embodiment 28: The diabetes management system of any one of the preceding Embodiments, wherein the user interface is adapted to display a recommended correction dose of insulin based on an insulin sensitivity factor and target glucose value stored in memory if the replacement pen cap has been capped on the insulin injection pen for at least a threshold period of time.

Embodiment 29: The diabetes management system of any one of the preceding Embodiments, further comprising a long-acting insulin pen, a rapid-acting insulin pen, and at least two pen caps, the at least two of the pen caps including a first pen cap adapted to be secured to the long-acting insulin pen and a second pen cap adapted to be secured to the rapid-acting insulin pen.

Embodiment 30: The diabetes management system of any one of the preceding Embodiments, wherein the wireless communication interface is configured to communicate with the glucose sensor system via a near-field communication protocol when the pen cap is positioned in proximity to at least one part of the glucose sensor system.

Embodiment 31: The diabetes management system of any one of the preceding Embodiments, wherein the wireless communication interface is adapted to communicate with the glucose sensor system using a first wireless communication technique having a first communication range and the wireless communication interface is adapted to communicate with the mobile computing device using a second wireless communication technique having a second communication range, the second communication range being greater than the first communication range.

Embodiment 32: The diabetes management system of any one of the preceding Embodiments, wherein the glucose sensor system comprises a flash glucose monitor.

Embodiment 33: A smart electronics module integratable with a manual insulin delivery device, comprising: a wireless communication interface configured to receive blood glucose data from a glucose sensor system; at least one detection circuit configured to detect one or more cappings and one or more decappings of a pen cap from the manual insulin delivery device; at least one user interface configured to present one or more of therapy relevant information, therapy recommendations, and timing information associated with detected cappings or detected decappings of the pen cap; and a processor and a memory, the memory comprising: a data segment configured to store one or more of at least one user-specific dosage parameter and a recommended dose; and a code segment configured to store instructions that, while executed by the processor, are adapted to enable the processor to determine content presentable by the at least one user interface responsive to the timing information associated with the detected cappings or detected decappings of the pen cap.

Embodiment 34: A system, method or device according to any one of the preceding embodiments, wherein the blood glucose data is an interstitial fluid glucose level or based on an interstitial fluid glucose level.

Embodiment 35: A system, method or device according to any one of the preceding embodiments, wherein the blood glucose data is a blood glucose level correlated to an interstitial fluid glucose level.

Embodiment 36: A system, method or device according to any one of the preceding embodiments, wherein the blood glucose data is a blood glucose level.

Additional non-limiting embodiments of the disclosure relate, generally, to therapy management systems, methods, and devices:

Embodiment 1: A reusable accessory for a manual medication delivery device, comprising: a wireless communication interface that is configured to receive analyte measurement data from an analyte sensor system; detection circuitry configured to: detect dosing events associated with dosing actions at the manual medication delivery device; and store a record for each of the one or more dosing events, wherein the record comprises a dosing time of the dosing events; a recommendation system configured to provide one or more medication dose recommendations responsive to one or more of the analyte measurement data and the dosing events; and an adapter configured to reversibly couple to a predetermined portion of the manual medication delivery device.

Embodiment 2: The reusable accessory of Embodiment 1, wherein the manual medication delivery device is a medication injection pen and the reusable accessory is a reusable pen cap for the medication injection pen, and wherein the dosing events associated with the one or more dosing actions are one or more of capping events or decapping events, and the detection circuitry is configured detect capping events or decapping events responsive to sensor signals.

Embodiment 3: The reusable accessory of any one of the preceding Embodiments, further comprising a timer configured to count a number of time units from a decapping event to a subsequent capping event, wherein the circuitry is configured to record a dose time responsive to a determined count greater than a threshold number of time units.

Embodiment 4: The reusable accessory of any one of the preceding Embodiments, wherein the wireless communication interface is configured to receive the analyte measurement data over a first wireless connection when the wireless communication interface is positioned in proximity to at least a portion of the analyte sensor system.

Embodiment 5: The reusable accessory of any one of the preceding Embodiments, wherein the wireless communication interface is configured to communicate, over a second wireless connection, dosing events, therapy parameters, and analyte measurement data with a mobile computing device.

Embodiment 6: The reusable accessory of any one of the preceding Embodiments, wherein the wireless communication interface is configured to receive therapy parameters from the mobile computing device.

Embodiment 7: The reusable accessory of any one of the preceding Embodiments, wherein the first wireless connection has a first communication range and the second wireless connection has a second communication range, wherein the second communication range is greater than the first communication range.

Embodiment 8: The reusable accessory of any one of the preceding Embodiments, wherein the wireless communication interface comprises an NFC chip and the first wireless connection consists of NFC communications between the reusable accessory and the analyte sensor system.

Embodiment 9: The reusable accessory of any one of the preceding Embodiments, wherein the wireless communication interface comprises a wireless radio adapted to enable BLUETOOTH Low Energy communication between the reusable accessory and one or more mobile computing devices.

Embodiment 10: The reusable accessory of any one of the preceding Embodiments, wherein the analyte sensing system comprises a blood glucose meter adapted to provide blood glucose data.

Embodiment 11: The reusable accessory of any one of the preceding Embodiments, wherein the analyte sensor system is a flash glucose monitor adapted to provide glucose data via near-field communication.

Embodiment 12: The reusable accessory of any one of the preceding Embodiments, wherein the analyte sensor system is a continuous glucose monitor adapted to provide blood data via wireless radio communication (e.g., BLUETOOTH LOW ENERGY) and, optionally, near-field communication (NFC).

Embodiment 13: The reusable accessory of any one of the preceding Embodiments, further comprising at least one button for enabling and disabling operational modes of the reusable accessory, including triggering receipt of analyte measurement data, changing a display, stopping or snoozing an alarm, or a combination thereof.

Embodiment 14: A diabetes management system comprising: a glucose sensor system adapted wirelessly transmit blood glucose data; an insulin dosage monitoring device adapted to be reversibly connectable to an insulin delivery device, the insulin dosage monitoring device comprising a display, memory, and processor, the memory storing insulin therapy dosage parameters, the insulin dosage monitoring device being adapted to detect deliveries of insulin from the insulin delivery device, the insulin dosage monitoring device being adapted to wirelessly receive blood glucose data from the glucose sensor system, the processor being adapted to provide insulin dose recommendation based on the stored insulin therapy dosage parameters, the blood glucose data, or a combination thereof; and a mobile computing device including a processor, the mobile computing device being configured to intermittently connect to and receive the at least one characteristic relating to the insulin monitoring device, the blood glucose data, or a combination thereof from the insulin dosage monitoring device via wireless communication.

Embodiment 15: The system of Embodiment 14, wherein the insulin dosage monitoring device comprises a pen cap and the insulin delivery device is an insulin injection pen, wherein the pen cap is adapted to detect deliveries of insulin from the insulin injection pen by detecting pen cap capping events, which may be inferred to be dosing events.

Embodiment 16: The system of any one of the preceding Embodiments, wherein the insulin dosage monitoring device comprises a pen cap and the insulin delivery device is an insulin injection pen, wherein the pen cap is adapted to detect an amount of insulin remaining in the insulin injection pen to determine a timing of, and optionally a dose amount, for each dose.

Embodiment 17: The system of any one of the preceding Embodiments, wherein the insulin dosage monitoring device comprises an accessory that can detect the movement of a plunger or associated mechanical elements that move during an injection of insulin from an insulin injection pen.

Embodiment 18: The system of any one of the preceding Embodiments, wherein the mobile computing device is configured to receive data relating to the at least one characteristic over a selected period of time comprising past data values leading up to a substantially present time value.

Embodiment 19: A method of managing medication therapy by a manual medication delivery device, comprising: receiving analyte measurement data from an analyte sensor system; detecting dosing action events at an accessory configured to reversibly attach to a manual medication delivery device; storing a record for each of the one or more dosing action events, wherein the record comprises a dosing time of a dosing action; and providing one or more medication dose recommendations responsive to the analyte measurement data.

Embodiment 20: The method of Embodiment 19, further comprising receiving, over a first wireless connection, analyte measurement data responsive to the wireless communication interface positioned in proximity to at least a portion of the analyte sensor system.

Embodiment 21: The method of any one of the preceding Embodiments, further comprising communicating over a second wireless connection, dosing events, therapy parameters, and analyte measurement data with a mobile computing device.

Embodiment 22: The method of any one of the preceding Embodiments, further comprising receiving therapy parameters from the mobile computing device over the second wireless connection.

Embodiment 23: The method of any one of the preceding Embodiments, wherein the manual medication delivery device is a medication injection pen and the reusable accessory is a reusable pen cap for the medication injection pen, and wherein the dosing action events associated with one or more dosing actions are one or more of capping events and decapping events, and the detection circuitry is configured detect capping events and decapping events responsive to sensor signals.

Embodiment 24: A smart electronics module integratable with a manual medication delivery device, comprising: a wireless communication interface that is configured to receive analyte measurement data from an analyte sensor system; detection circuitry configured to: detect dosing action events; store a record for each of the one or more dosing actions, wherein the record comprises a dosing time of the dosing action; and receive analyte measurement data received from the analyte sensor system; a recommendation system configured to provide one or more medication dose recommendations responsive to the analyte measurement data; and an adapter configured to reversibly couple to a predetermined portion of the manual medication delivery device.

Embodiment 25: A system, method or device according to any one of the preceding embodiments, wherein the blood glucose data and/or glucose data is an interstitial fluid glucose level or based on an interstitial fluid glucose level.

Embodiment 26: A system, method or device according to any one of the preceding embodiments, wherein the blood glucose data and/or glucose data is a blood glucose level correlated to an interstitial fluid glucose level.

Embodiment 27: A system, method or device according to any one of the preceding embodiments, wherein the blood glucose data and/or glucose data is a blood glucose level.

Additional non-limiting embodiments of the disclosure relate, generally, to user interface for diabetes management systems including flash glucose monitor:

Embodiment 1: A diabetes management system comprising: a flash glucose monitor adapted to be secured to a person with diabetes (PWD), the flash glucose monitor comprising: a sensing portion adapted to detect blood glucose data at regular time intervals, the regular time intervals being less than or equal to every 15 minutes; and a wireless communication interface adapted to transmit blood glucose data when the wireless communication interface is activated by a user, wherein the transmitted blood glucose data for each wireless communication transmission comprises a blood glucose data collected over a data transmission window of at least 1 hour; and a user interface device comprising: a UI wireless communication interface adapted to receive the transmitted blood glucose data at irregular intervals governed at least in part by the actions of the user; a display comprising a touch screen; and a processor and memory, the processor being adapted to execute instructions in the memory to display a representation of glucose values comprising: a graphical representation having a time of the day along the bottom of the graphical representation and a curve of glucose values for each time of the day that has been received, wherein a current time of day is presented on the graphical representation to indicate if there is a gap between a most recent glucose value and the current time of day; and a single numerical value representing a single blood glucose measurement adjacent to the graphical representation; wherein the single numerical value is the most recent glucose value when the screen is not being touched by a user, wherein the processor and memory are configured to change the single numerical value to a prior glucose value when a user touches a portion of the screen corresponding to a prior time of day on the graphical representation.

Embodiment 2: The diabetes management system of Embodiment 1, wherein the graphical representation comprises a point indicator that is positioned along the time axis to correspond to the time of day when the single numerical value was detected.

Embodiment 3: The diabetes management system of any one of the preceding Embodiments, wherein the display is configured so that the user can change the position of the point indicator by pressing the portion of the screen corresponding to position along the time axis at a time prior to the moss recent glucose value.

Embodiment 4: The diabetes management system of any one of the preceding Embodiments, wherein the portion of the screen corresponding to a position along the time axis is a portion of the screen depicting the time axis.

Embodiment 5: The diabetes management system of any one of the preceding Embodiments, wherein the portion of the screen corresponding to a position along the time axis is a portion of the screen depicting the curve of glucose values.

Embodiment 6: The diabetes management system of any one of the preceding Embodiments, wherein the point indicator must be pressed and slid back along the graphical representation to move the point indicator.

Embodiment 7: The diabetes management system of any one of the preceding Embodiments, wherein the point indicator moves back along the curve of glucose values after a user stops pressing a portion of the graphical representation.

Embodiment 8: The diabetes management system of any one of the preceding Embodiments, wherein the display further depicts a trend arrow adjacent to the single numerical value depicting a rate of change of glucose values at the time of the single numerical value.

Embodiment 9: The diabetes management system of any one of the preceding Embodiments, further comprising a reusable accessory adapted to be reversibly secured to an insulin injection pen, wherein the reusable accessory comprises an accessory wireless communication interface adapted to be used by a user to interrogate the flash glucose monitor to receive the blood glucose data.

Embodiment 10: The diabetes management system of any one of the preceding Embodiments, wherein the accessory wireless communication interface is adapted to automatically transmit the blood glucose data to the user interface device.

Embodiment 11: The diabetes management system of any one of the preceding Embodiments, wherein the reusable accessory is adapted to detect an event associated with an administration of insulin from the insulin injection pen.

Embodiment 12: The diabetes management system of any one of the preceding Embodiments, further comprising displaying an injection indicator along the time axis of the graphical representation for each detected event.

Embodiment 13: The diabetes management system of any one of the preceding Embodiments wherein the injection indicator displays an amount of insulin administered.

Embodiment 14: The diabetes management system of any one of the preceding Embodiments, wherein the injection indicator displays a type of insulin administered.

Embodiment 15: The diabetes management system of any one of the preceding Embodiments, further comprising a second reusable accessory adapted to be reversibly secured to a second insulin injection pen, the second insulin injection pen retaining a second type of insulin, wherein the graphical representation includes different injection indicators along the time axis for each reusable accessory.

Embodiment 16: The diabetes management system of any one of the preceding Embodiments, wherein the reusable accessory is a replacement pen cap and the event associated with an administration of insulin from the insulin injection pen is a capping or decapping of the replacement pen cap from the insulin injection pen.

Embodiment 17: The diabetes management system of any one of the preceding Embodiments, wherein the reusable accessory comprises an accessory display, the accessory display depicting a most recent glucose value received from the flash glucose monitor.

Embodiment 18: The diabetes management system of any one of the preceding Embodiments, wherein the user interface device is adapted to receive insulin therapy settings and wirelessly communicate the insulin therapy settings to the reusable accessory, wherein the accessory display is adapted to provide a recommended insulin dose based on the received insulin therapy settings and a most recent glucose value.

Embodiment 19: The diabetes management system of any one of the preceding Embodiments, further comprising a blood glucose meter is wireless communication with one or more components of the system, wherein the graphical representation also includes BGM indicators representing blood glucose measurements from the blood glucose meter.

Embodiment 20: The diabetes management system of any one of the preceding Embodiments, wherein the single numerical value representing a single blood glucose measurement is adapted to depict the blood glucose measurements from the blood glucose meter or glucose values from the flash glucose monitor.

Embodiment 21: A system, method or device according to any one of the preceding embodiments, wherein the blood glucose data and/or glucose values are an interstitial fluid glucose level or based on an interstitial fluid glucose level.

Embodiment 22: A system, method or device according to any one of the preceding embodiments, wherein the blood glucose data and/or glucose values are a blood glucose level correlated to an interstitial fluid glucose level.

Embodiment 23: A system, method or device according to any one of the preceding embodiments, wherein the blood glucose data and/or glucose values are a blood glucose level.

Additional non-limiting embodiments of the disclosure relate, generally, to devices, systems, and methods for estimating active medication from injections:

Embodiment 1: A reusable accessory for a medication injection pen wherein the reusable accessory is adapted to be reversibly attached to a medication injection pen, the reusable accessory being configured to detect an event associated with an injection of medication from the medication injection pen and determine a percentage of medication that remains active for the injection of medication based on a current time and a time of the event associated with an injection.

Embodiment 2: The reusable accessory of Embodiment 1, wherein the reusable accessory is a replacement pen cap adapted to be secured to the medication injection pen such that medication cannot be injected into a user when the replacement pen cap is secured to the medication injection pen, wherein the event associated with an injection of medication is a capping or decapping event that is detected responsive to capping or decapping the medication injection pen with the replacement pen cap.

Embodiment 3: The reusable accessory of Embodiment 1 or Embodiment 2, wherein the reusable accessory comprises a display, wherein the display depicts a visual indicator of an amount of active medication remaining as a percentage.

Embodiment 4: The reusable accessory of one of Embodiments 1-3, wherein the reusable accessory is adapted to determine a dose amount for each detected event associated with an injection of medication, wherein the reusable accessory determines an amount of medication that remains active for a plurality of injections of medication based on a current time and a time of each of the plurality of injections.

Embodiment 5: The reusable accessory for one of Embodiments 1-3, wherein the reusable accessory does not detect or determine a dose amount for each detected event associated with an injection of medication.

Embodiment 6: The reusable accessory of one of Embodiments 1-5, wherein the medication injection pen is an insulin injection pen.

Embodiment 7: The reusable accessory of one of Embodiments 1-6, wherein the reusable accessory comprises a processor and memory, wherein the memory stores one or more user-specific dosage parameters, wherein the processor is adapted to determine a recommended dose of medication based at least in part on the user-specific dosage parameters and a calculation of active medication for one or more prior injections of medication.

Embodiment 8: The reusable accessory of one of Embodiments 1-7, wherein the reusable accessory comprises a wireless communication interface adapted to send or receive wireless communications.

Embodiment 9: The reusable accessory of any one of the preceding Embodiments, wherein the reusable accessory is adapted to receive analyte measurement data from an analyte senor system via the wireless communication interface, wherein the reusable accessory is adapted to determine a recommended dose of medication based at least in part on received analyte measurement data.

Embodiment 10: The reusable accessory of any one of the preceding Embodiments, wherein the reusable accessory is adapted to send data regarding the event associated with each injection of medication to a mobile computing device via the wireless communication.

Embodiment 11: The reusable accessory of any one of the preceding Embodiments, wherein the reusable accessory is adapted to receive user-specific dosage parameters from a mobile computing device via the wireless communication.

Embodiment 12: The reusable accessory of any one of the preceding Embodiments, wherein the wireless communication interface is configured to receive analyte measurement data from an analyte sensor system.

Embodiment 13: The reusable accessory of any one of the preceding Embodiments, wherein the reusable accessory comprises a recommendation system configured to provide one or more medication dose recommendations responsive to the analyte measurement data.

Embodiment 14: The reusable accessory of any one of the preceding Embodiments, wherein the wireless communication interface comprise a first wireless connection having a first communication range and a second wireless connection having a second communication range, wherein the first wireless connection is between the reusable accessory and an analyte sensor system, wherein the second wireless connection is between the reusable accessory and a mobile application on a remote computing device, wherein the second communication range is greater than the first communication range.

Embodiment 15: The reusable accessory of any one of the preceding Embodiments, wherein the wireless communication interface comprises an NFC chip and the first wireless connection consists of NFC communications between the reusable accessory and the analyte sensor system.

Embodiment 16: The reusable accessory of any one of the preceding Embodiments, wherein the wireless communication interface comprises a wireless radio adapted to permit BLUETOOTH Low Energy communications between the reusable accessory and one or more mobile computing devices.

Embodiment 17: The reusable accessory of any one of the preceding Embodiments, wherein the analyte sensor system is a flash glucose monitor adapted to provide glucose data via near-field communication.

Embodiment 18: A diabetes therapy management system comprising: a mobile computing device being adapted to receive one or more user-specific dosage parameters or predetermined doses from a user; a glucose sensor system adapted to collect and wirelessly transmit blood glucose data; and reusable accessory adapted to be reversibly attached to an insulin injection pen, the reusable accessory comprising: a wireless communication interface adapted to receive the blood glucose data from the glucose sensor system and the one or more user-specific dosage parameters or predetermined doses from the mobile computing device; an injection detection mechanism adapted to detect an event associated with an injection of insulin; a processor to determine a percentage of insulin that remains active for each injection of insulin; and a display adapted to display an amount of active insulin remaining in the user as a percentage of the last injection of insulin.

Embodiment 19: The system of Embodiment 18, wherein the reusable accessory detects or determines a dose of insulin for each event associated with an injection of insulin and the display displays an amount of active insulin remaining in the user as a number of units of insulin, which can optionally include multiple doses of insulin at different times.

Embodiment 20: The system of any one of the preceding Embodiments, wherein the reusable accessory does not detect or determines a dose of insulin for each event associated with an injection of insulin.

Embodiment 21: A method of managing a diabetes therapy, comprising: detecting an event associated with an injection of medication from a medication injection pen responsive to an attaching or detaching of a reusable accessory to the medication injection pen; determining a percentage of medication that remains active for the injection of medication based on a current time and time of the event associated with the injection, wherein the event is associated with attaching or detaching a reusable accessory to the medication injection pen.

Embodiment 22: A smart electronics module integratable with a medication injection pen wherein the reusable accessory is adapted to be reversibly attached to a medication injection pen, the reusable accessory being configured to detect an event associated with an injection of medication from the medication injection pen and determine a percentage of medication that remains active for the injection of medication based on a current time and a time of the event associated with an injection.

Embodiment 23: A system, method or device according to any one of the preceding embodiments, wherein the blood glucose data and/or glucose data is an interstitial fluid glucose level or based on an interstitial fluid glucose level.

Embodiment 24: A system, method or device according to any one of the preceding embodiments, wherein the blood glucose data and/or glucose data is a blood glucose level correlated to an interstitial fluid glucose level.

Embodiment 25: A system, method or device according to any one of the preceding embodiments, wherein the blood glucose data and/or glucose data is a blood glucose level.

Additional non-limiting embodiments of the disclosure relate, generally, to insulin injection assistance systems, methods, and devices:

Embodiment 1: A system to assist with the manual dosing of insulin, the system comprising: at least a first glucose sensor system adapted to wirelessly transmit glucose data; at least a first reusable insulin dosing detector adapted to be reversibly connectable to at least a first disposable component comprising a chamber for a first insulin type to form at least part of a first insulin manual delivery assembly, the first reusable insulin dosing detector configured to detect first insulin delivery events associated with the first insulin manual delivery assembly, and a recommendation system comprising a mobile application and a computing device remote from the first reusable insulin dosing detector, wherein the mobile application, while executing at the computing device, is configured to: receive insulin therapy settings, the insulin therapy settings comprising a first insulin type setting; determine first timing data corresponding to one or more first insulin delivery event times of one or more of the first insulin delivery events; analyze the glucose data in combination with the first timing data; and determine an adjustment recommendation or automatic insulin therapy setting change responsive to the analysis.

Embodiment 2: The system of Embodiment 1, further comprising a remote server adapted to receive the glucose data and the first timing data over an internet connection between the mobile computing device and the remote server.

Embodiment 3: The system of any one of the preceding Embodiments, wherein the remote server is configured to analyze the first timing data and the glucose data, and determine the adjustment recommendation or the automatic insulin therapy setting change responsive to the analysis.

Embodiment 4: The system of any one of the preceding Embodiments, wherein the mobile application is configured to analyze the first timing data and the glucose data, determine the adjustment recommendation or the automatic insulin therapy setting change responsive to the analysis.

Embodiment 5: The system of any one of the preceding Embodiments, wherein the first reusable insulin dosing detector is a first reusable accessory, the first disposable component is a first insulin injection pen or a first insulin inhaler, and the first insulin delivery events are associate insulin injection or insulin inhalation, and wherein the first reusable accessory is adapted to reversibly connect to the first insulin injection pen or the first insulin inhaler.

Embodiment 6: The system of any one of the preceding Embodiments, wherein the first reusable accessory is a first replacement cap adapted to be placed over a needle of the first insulin injection pen or adapted to be placed over an inhalation pathway of the first insulin inhaler, wherein the first replacement cap is configured to detect capping and/or de-capping events.

Embodiment 7: The system of any one of the preceding Embodiments, wherein the first reusable accessory is configured to detect the first insulin delivery events responsive to the one or more capping and/or de-capping events.

Embodiment 8: The system of any one of the preceding Embodiments, wherein the first reusable insulin dosing detector is a first reusable smart pen or a first smart inhaler and the first disposable component comprises a first insulin cartridge, wherein the first reusable smart pen or the first smart inhaler is configured to receive the first insulin injection cartridge and configured to be actuated by a user to deliver the first insulin type from the first insulin cartridge.

Embodiment 9: The system of any one of the preceding Embodiments, further comprising: at least a second reusable insulin dosing detector adapted to be reversibly connectable to a second disposable component comprising a chamber for a second insulin type to form at least part of a second insulin manual delivery assembly, wherein the second reusable accessory comprises a second wireless communication interface configured to wirelessly receive a second insulin type setting of the insulin delivery settings from the mobile application, wherein the second reusable insulin dosing detector configured to detect second insulin delivery events associated with the second insulin manual delivery assembly, and wherein the recommendation system is configured to: determine second timing data corresponding to one or more second insulin delivery event times for one or more second insulin delivery events; analyze the glucose data in combination with the first timing data and the second timing data; and determine an adjustment recommendation or automatic change to an insulin delivery setting responsive to the analysis.

Embodiment 10: The system of any one of the preceding Embodiments, wherein the second reusable insulin dosing detector is configured to wirelessly receive glucose data from the first glucose sensor system.

Embodiment 11: The system of any one of the preceding Embodiments, wherein the system disables the wireless communication of the glucose data from the first glucose sensor system to the first reusable insulin dosing detector while the first glucose sensor system is in wireless communication with the second reusable insulin dosing detector.

Embodiment 12: The system of any one of the preceding Embodiments, wherein the second reusable insulin dosing detector is selected from the group consisting of a second smart pen configured to receive a second disposable pen cartridge containing a second insulin type, a second smart inhaler configured to receive a second disposable inhalable insulin cartridge containing a second insulin type, a second replacement pen cap adapted to be secured over a needle of a second disposable insulin injection pen containing the second insulin type, or a second replacement inhaler cap adapted to be secured over an inhalation pathway of an second insulin inhaler.

Embodiment 13: The system of any one of the preceding Embodiments, wherein the first insulin type is selected from a group consisting of a long-acting insulin, a rapid-acting insulin, and a combination long-acting and rapid-acting insulin.

Embodiment 14: The system of any one of the preceding Embodiments, wherein the first glucose sensor system is a blood glucose meter adapted to analyze blood in vitro.

Embodiment 15: The system of any one of the preceding Embodiments, wherein the recommendation system is adapted to analyze the timing data of one or more insulin delivery events and the glucose data to recommend adding a second glucose sensor system selected from the group consisting of continuous glucose monitors and flash glucose monitors.

Embodiment 16: The system of any one of the preceding Embodiments, wherein the first glucose sensor system is a flash glucose monitor.

Embodiment 17: The system of any one of the preceding Embodiments, wherein the first glucose sensor system is configured to communicate a limited glucose data set to the mobile application via a first communication technique having a first communication range and to communicate robust glucose data set to the first or second reusable insulin dosing detector via a second communication technique having a second communication range, the first communication range being greater than the second communication range.

Embodiment 18: The system of any one of the preceding Embodiments, wherein the mobile application can receive glucose data directly from the first glucose sensor system via the first communication technique and the second communication technique.

Embodiment 19: The system of any one of the preceding Embodiments, wherein the first reusable insulin dosing detector comprises a display, wherein the display is configured to provide a recommended first insulin dose of the first insulin type based on the first insulin setting.

Embodiment 20: The system of any one of the preceding Embodiments, wherein the first reusable insulin dosing detector or the mobile application is configured to issue an alert if a detected dose of the first insulin type fails to comply with the first insulin setting.

Embodiment 21: The system of any one of the preceding Embodiments, wherein the system is adapted to determine one or more insulin dose amounts of the first insulin type associated with each detected first insulin delivery event.

Embodiment 22: A method of assisted manual dosing of insulin, the method comprising: receiving first insulin delivery events associated with a first insulin manual delivery assembly, the first insulin manual delivery assembly comprising a first reusable insulin dosing detector reversibly connected to a first disposable component and adapted to detect the first insulin delivery events; determining first timing data corresponding to one or more first insulin delivery event times of one or more of the first insulin delivery events; analyzing the glucose data in combination with the first timing data; and determining an adjustment recommendation or an automatic insulin therapy setting change responsive to the analysis.

Embodiment 23: The method of Embodiment 22, further comprising receiving the first insulin delivery events at a communication interface configured for wireless communication with the first reusable insulin dosing detector.

Embodiment 24: The method of any one of the preceding Embodiments, further comprising: receiving second insulin delivery events associated with a second insulin manual delivery assembly, the second insulin manual delivery assembly comprising a second reusable insulin dosing detector reversibly connected to a second disposable component and adapted to detect the second insulin delivery events; and determining a second adjustment recommendation or a second automatic insulin therapy setting change responsive to the second insulin delivery events.

Embodiment 25: The method of any one of the preceding Embodiments, further comprising receiving glucose data from the first reusable dosing detector.

Embodiment 26: The method of any one of the preceding Embodiments, further comprising receiving glucose data from a first glucose sensor system.

Embodiment 27: A system for remotely assigning with the manual dosing of insulin, the system comprising: receiving first insulin delivery events associated with a first insulin manual delivery assembly, wherein the insulin delivery events are received at a communication interface configured for communication with a reusable insulin dosing detector; determining first timing data corresponding to one or more first insulin delivery event times for one or more first insulin delivery events; analyzing the glucose data in combination with the first timing data; determining an adjustment recommendation or an automatic insulin therapy setting change responsive to the analysis; and providing the adjustment recommendation or the automatic insulin therapy setting change to the communication interface to send to the reusable insulin dosing detector.

Embodiment 28: An insulin manual dosing assistance system, the system comprising: a recommendation system comprising a mobile application executing at a computing device, the mobile application configured to determine insulin delivery adjustment recommendations and insulin therapy setting changes responsive to glucose data associated with one or more insulin delivery events, the recommendation system further configured to: detect a first reusable insulin dosing detector; create an insulin manual delivery assembly profile responsive to the detection, the insulin manual delivery assembly profile associated with an insulin manual delivery assembly of the first reusable insulin dosing detector; and assign one or more insulin therapy settings to the insulin manual delivery assembly profile.

Embodiment 29: The system of Embodiment 28, wherein the recommendation system is configured to, responsive to one or more physiological parameters associated with a user of the recommendation system, either load the one or more insulin therapy settings from memory, or create the one or more insulin therapy settings.

Embodiment 30: The system of any one of the preceding Embodiments, wherein the recommendation system is configured to provide a user prompt at a display of the computing device, the user prompt comprising one an approval for pairing with the first reusable insulin dosing detector.

Embodiment 31: The system of any one of the preceding Embodiments, wherein the recommendation system is configured to send one or more of insulin delivery adjustment recommendations and changes to insulin therapy setting to the reusable insulin dosing detector.

Embodiment 32: The system of any one of the preceding Embodiments, wherein the recommendation system is further configured to receive an instruction to un-pair with a second insulin dosing detector, and, responsive to the instruction to un-pair, delete or deactivate a second insulin manual delivery assembly profile associated with the second insulin dosing detector.

Embodiment 33: The system of any one of the preceding Embodiments, wherein the recommendation system is further configured to: detect a second reusable insulin dosing detector; create a second insulin manual delivery assembly profile responsive to the detection, the second insulin manual delivery assembly profile associated with a second insulin manual delivery assembly of the second reusable insulin dosing detector; and assign one or more second insulin therapy settings to the second insulin manual delivery assembly profile.

Embodiment 34: The system of any one of the preceding Embodiments, wherein the recommendation system is configured to send insulin delivery adjustment recommendations and insulin therapy setting changes to the first and the second reusable insulin dosing detector.

Embodiment 35: The system of any one of the preceding Embodiments, wherein the recommendation system is configured to receive glucose data associated with one or more insulin delivery events of the first and the second reusable insulin dosing detector.

Embodiment 36: The system of any one of the preceding Embodiments, wherein the first reusable insulin dosing detector and the second reusable insulin dosing detector is each a different one of a reusable accessory, a smart insulin pen, and a smart insulin.

Embodiment 37: A system to assist with the manual dosing of insulin, the system comprising: at least a first glucose sensor system adapted to wirelessly transmit glucose data; smart electronics coupled with one or more parts of a first insulin manual delivery assembly, the smart electronics comprising at least a first reusable insulin dosing detector operably connected to at least a first disposable component comprising a chamber for a first insulin type to form at least part of the first insulin manual delivery assembly, the first reusable insulin dosing detector configured to detect first insulin delivery events associated with the first insulin manual delivery assembly; and a recommendation system comprising a mobile application and a computing device remote from the first reusable insulin dosing detector, wherein the mobile application, while executing at the computing device, is configured to: receive insulin therapy settings, the insulin therapy settings comprising a first insulin type setting; determine first timing data corresponding to one or more first insulin delivery event times for one or more first insulin delivery events; analyze the glucose data in combination with the first timing data; and determine an adjustment recommendation or automatic insulin therapy setting change responsive to the analysis.

Embodiment 38: A system, method or device according to any one of the preceding embodiments, wherein the glucose data is an interstitial fluid glucose level or based on an interstitial fluid glucose level.

Embodiment 39: A system, method or device according to any one of the preceding embodiments, wherein the glucose data is a blood glucose level correlated to an interstitial fluid glucose level.

Embodiment 40: A system, method or device according to any one of the preceding embodiments, wherein the glucose data is a blood glucose level.

Additional non-limiting embodiments of the disclosure relate, generally, to pen cap for medication injection pen having temperature sensor:

Embodiment 1: A replacement pen cap for a medication injection pen comprising at least one temperature sensor, wherein the at least one temperature sensor is configured to monitor a temperature of medication within the medication injection pen while the replacement pen cap is associated with the medication injection pen, wherein the replacement pen cap is adapted to detect possible dosing events, wherein the replacement pen cap is adapted to receive analyte measurement data from an analyte sensor system, wherein the replacement pen cap is adapted to determine if medication in the medication injection pen is denatured based on a combination of data from the at least one temperature sensor and the received analyte measurement data subsequent to each detected possible dosing event.

Embodiment 2: The replacement pen cap of Embodiment 1, wherein the at least one temperature sensor is configured to monitor ranges of temperature when the pen cap is associated with the insulin pen.

Embodiment 3: The replacement pen cap of any one of the preceding Embodiments, wherein the pen cap is configured to provide at least one of an alarm or alert to a user when a selected threshold temperature value is sensed, wherein an alert is presented when a threshold is exceeded as a visual display and an audible alarm is triggered when the threshold is exceeded and the pen cap receives glucose values that indicate that one or more prior insulin administrations have been ineffective.

Embodiment 4: The pen cap of any one of the preceding Embodiments, wherein the pen cap is configured to provide data to a user relating to the temperature exposure of the insulin.

Embodiment 5: A smart electronics module integratable with a medication injection pen comprising at least one temperature sensor, wherein the at least one temperature sensor is configured to monitor a temperature of medication within the medication injection pen while the smart electronics module is enabled, wherein the smart electronics module is configured to detect possible dosing events, wherein the smart electronics module is configured to receive analyte measurement data from an analyte sensor system, wherein the smart electronics module is configured to determine if medication in the medication injection pen is denatured based on a combination of data from the at least one temperature sensor and the received analyte measurement data subsequent to each detected possible dosing event.

Embodiment 6: A system, method or device according to any one of the preceding embodiments, wherein the glucose data is an interstitial fluid glucose level or based on an interstitial fluid glucose level.

Embodiment 7: A system, method or device according to any one of the preceding embodiments, wherein the glucose data is a blood glucose level correlated to an interstitial fluid glucose level.

Embodiment 8: A system, method or device according to any one of the preceding embodiments, wherein the glucose data is a blood glucose level.

Additional non-limiting embodiments of the disclosure relate, generally, to user interface for diabetes management systems and devices:

Embodiment 1: A diabetes management system comprising: a computing device including memory and a processor configured to: receive at least one data point relating to prior insulin use of a subject; and calculate a sliding scale glucose correction data set based, at least in part, on the at least one data point relating to prior insulin use of a subject.

Embodiment 2: The system of Embodiment 1, further comprising an insulin pen assembly, wherein the computing device is configured to provide at least some data from the sliding scale glucose correction data set to the insulin pen assembly, and wherein the insulin pen assembly is configured to display the at least some data as a recommended correction insulin dose.

Embodiment 3: The system of any one of the preceding Embodiments, wherein the insulin pen assembly comprises a reusable accessory for an insulin pen and a disposable insulin pen.

Embodiment 4: The system of any one of the preceding Embodiments, wherein the reusable accessory is a replacement pen cap for the disposable insulin pen.

Embodiment 5: The system of any one of the preceding Embodiments, wherein the insulin pen assembly is a reusable insulin injection pen adapted to receive prefilled insulin cartridges for administering insulin.

Embodiment 6: The system of any one of the preceding Embodiments, wherein the insulin pen assembly is adapted to receive blood glucose data from a glucose sensor system, wherein the recommended correction insulin dose is based on the received blood glucose data and that sliding scale glucose correction data set.

Embodiment 7: The system of any one of the preceding Embodiments, wherein the sliding scale glucose correction data set is a linear scale based on the at least one data point comprising an insulin sensitivity factor.

Embodiment 8: The system of any one of the preceding Embodiments, wherein the sliding scale glucose correction data set is a nonlinear scale based on the at least one data point comprising a plurality of data points inputted into the computing device.

Embodiment 9: The system of any one of the preceding Embodiments, wherein the plurality of data points each comprises a range of glucose values and an associated correction dose.

Embodiment 10: The system of any one of the preceding Embodiments, wherein the range of glucose values and the associated correction dose are based on historical insulin use of a subject.

Embodiment 11: A diabetes management system comprising: a computing device including memory and a processor configured to: display a plurality of pictures of meals grouped into a plurality of categories, each category having a similar glycemic impact; and receive a user input of a number of units of insulin that the user would normally administer for meals in that category for each of the plurality of categories; and an insulin pen assembly having a pen display, wherein the computing device is configured to provide the insulin pen assembly with the user inputs for each category, the pen display providing at least one recommended insulin dose based at least in part on the received user inputs for each category.

Embodiment 12: The system of Embodiment 11, wherein the insulin pen assembly displays a recommended insulin dose for each of the plurality of categories.

Embodiment 13: The system of any one of the preceding Embodiments, wherein the computing device receives user input defining a correction factor based on blood glucose levels, wherein the insulin pen assembly is adapted to receive blood glucose data from a glucose sensor system, wherein the insulin pen assembly receives the correction factor from the computing device, wherein each recommended insulin dose is based upon the correction factor and the blood glucose data.

Embodiment 14: The system of any one of the preceding Embodiments, wherein correction factor is a sliding scale glucose correction data set.

Embodiment 15: The system of any one of the preceding Embodiments, wherein the insulin pen assembly comprises a reusable accessory for an insulin pen and a disposable insulin pen.

Embodiment 16: The system of any one of the preceding Embodiments, wherein the reusable accessory is a replacement pen cap for the disposable insulin pen.

Embodiment 17: A system, method or device according to any one of the preceding embodiments, wherein the glucose data is an interstitial fluid glucose level or based on an interstitial fluid glucose level.

Embodiment 18: A system, method or device according to any one of the preceding embodiments, wherein the glucose data is a blood glucose level correlated to an interstitial fluid glucose level.

Embodiment 19: A system, method or device according to any one of the preceding embodiments, wherein the glucose data is a blood glucose level.

Additional non-limiting embodiments of the disclosure relate, generally, to alarms and alerts in diabetes management system:

Embodiment 1: A diabetes management system comprising: one or more signaling outputs configured to present one or more of alarms, alerts, and notifications discernable by a user; at least a first glucose sensor system adapted to wirelessly transmit glucose data via at least a first wireless communication method having a first communication range and a second wireless communication method having a second communication range, wherein the first wireless communication method requires user action and the second wireless communication method is automatic, wherein the second communication range is greater than the first communication range; at least a first reusable accessory adapted to be reversibly connectable to at least a first insulin injection pen, the first reusable accessory being adapted to wirelessly receive the glucose data from the first glucose sensor system via the first wireless communication method upon being moved through the first communication range; and a mobile application on a remote computing device adapted to receive glucose data automatically via the second wireless communication method, the mobile application issuing an alarm at the one or more signaling outputs responsive, at least in part, to the received glucose data.

Embodiment 2: The diabetes management system of Embodiment 1, further comprising an insulin type detector configured to detect a type of insulin in a chamber of an insulin manual delivery device, wherein the first reusable accessory is configured to issue an alarm at the one or more signaling outputs responsive to the detector, the alarm indicating an incorrect insulin type.

Embodiment 3: The diabetes managing system of any one of the preceding Embodiments, further comprising an insulin type detector configured to detect a type of insulin in a chamber of an insulin manual delivery device, wherein the mobile application is configured to issue an alarm at the one or more signaling outputs responsive to the detector, the alarm indicating an incorrect insulin type.

Embodiment 4: The diabetes management system of any one of the preceding Embodiments, wherein the mobile application is configured to compare a detected insulin type to an expected insulin type and output an error signal responsive to the comparison.

Embodiment 5: The diabetes management system of any one of the preceding Embodiments, wherein the mobile application is configured to determine an expected insulin type responsive to dosing action or based on a user provided parameter.

Embodiment 6: The diabetes management system of any one of the preceding Embodiments, further comprising a user confirmation system configured to present a prompt to a user responsive to dosing actions and one or more diabetes management system mode.

Embodiment 7: The diabetes management system of any one of the preceding Embodiments, wherein the user confirmation system is configured to present a prompt for physiological parameters responsive to a hyper system monitoring mode and a high correction dose associated with a recent dosing action.

Embodiment 8: The diabetes management system of any one of the preceding Embodiments, further comprising a user confirmation system configured to present a prompt for glucose measurements responsive to a current time or a time period.

Embodiment 9: The diabetes management system of any one of the preceding Embodiments, wherein the first reusable accessory does not receive glucose data via the first wireless communication method from the first glucose sensor system.

Embodiment 10: The diabetes management system of any one of the preceding Embodiments, wherein the first reusable accessory is adapted to receive glucose data from the mobile application via the second wireless communication method.

Embodiment 11: The diabetes management system of any one of the preceding Embodiments, wherein the first communication method is near-field communication and the second communication method is Bluetooth Low Energy.

Embodiment 12: The diabetes management system of any one of the preceding Embodiments, wherein the alarm is based on a received glucose value being less than a threshold.

Embodiment 13: The diabetes management system of any one of the preceding Embodiments, wherein the alarm is based on a predicted future glucose value being less than a threshold.

Embodiment 14: The diabetes management system of any one of the preceding Embodiments, wherein the first accessory is adapted to detect the administration of insulin from the first insulin injection pen and communicate administration data to the mobile application via the second wireless communication method.

Embodiment 15: The diabetes management system of any one of the preceding Embodiments, wherein the alarm is based at least in part on the administration data.

Embodiment 16: The diabetes management system of any one of the preceding Embodiments, wherein the first insulin injection pen is a long-acting insulin injection pen and the alarm is a missed dose alarm.

Embodiment 17: The diabetes management system of any one of the preceding Embodiments, wherein the alarm is responsive to a high correction dose, a detected dosing event, and a time out.

Embodiment 18: The diabetes management system of any one of the preceding Embodiments, wherein the alarm is responsive to a missed dosing event, a high correction dose, and a time out.

Embodiment 19: A diabetes management system comprising: one or more signaling outputs configured to present one or more of alarms, alerts, and notifications discernable by a user; at least a first glucose sensor system adapted to wirelessly transmit glucose data via at least a first wireless communication method having a first communication range and a second wireless communication method having a second communication range, wherein the first wireless communication method requires user action and the second wireless communication method is automatic, wherein the second communication range is greater than the first communication range; at least a first smart electronics module configured to be integratable with a first insulin injection pen, the first smart electronics module being configured to wirelessly receive the glucose data from the first glucose sensor system via the first wireless communication method upon being moved through the first communication range; and a mobile application on a remote computing device adapted to receive glucose data automatically via the second wireless communication method, the mobile application issuing an alarm at the one or more signaling outputs responsive, at least in part, to the received glucose data.

Embodiment 20: A system, method or device according to any one of the preceding embodiments, wherein the glucose data is an interstitial fluid glucose level or based on an interstitial fluid glucose level.

Embodiment 21: A system, method or device according to any one of the preceding embodiments, wherein the glucose data is a blood glucose level correlated to an interstitial fluid glucose level.

Embodiment 22: A system, method or device according to any one of the preceding embodiments, wherein the glucose data is a blood glucose level.

What is claimed is:

1. A method of assisted manual dosing of insulin, the method comprising:
    receiving first insulin delivery events associated with a first insulin manual delivery assembly, the first insulin manual delivery assembly comprising a first reusable insulin dosing detector reversibly connected to a first disposable component and configured to detect the first insulin delivery events;
    determining first timing data corresponding to one or more first insulin delivery event times of one or more of the first insulin delivery events;
    analyzing glucose data in combination with the first timing data; and
    determining an adjustment recommendation responsive to the analysis of the glucose data and the first timing data.

2. The method of claim 1, further comprising receiving the first insulin delivery events via a communication interface and from the first reusable insulin dosing detector.

3. The method of claim 1, further comprising:
    receiving second insulin delivery events associated with a second insulin manual delivery assembly, the second insulin manual delivery assembly comprising a second reusable insulin dosing detector reversibly connected to a second disposable component and configured to detect the second insulin delivery events; and
    determining a second adjustment recommendation responsive to the second insulin delivery events.

4. The method of claim 1, further comprising receiving glucose data from the first reusable insulin dosing detector.

5. The method of claim 1, further comprising receiving glucose data from a first glucose sensor system.

6. An insulin manual dosing assistance system, comprising:
    a recommendation system comprising a mobile application executing at a computing device, the recommendation system configured to:
        determine insulin delivery adjustment recommendations and insulin therapy setting changes responsive to glucose data associated with one or more insulin delivery events;
        detect a first reusable insulin dosing detector;
        create an insulin manual delivery assembly profile responsive to detecting the first reusable insulin dosing detector, the insulin manual delivery assembly profile associated with an insulin manual delivery assembly of the first reusable insulin dosing detector; and
        assign one or more insulin therapy settings to the insulin manual delivery assembly profile.

7. The system of claim 6, wherein the recommendation system is further configured to, responsive to one or more physiological parameters associated with a user of the recommendation system, implement the one or more insulin therapy settings.

8. The system of claim 7, wherein the recommendation system is further configured to provide a user prompt at a display of the computing device, the user prompt comprising an approval for pairing with the first reusable insulin dosing detector.

9. The system of claim 6, wherein the recommendation system is further configured to, responsive to one or more physiological parameters associated with a user of the recommendation system, generate the one or more insulin therapy settings.

10. The system of claim 6, wherein the recommendation system is further configured to provide one or more of insulin delivery adjustment recommendations or adjustments of the one or more insulin therapy settings to the first reusable insulin dosing detector.

11. The system of claim 6, wherein the recommendation system is further configured to receive an instruction to un-pair the system from a second insulin dosing detector.

12. The system of claim 11, wherein the recommendation system is further configured to, responsive to receiving the instruction to un-pair, delete or deactivate a second insulin manual delivery assembly profile associated with the second insulin dosing detector.

13. The system of claim 6, wherein the recommendation system is further configured to:
    detect a second reusable insulin dosing detector;
    create a second insulin manual delivery assembly profile responsive to detecting the second reusable insulin dosing detector, the second insulin manual delivery assembly profile associated with a second insulin manual delivery assembly of the second reusable insulin dosing detector; and
    assign one or more second insulin therapy settings to the second insulin manual delivery assembly profile.

14. The system of claim 13, wherein the recommendation system is configured to send insulin delivery adjustment recommendations and insulin therapy setting changes to the first and the second reusable insulin dosing detector.

15. The system of claim 13, wherein the recommendation system is configured to receive glucose data associated with one or more insulin delivery events of the first and the second reusable insulin dosing detector.

16. The system of claim 13, wherein the first reusable insulin dosing detector and the second reusable insulin dosing detector is each a different one of a reusable accessory, a smart insulin pen, and a smart insulin.

17. A method for remotely assisting with manual dosing of insulin, the method comprising:
    receiving first insulin delivery events associated with a first insulin manual delivery assembly via a communication interface and from a reusable insulin dosing detector;
    determining first timing data corresponding to one or more first insulin delivery event times of one or more of the first insulin delivery events;
    analyzing glucose data in combination with the first timing data;
    determining an adjustment recommendation responsive to the analysis of the glucose data and the first timing data; and
    providing the adjustment recommendation to the reusable insulin dosing detector.

18. The method of claim 17, further comprising determining one or more insulin dose amounts type associated with each of the received first insulin delivery events.

19. The method of claim 17, further comprising receiving glucose data from at least a first glucose sensor system.

20. The method of claim 17, wherein providing the adjustment recommendation to the reusable insulin dosing detector comprises providing the adjustment recommendation to a reusable smart pen or a first smart inhaler.

* * * * *

UNITED STATES PATENT AND TRADEMARK OFFICE
CERTIFICATE OF CORRECTION

PATENT NO. : 11,957,884 B2
APPLICATION NO. : 17/444007
DATED : April 16, 2024
INVENTOR(S) : Sjolund et al.

Page 1 of 1

It is certified that error appears in the above-identified patent and that said Letters Patent is hereby corrected as shown below:

In the Specification

Column 10, Line 66, "(JOB)" should be --(IOB)--.

Column 21, Line 64, "(e.g., JOB)" should be --(e.g., IOB)--.

Column 32, Line 48, "FIG. 1A, 1B, or 1C" should be --FIGS. 1A, 1B, or 1C--.

Signed and Sealed this
Eleventh Day of June, 2024

Katherine Kelly Vidal
*Director of the United States Patent and Trademark Office*